(12) United States Patent
Abramson et al.

(10) Patent No.: US 8,728,805 B2
(45) Date of Patent: May 20, 2014

(54) METHODS AND COMPOSITIONS FOR TREATMENT OF BONE DEFECTS WITH PLACENTAL CELL POPULATIONS

(75) Inventors: Sascha D. Abramson, Hillsborough, NJ (US); Marian Guelakis, Cranford, NJ (US); Mohammad A. Heidaran, Chatham, NJ (US); Kristen Labazzo, Springfield, NJ (US); Shmuel Yaccoby, Little Rock, AR (US)

(73) Assignee: Anthrogenesis Corporation, Warren, NJ (US)

(*) Notice: Subject to any disclaimer, the term of this patent is extended or adjusted under 35 U.S.C. 154(b) by 657 days.

(21) Appl. No.: 12/546,556

(22) Filed: Aug. 24, 2009

(65) Prior Publication Data

US 2010/0047214 A1 Feb. 25, 2010

Related U.S. Application Data

(60) Provisional application No. 61/090,898, filed on Aug. 22, 2008, provisional application No. 61/090,897, filed on Aug. 22, 2008.

(51) Int. Cl.
*C12N 5/07* (2010.01)

(52) U.S. Cl.
USPC .......................... 435/325; 424/93.7

(58) Field of Classification Search
None
See application file for complete search history.

(56) References Cited

U.S. PATENT DOCUMENTS

| | | |
|---|---|---|
| 3,862,002 A | 1/1975 | Sanders |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,372,581 A | 12/1994 | Anderson |
| 5,385,901 A | 1/1995 | Kaplan et al. |
| 5,415,665 A | 5/1995 | Hessel et al. |
| 5,426,098 A | 6/1995 | Carlino |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,580,777 A | 12/1996 | Bernard et al. |
| 5,591,625 A | 1/1997 | Gerson et al. |
| 5,605,822 A | 2/1997 | Emerson et al. |
| 5,613,982 A | 3/1997 | Goldstein |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,376 A | 5/1998 | Weiss et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

Soncini et al. "Isolation and characterization of mesenchymal cells from human fetal membranes" (Jun. 2007) Journal of Tissue Engineering and Regenerative Medicine. vol. 1, 296-305.*
International Search Report and Written Opinion mailed Dec. 18, 2009 in Application No. PCT/US2009/004801.
U.S. Appl. No. 13/473,509, filed May 16, 2012, Edinger et al.
U.S. Appl. No. 13/480,370, filed May 24, 2012, Edinger et al.
U.S. Appl. No. 13/485,161, filed May 31, 2012, Herzberg et al.
U.S. Appl. No. 13/584,612, filed Aug. 13, 2012, Hariri, et al.
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).

(Continued)

*Primary Examiner* — Jon P Weber
*Assistant Examiner* — Teresa E Knight
(74) *Attorney, Agent, or Firm* — Jones Day

(57) ABSTRACT

Provided herein are osteogenic placental adherent cells (OPACs), methods of using OPACs and OPAC populations, and methods of culturing, proliferating, expanding, or differentiating the OPACs. Further provided herein are methods of using the OPACs to formulate implantable or injectable compositions suitable for administration to a subject. Still further provided herein are methods for treating bone defects with OPACs and compositions comprising OPACs. Also provided herein are methods of using OPACs in the treatment and management of multiple myeloma, e.g., reducing the progression of, halting the progression of, or improving, one or more symptoms of multiple myeloma in an individual having multiple myeloma, comprising administering a plurality of OPACs to the individual.

20 Claims, 21 Drawing Sheets

(56) References Cited

U.S. PATENT DOCUMENTS

Figure 1:
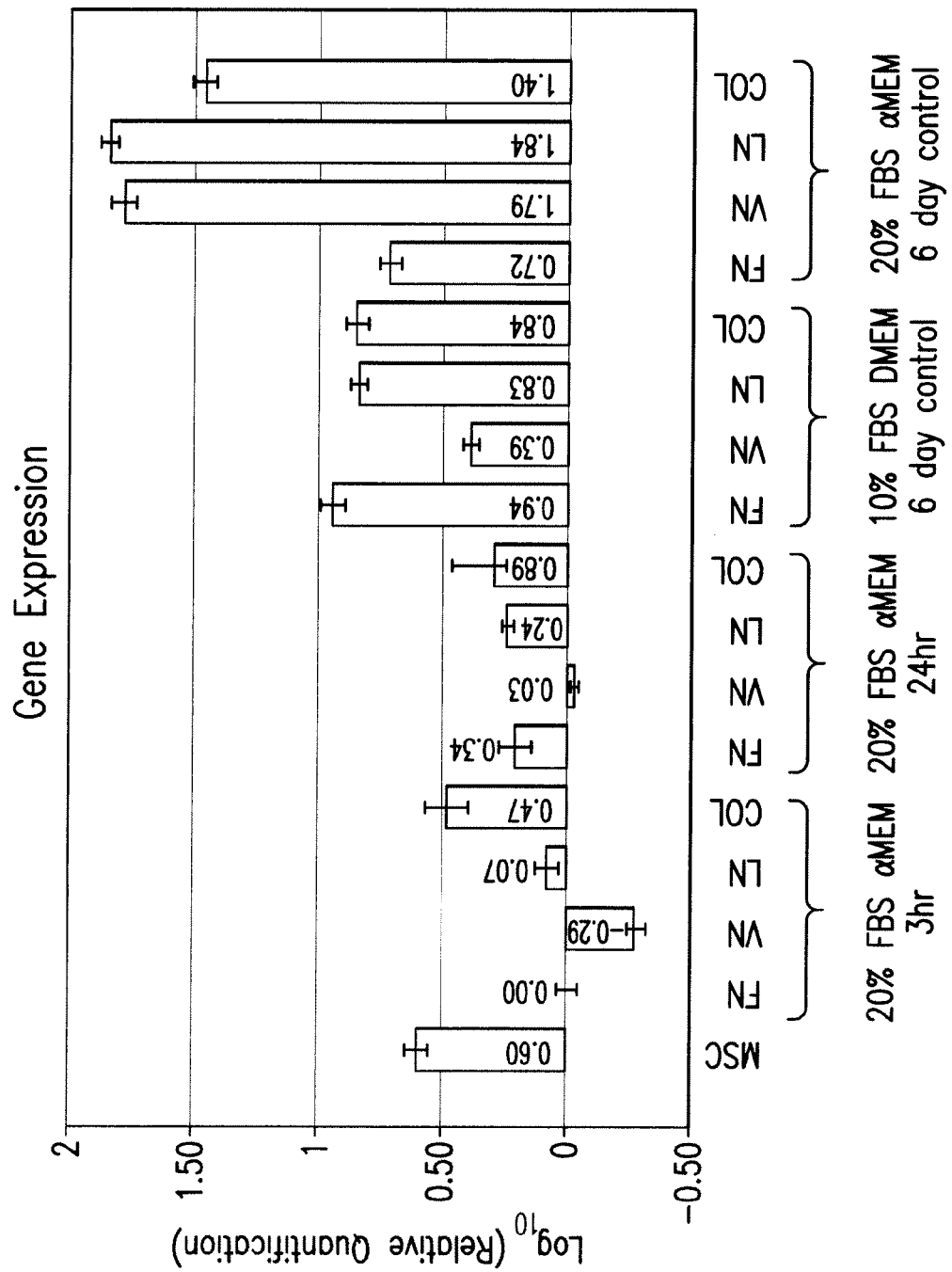

| | | |
|---|---|---|
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,820 A | 10/1999 | Zborowski et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Perrine et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede et al. |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswell |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Matapurkar |
| 6,231,880 B1 | 5/2001 | Perrine |
| 6,239,157 B1 | 5/2001 | Mbalaviele |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,615 B1 | 10/2002 | Srivastava |
| 6,461,645 B1 | 10/2002 | Boyse et al. |
| 6,467,630 B1 | 10/2002 | Zborowski et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakarnam et al. |
| 6,541,024 B1 | 4/2003 | Kadiyala et al. |
| 6,548,299 B1 | 4/2003 | Pykett |
| 6,645,731 B2 | 11/2003 | Terstappen et al. |
| 6,685,936 B2 | 2/2004 | McIntosh et al. |
| 6,709,864 B1 | 3/2004 | Pittenger et al. |
| 6,753,181 B2 | 6/2004 | Atala |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 6,916,655 B2 | 7/2005 | Yasumoto et al. |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,153,500 B2 | 12/2006 | Qasba et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,202,703 B2 | 6/2012 | Edinger et al. |
| 8,263,065 B2 | 9/2012 | Zhang et al. |
| 2001/0005591 A1 | 6/2001 | Qasba et al. |
| 2001/0038836 A1 | 11/2001 | During et al. |
| 2001/0044124 A1 | 11/2001 | Bacus |
| 2002/0028510 A1 | 3/2002 | Sanberg et al. |
| 2002/0036005 A1 | 3/2002 | Kimura |
| 2002/0059106 A1 | 5/2002 | Tani |
| 2002/0061300 A1 | 5/2002 | Gokcen |
| 2002/0086005 A1 | 7/2002 | Chiu et al. |
| 2002/0110544 A1 | 8/2002 | Goldberg et al. |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton et al. |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0045552 A1 | 3/2003 | Robarge et al. |
| 2003/0059414 A1 | 3/2003 | Ho et al. |
| 2003/0068306 A1 | 4/2003 | Dilbert Mehmet |
| 2003/0096841 A1 | 5/2003 | Robarge et al. |
| 2003/0152558 A1 | 8/2003 | Luft |
| 2003/0161818 A1 | 8/2003 | Weiss et al. |
| 2003/0180269 A1 | 9/2003 | Hariri |
| 2003/0187515 A1 | 10/2003 | Hariri |
| 2003/0235090 A1 | 12/2003 | Lee |
| 2003/0235563 A1 | 12/2003 | Strom et al. |
| 2003/0235909 A1 | 12/2003 | Hariri |

(56) References Cited

U.S. PATENT DOCUMENTS

| | | |
|---|---|---|
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0166097 A1 | 8/2004 | Prockop |
| 2004/0171147 A1 | 9/2004 | Hariri |
| 2004/0176434 A1 | 9/2004 | Bennett et al. |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0058641 A1 | 3/2005 | Siemionow |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118147 A1 | 6/2005 | Oh |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0142118 A1 | 6/2005 | Wernet |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0004043 A1 | 1/2006 | Bhagwat et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0122179 A1 | 6/2006 | Zeldis et al. |
| 2006/0128012 A1 | 6/2006 | Arinzeh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0205771 A1 | 9/2006 | Noble et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0077652 A1 | 4/2007 | Peled et al. |
| 2007/0092497 A1 | 4/2007 | Hariri |
| 2007/0092967 A1 | 4/2007 | Han et al. |
| 2007/0116682 A1* | 5/2007 | Atala et al. .......... 424/93.7 |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0253931 A1 | 11/2007 | Varney et al. |
| 2007/0258963 A1 | 11/2007 | Danilkovitch et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044392 A1 | 2/2008 | Kues et al. |
| 2008/0044848 A1 | 2/2008 | Heidaran |
| 2008/0050347 A1 | 2/2008 | Ichim |
| 2008/0050814 A1 | 2/2008 | Allickson |
| 2008/0064098 A1 | 3/2008 | Allickson |
| 2008/0069895 A1 | 3/2008 | Liu et al. |
| 2008/0095749 A1 | 4/2008 | Aggarwal et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0159998 A1 | 7/2008 | Ichim |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2008/0226612 A1 | 9/2008 | Treves et al. |
| 2008/0248005 A1 | 10/2008 | Phan |
| 2008/0254005 A1 | 10/2008 | Riordan et al. |
| 2008/0254538 A1 | 10/2008 | Messina et al. |
| 2008/0260694 A1 | 10/2008 | Gronthos et al. |
| 2008/0260703 A1 | 10/2008 | Riordan et al. |
| 2008/0260704 A1 | 10/2008 | Riordan et al. |
| 2008/0274087 A1 | 11/2008 | Li et al. |
| 2008/0279956 A1 | 11/2008 | Lin |
| 2008/0286249 A1 | 11/2008 | Varney et al. |
| 2008/0286267 A1 | 11/2008 | Sing et al. |
| 2008/0292597 A1 | 11/2008 | Steenblock |
| 2008/0299090 A1 | 12/2008 | Weiss et al. |
| 2008/0305148 A1 | 12/2008 | Fu |
| 2008/0311087 A1 | 12/2008 | Gosiewska et al. |
| 2009/0004738 A1 | 1/2009 | Merchav et al. |
| 2009/0016999 A1 | 1/2009 | Cohen et al. |
| 2009/0053182 A1 | 2/2009 | Ichim et al. |
| 2009/0053805 A1 | 2/2009 | Hariri |
| 2009/0074728 A1 | 3/2009 | Gronthos et al. |
| 2009/0074731 A1 | 3/2009 | Librach et al. |
| 2009/0075381 A1 | 3/2009 | Clarke et al. |
| 2009/0081171 A1 | 3/2009 | Fu et al. |
| 2009/0092653 A1 | 4/2009 | Colter et al. |
| 2009/0104158 A1 | 4/2009 | Young et al. |
| 2009/0104163 A1 | 4/2009 | Deans et al. |
| 2009/0104164 A1 | 4/2009 | Zhang et al. |
| 2009/0123437 A1 | 5/2009 | Takebe |
| 2009/0124007 A1 | 5/2009 | Cho |
| 2009/0136457 A1 | 5/2009 | Sing et al. |

(56) References Cited

U.S. PATENT DOCUMENTS

| | | |
|---|---|---|
| 2009/0136471 A1 | 5/2009 | Heidaran et al. |
| 2009/0142831 A1 | 6/2009 | Hariri |
| 2009/0149371 A1 | 6/2009 | Mistry et al. |
| 2009/0169522 A1 | 7/2009 | Danilkovitch et al. |
| 2009/0169597 A1 | 7/2009 | Brown et al. |
| 2009/0170200 A1 | 7/2009 | Yeh et al. |
| 2009/0186006 A1 | 7/2009 | Murphy |
| 2009/0202479 A1 | 8/2009 | Shi et al. |
| 2009/0208463 A1 | 8/2009 | Pittenger et al. |
| 2009/0214484 A1 | 8/2009 | Mironov |
| 2009/0214493 A1 | 8/2009 | Pittenger et al. |
| 2009/0220464 A1 | 9/2009 | Aggarwal et al. |
| 2009/0226406 A1 | 9/2009 | Hariri |
| 2009/0232781 A1 | 9/2009 | Fu |
| 2009/0232782 A1 | 9/2009 | Fu |
| 2009/0238801 A1 | 9/2009 | Woodbury et al. |
| 2009/0252710 A1 | 10/2009 | Zhang et al. |
| 2009/0257989 A1 | 10/2009 | Vanguri et al. |
| 2009/0263361 A1 | 10/2009 | Lee et al. |
| 2009/0274665 A1 | 11/2009 | Akabutu et al. |
| 2009/0280093 A1 | 11/2009 | Friedlander |
| 2009/0285842 A1 | 11/2009 | Davies et al. |
| 2009/0291061 A1 | 11/2009 | Riordan et al. |
| 2009/0304639 A1 | 12/2009 | Yokoo et al. |
| 2009/0305406 A1 | 12/2009 | Pytlik et al. |
| 2009/0311223 A1 | 12/2009 | Ichim |
| 2009/0311782 A1 | 12/2009 | Chiou et al. |
| 2009/0324609 A1 | 12/2009 | Lodie et al. |
| 2010/0008890 A1 | 1/2010 | Mays et al. |
| 2010/0008992 A1 | 1/2010 | Ichim |
| 2010/0015705 A1 | 1/2010 | Vodyanyk et al. |
| 2010/0015712 A1 | 1/2010 | Sakuragawa et al. |
| 2010/0021434 A1 | 1/2010 | Melamed et al. |
| 2010/0023997 A1 | 1/2010 | Hu et al. |
| 2010/0028306 A1 | 2/2010 | Clarke et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0105132 A1 | 4/2010 | Totey et al. |
| 2010/0120015 A1 | 5/2010 | Hariri |
| 2010/0124569 A1 | 5/2010 | Abbot |
| 2010/0143312 A1 | 6/2010 | Hariri |
| 2010/0183571 A1 | 7/2010 | Paludan et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot et al. |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |
| 2012/0148553 A1 | 6/2012 | Hariri et al. |
| 2012/0171160 A1 | 7/2012 | Johnson, Jr. et al. |
| 2012/0171161 A1 | 7/2012 | Abramson et al. |
| 2012/0171295 A1 | 7/2012 | Abramson |
| 2012/0230959 A1 | 9/2012 | Abbot et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 | 3/2003 |
| EP | 1384775 | 1/2004 |
| EP | 1405649 | 4/2004 |
| EP | 1535994 | 6/2005 |
| EP | 1775341 | 4/2007 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 02/46373 | 6/2002 |
| WO | WO 02/63962 | 6/2002 |
| WO | WO 02/059106 | 8/2002 |
| WO | WO 02/064083 | 8/2002 |
| WO | WO 02/064755 | 8/2002 |
| WO | WO 03/042405 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 02/097052 | 11/2003 |
| WO | WO 03/102151 | 12/2003 |
| WO | WO 2004/035064 | 4/2004 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/097190 | 10/2005 |
| WO | WO 2005/105992 | 11/2005 |
| WO | WO 2005/055929 | 1/2006 |
| WO | WO 2006/015214 | 2/2006 |
| WO | WO 2006/111706 | 10/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/079183 | 7/2007 |
| WO | WO 2007/087292 | 8/2007 |
| WO | WO 2007/087293 | 8/2007 |
| WO | WO 2008/019148 | 2/2008 |
| WO | WO 2008/051568 | 5/2008 |
| WO | WO 2008/060541 | 5/2008 |
| WO | WO 2008/100497 | 8/2008 |
| WO | WO 2012/009422 | 1/2012 |

OTHER PUBLICATIONS

Addison, et al., "Metabolism of Prednisolone by the Isolated Perfused Human Placental Lobule," J. Ster. Biochem. Mol. Biol., 39(1):83-90 (1991).

Aggarwal, et al., "Human Mesenchymal Stem Cells Modulate Allogeneic Immune Cell Responses," Blood 105(4):1815-22 (2005).

Anker In't P, et al., "Isolation of Mesenchymal Stem Cells of Fetal or Maternal Origin from Human Placenta," Stem Cells 22: 1338-45 (2004).

Aplin, "Implantation, trophoblast Differentiation and Haemochorial Placentation: Mechanistic Evidence in vivo and vitro," Journal of Cell Science 99:681-692 (1991).

Ashihara, et al., "Successful Peripheral Blood Stern Cell Transplantation for Myelodysplastic Syndrome," Bone Marrow Transplantation 24(12): 1343-1345 (1999).

Bailo, et al., "Engraftment Potential of Human Amnion and Chorion Cells Derived from Term Placenta," Transplantation 78,1439-1448 (2004).

Ballin, et al., "Autologous Umbilical Cord Blood Transfusion," Arch. Dis. Child Fetal Neonatal. Ed. 73(3):F181-F183 (1995).

Barlogie et al., "High-dose therapy immunomodulatory drugs in

(56) References Cited

OTHER PUBLICATIONS multiple myelorna," *Seminars in Oncology*, 29 (6):26-33 (2002).
Barlow et al., "Comparison of Human Placenta- and Bone Marrow-Derived Multipotent Mesenchymal Stem Cells," Stem Cells and Development 17:1095-1108 (2008).
Barry et al., Birth Defect Research (Part C) 69:250-256, (2003).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Bartlett et al., "Phase I study to determine the safety, tolerability and immunostimulatory activity of thalidomide analogue CC-5013 in patients with metastatic malignant melanoma and other advanced cancers," *British Journal of Cancer*, 90:955-961 (2004).
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(−) Progenitor Cell Recovery Using a Novel Umbilical Cord Blood Collection System," Stem Cells 18(4):245-251(2000).
Bernardeschi et al, J. Exp. Clin. Cancer Res, 22(4):129-133 (2003).
Bersinger, et al., "Effect of Late Pregnancy Serum on the Synthesis and Release of Pregnancy Proteins by the Perfused Human Term Placenta," Reprod. Fertil, Dev. 4:585-538 (1992).
Bertolini, et al., "Retrovirus-Mediated Transfer of the Multidrug Resistance Gene into Human Haemopoietic Progenitor Cells." Haemolotol. 88:318-324 (1994).
Bloxam et al., "Culture of Syncytiotrophoblast for the Study of Human Placental Transfer. Part I: Isolation and Purification of Cytotrophoblast,"Placenta 18:93-93 (1997).
"Human Placental Trophoblast Culture: One-Sided and Two-Sided Models," Proceedings of the Nutrition Society 50:349-354 (1991).
Bossolasco et al., "Molecular and phenotypic characterization of human amniotic fluid cells and their differentiation potential," Cell Research 16:329-336 (2006).
Bullen et al., "Two-Sided Culture of Human Placental Trophoblast, Morphology, immunocytochemistry and Permeability Properties," Placenta 11:431-450 (1990).
Campagnoli, et al., "Identification of Mesenchymal Stem/Progenitor Cells in Human First-Trimester Fetal Blood, Liver, and Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Carter, et al., "Characterization of MSC Potential to Treat GVHD Using Molecular Markers Linked to MSC-Mediated Immunosuppression in Vitro," Blood, 106(11) part 2, Abstract No. 4322, 160B (2005).
Celgene Corporation, "Celgene expands clinical development program for Revimid™. Five additional trials of Revimid initiated in hematological and solid tumor cancers," Press Release, Jun. 2002.
Celgene Corporation, "Initial Phase I solid tumor data on Celgene's lead IMiD™, Revimid™," Press Release, Jun. 2001.
Cester et al., "Cation Transport Across Cultured Trophoblast Membrane in Preeclampsia," Clin. and Exper. Hyper. In Pregnancy, B11(1):59-69 (1992).
Chang, et al., "Placenta-Derived Multipotent Cells Exhibit Immunosuppressive Properties That Are Enhanced in the Presence of Interferon-gamma," Stem Cells 24:2466-2477 (2006).
Chang C Medium (Irvine Scientific, downloaded 2012).
Chao, et al., "Stem Cell Transplantation(Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2633 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21- 30(2000).
Chen, et al., "Therapeutic Benefit of Intravenous Administration of Bone Marrow Stromal Cells after Cerebral Ischemia in Rats," Stroke, 32(4):1005-11 (2001).
Chies et al., "Sickle Cell Disease: A Chronics Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1998).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Contractor, et al., "A comparison of the effects of different perfusion regimens on the structure of the isolated human placental lobule," Cell Tissue Res. 237;609-617 (1984).
Cosma, et al., "Use and Application of Stem Cells in Toxicology," SOT 2003 Annual Meeting, p. 4, Abstract 19 (2003).
Cotte et al., "Preparation of Highly Purified Cytotrophoblast from Human Placenta with Subsequent Modulation to Form Syncytiotrophoblast in Monolayer Cultures," in Vitro 16(8):639-646 (1980).
Czarneski, et al., "Effects of Cord Blood Transfer on the Hematopoietic Recovery Following Sublethal Irradiation in MRL lpr/lpr Mice," Proc. Soc. Exp. Biol. Med. 220(2)79-87 (1999).
D'Amato et al., 2001 "Mechanism of action of thalidomide and 3-aminothalidomide in multiple myeloma," Semin. Oncol. 28:597-601.
Dalgleish, et al., "New thalidomide analogues; anti-cancer, anti-angiogenic and immunostimulatory," *British Journal of Cancer*, 2001, 85 (1)25.
Dallas, et al., "Enhanced T Cell Reconstitution by Hematopoietic Progenitors Expanded ex vivo Using the Notch Ligand Delta1," Blood 109:3579-3587 (2007).
Database Pharmaml XP002369094 retrieved from STN. Database accession No. 1659300, & Marketletter, Oct. 9, 2001.
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:11-253-11-258 (2003).
Davies, et al. "Thalidomide and Immunomodulatory Derivatives Augment Natural Killer Cell Cytotoxicity in Multiple Myeloma," Blood 98(1)210-216 (2001).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: a Report from the National Marrow Donor Program," Blood, 96(13): 4096-4102, (2000).
Davila, et al., "Use and Application of Stem Cells in Toxicology," Toxicological Sciences 79:214-223 (2004).
De Coppi, , et al., "Amniotic Fluid and Chorionic Villi Derived Human Stem Cells for the Engineering of Tissues in Vivo." The Journal of Urology, vol. 171, No. 4, Supplement, Saturday, May 8, p. 21. Abstract 81 (2004).
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. 893.
De Coppi, et al., "Human fetal stem cell isolation from amniotic fluid for tissue reconstruction," J. Urology 167(4 Supp.) 85 (Abstract 338) (2000).
De Coppi, et al., "Pluripotent Stem Cells Derived from Human Chorionic Villi and Amniotic Fluid for Tissue Engineering Applications." Experimental Biologyl/UPS Meeting Abstracts, A1366, Abstract 781.7 (2005).
De Filippo, et al., "Total Penile Urethra Replacement with Autologous Cell-Seeded Collagen Matrices." Urology and Reproductive Surgery, vol. 195, No. 88. Sep. 2002, p. S95.
Delorme et al., Blood 111:2631-2635, Online Dec. 17, 2007 (2008).

(56) References Cited

OTHER PUBLICATIONS

De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Dominici, et al., "Minimal Criteria for Defining Multipotent Mesenchymal Stromal Cells. The International Society for Cellular Therapy Position Statement," Cytotherapy 8(4):315-317 (2006).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10)1199-1212 (2001).
Dushnik-Levinson, et al: "Embryogenesis in vitro: study of differentiation of embryonic stem cells:" Biol Neonate. 67(2):77-83 (1995).
Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C) Cord Blood, Unmatched for HLA for Marrow Transplantation," Am. J: Clin. Pathol. 111:773-781 (1999).
Ende, et al., "Human Umbilical Cord Blood Cells Amerliorate Alzheimer's Disease in Transgenic Mice," J. Med. 32(3-4):241-7 (2001).
Ende, et al., "Hemapoetic Transplantation by Means of Fetal (Cord) Blood: A New Method," Va. Med. Mon. 99:276-280 (1972).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2001).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and irradiation and its Possible Clinical Significance," immunol. Invest. 24(6):999-1012 (1995).
Erices, et al., "Mesenchymal Progenitor Cells in Human Umbilical Cord Blood," Br. J. Haemotol. 109(1).235-242 Abstract (2000).
Evans, "Stem Cell Therapy: Moving towards Reality," Am. J, Obstet. Gynecol. 194:662-663 (2006).
Extended European Search Report dated Mar. 25, 2011 for EP Application No. 10183301.0-2001.
Fasouliotis, et al., "Human umbilical cord blood banking and transplantation: a state of the art," Eur. J. Obstet, Gynecol, Reprod, Biol. 90(1):13-25 (2000).
Fisher et al., "Adhesive and Degradatie Properties of Human Placental Cytotrophoblast Cells in Vitro," Journal od Cell Biology 109:891-902 (1989).
Frank H G, et al., "Cell culture models of human trophoblast: primary culture of trophoblast—a workshop report." Placent Apr. 2001, vol. 22 Suppl A, pp. S107-S109, XP002443188 ISSN: 0143-4004 (Apr. 2001).
Genbacev et al.; "Regulation of Human Placental Development by Oxygen Tension," 277(5332).1669-1672 (1997).
Gluckman, et al., "Cord Blood Heamatopoietic Stem Cells: Biology and Transplantation," in: Hematology, American Society of Hematology Education Program Book (1998) p. 1-14.
Gluckman, et al., "Results of Unrelated Umbilical Cord Blood Hematipoeietic Stem Cell Transplant," Transfusion Cinique et Biologique 8(3):146-154 (2001).
Greenwood et al., "Membrane Potential Difference and Intracellular Cation Concentrations in Human Placental Trophoblast Cells in Culture," Journal of Physiology 492.3:629-640 (1996).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Herrera, et al., "Mesenchyrnal Stem Cells Contribute to the Renal Repair of Acute Tubular Epithelial Injury,"' Int. J. Mol. Med. 14(6):1035-41 (2004).
Himori, et al., Chemotherapeutic susceptibility of human bone marrow progenitor cells and human myelogenous leukemia cells (HI-60) in co-culture: preliminary report. Int J Cell Cloning 2(4):254-62 (1984).
Hirano et al., "CD9 is Expressied in Extravillous Trophoblasts in Association with Integrin $\alpha 3$ and integrin $\alpha 5$," Molecular Human Reproduction 5(2):162-167 (1999).
Hirashima, et al. "Maturation of embryonic stem cells into endothelial cells in an in vitro model of vasculogenesis," Blood. 93(4).1253-63 (1999).
Hoek R M, et al., "Down-regulation of the macrophage lineage though interaction with OX2 (CD200)" Science, American Association for the ADvancement of Science, US, vol, 290, No. 5497, Dec. 1, 2000, pp. 1768-1771, XP002263649 ISSN:0036-8075.
Hows, "Status of Umbilical Cord Blood Transplantation in the Year 2001," J Clin Pathol 54(6).428-434 (2001).
Hoynowski, et al., "Characterization and Differentiation of Equine Umbilical Cord-Derived Matrix Cells," Biochemical and Biophysical Research Communications, 2007; 362:347-53.
Huss, "Isolation of Primary and Immortalized CD34- Hematopoietic and Mesenchymal Stem Cells from Various Sources," Stem Cells 18.1-9 (2000).
Huss, "Perspectives on the Morphology and Biology of CD34-Negative Stem Cells," J. Hematother, Stem. Cell Res. 9(6):783-793 (2000).
Igura, et al., "Isolation and Characterization of Mesencymal Progenitor Cells from Chorionic Villi of Human Placenta," Cytotherapy 6(6). 543-553 (2004).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12).1799-1809 (2003).
International Search Report and Written Opinion from PCT/US2006/949491 dated Sep. 26, 2007.
Iwasaki, "Recent Advances in the Treatment of Graft-Versus-Host Disease,". Clin. Med. Res., 2004; 2(4):243-52.
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).

(56) References Cited

OTHER PUBLICATIONS

Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in the Human Placenta," Trophoblast Research 10:21-65 (1997).
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Kliman et al., "Purification, Characterization, and in Vitro Differentiation of Cytotropholblasts from Human Term Placentae," Endocrinology 118(4):1567-1582 (1986).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Olin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21. Abstract 81.
Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Source of Hmatopoietic Sem Cells for Transplantation into Unrelated Recipients," N. Engl. J. Med. 335: 157-166 (1996).
Landon et al., "The Effects of Ethanol Methotrexate and Diphenylhydantoin on [$^{14}$C] Leucine Incorporation by Human Trophoblasst Cells Cultured in Vitro," British Journal of Obstetrics and Gynaecology 94:252-255 (1987).
Lapchak et al., Expert Opin. Emerging Drugs 12:389-406 (2007).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Le Blanc et al., "Treatment of Severe Acute Graft-Versus-Host Disease With Third Party Haploidentical Mesenchvmal Stem Cells,"• Lancet, 363(9419):1439-41 (2004).
Lebkowski, et al., "Serum and Plasma Levels of FGF-2 and VEGF in Healthy Blood Donors," Cancer J. 7(Suppl 2):583-593 (2001).
Leonard, et al., "The Role of ABC Transporters in Clinical Practice," Oncologist 8:411-424 (2003).
Li et al., "Mesenchymal Stem Cells Derived from Human Placenta Suppress Allogenic Umbilical Cord Blood Lymphocyte Proliferation." Cell Res. 15; 539-547 (2005).
Lin, et al. "Murine CD200(+)CK7(+) trophoblasts in a poly (I:C)-induced embryo resorption model," Reproduction (Cambridge), vol. 130, No. 4, pp. 529-537, XP002443406 ISSN: 1470-1626 (Oct. 2005).
Lipinski et al., "Human Trophoblast Cell-Surface Antigen Defined by Monoclonal Antibodies," Proc. Natl. Acad. Sci. USA, Medical Sciences 78(8)5147-5150 (1981).
Loke et al, "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell, 22(3):817-23 (1980).
Ma et al., "Human Umbilical Cord Wharton's Jelly-Derived Mesenchymal Stem Cells Differentiation into Nerve-Like Cells," Chinese Med. Jour., 118(23):1987-1993 (2005).

Ma et al, "Development of an in vitro Human Placenta Model by the Cultivation of Human Trophoblasts in a Fiber-Based Bioreactor System," Tissue Engineering 5, 91-102 (1999).
MacKay, et al., "Chondrogenic Differentiation of Cultured Human Mesenchymal Stem Cells from Marrow," Tissue Engineering 4(4):415-28 (1998).
McMaster et al, "Human Placental HLA-G Expression is Restricted to Differentiated Cytotrophoblasts," J. Immunol. 154(8):3771-3778 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki et al., "Isolation of Multipotent Stem Cells from Placenta." AASLD Abstracts, Hepatology, Abstract 279, p. 290A (Oct. 2003).
Miki et al., "Production of Hepatocytes from Human Amniotic Stem Cells." Hepatology, Abstract 20, vol. 36, No. 4, Pt. 2 (2002).
Miki et al., "Stem Cell Characteristics of Amniotic Epithelial Cells." Stem Cells Express, published online Aug. 9, 2005; doi:10. 1634/stemcells:2004-0357 (2005).
Minguell, et al., "Mesenchymal Stern Cells," Exp. Biol. Med. 226:507-520 (2001).
Moore, et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Moreira et al., "Thalidomide Exerts Its Inhibitory Action on Tumor Necrosis Factoraby Enhancing mRNA Degradation," J. Expr. Med. 177: 1675-1680 (1993).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol., 2004; 15(7):1794-1804.
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 16:367-373 (1995).
Myllynen "In Search of Models for Hepatic and Placental Pharmacokinetics," [Dissertation] University of Oulu, (2003).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Common. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. To corresponding claims filed in Peru; English translation Jan. 18, 2008.
Oda et al., "Trophoblast Stem Cells," Methods in Enxymology 419(15):387-400 (2006).
Paludan, et al., "Immune Suppression by Placenta Derived Adherent Cells (PDAC) Correlate with Monocyte Chemoattractant Protein-1 and 1L-2 Secretion," Blood 108(11) Part II, p. 48B (2006) (abstract only).

(56) References Cited

OTHER PUBLICATIONS

Paludan, et al., "Placental Derived Stem Cells (PDAC) Suppress the Allo-MLR and the EBV Regression Assay," http://www.call4abstract.com/hem/finalpreview/php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchvmal Stem Cells," Stem Cells, 22(7):1263-78 (2004).
Papaioannou, et al., "Stem Cells from Early Mammalian Embryos" Stem Cells Handbook:19-31 (2004).
Pellegrini, et al., "Fadd and Caspase-8 Are Required for Cytokine-Induced Proliferation of Hemopoietic Progenitor Cells," Blood 106(5):1581-1589 (2005).
Pera, et al., "Human Embryonic Stem Cells," J. Cell. Sci. 113:5-10 (2000).
Petroff et al., "Isolation and Culture of Term Human Trophoblast Cells," Methods in Molecular Medicine, Placenta and Trophoblast, 1(16):208-217 (2006).
Pittenger et al., "Multilineage Potential of Adult Human Mesenchymal Stem Cells," Science 284(5411):143-147 (1999).
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133-A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured, 2007; 38(Supp. 4):S23-33.
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Ringler et al., "In Vitro Systems for the Study of Human Placental Endocrine Function," Endocrine Reviews 11(1):105-123, (1990).
Rong-Hao et al. "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Rubinstein, et al., "Processing and Cryopreservation of Placental/Umbilical Cord Blood for Unrelated Bone Marrow Reconstitution," Proc. Natl. Acad, Sci. USA 92:10119-10122 (1995).
Russo, "Fighting Darwin's Battles. Symposium Marks Evolutionist Victory. Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).

Sapin, "Esterification of Vitamin a by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(Suppl A):S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
ScienCell—Human Amniotic Epithelial Cells. http://www.sciencellonline.com/products/7100htm, (2005).
Seyfried et al., J, Neurosurg. 104:313-318 (2006).
Shamblott, et al., "Derivation of Pluripotent Stem Cells from Cultured Human Primordial Germ Cells," Proc. Natl. Acad. Sci. USA 95(23):13726-13731 (1998).
Sherley, "Asymmetric Cell Kinetics Genes: The Key to Expansion of Adult Stem Cells in Culture", Stem Cell 20:561-72 (2002).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Slaer, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," in Vitro 14(7):631-638 (1978).
Sunderland et al., "HLA A, B, C Antigens Are Expressed on Nonvillous Trophoblast of the Early Human Placenta," Journal of Immunology 127(6):2614-2615 (1981).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-1147 (1998).
Toma et al., "Human Mesenchymal Stem Cells Differentiate to a Cardiomyocyte Phenotype in the Adult Murine Heart," Circulation 105:93-98 (2002).
Truman et al., "Human Placental Cytotrophoblast Cells: Identification and Culture," Arch Gynecol: Obstet. 246:39-49 (1989).
Truman et al., "The Effects of Substrate and Epidermal Growth Factor on Human Placental Trophoblast Cells in Culture," in Vitro Cellular & Developmental Biology 22(9):525-528 (1986).
Turner, et al., "A modified Harvest Technique for Cord Blood Hematopoletic Stem Cells," Bone Marrow Transplantation 10:89-91 (1992).
Ulloa-Montoya, et al., "Culture Systems for Pluripotent Stem Cells," Journal of Bioscience and Bioengineering, 2005; 100(1)12-27.
Viacord, Umblicical cord blood can save lives (Informational brochure), Boston: ViaCell CENTR-BRO R1 Oct. 1, 2001.
Wang et al., "Enhanced Recovery of Hematopoietic Progenitor and Stem Cells from Cultivated, Postpartum Human Placenta," Blood 98(11/1):183a Abstract No. 769 (2001).
Wang et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe et al, "Multilineage Potential of Human Placenta-Derived Mesenchymal Cells," Blood 100(11):517a, Abstract 2022 (2002).
Wiesmann, et al., "Effects of Caspase Inhibitors on Hematopoletic Engraftment After Short-Term Culture," Cell. Transplant. 11(4):351-358 (2002).

(56) References Cited

OTHER PUBLICATIONS

Woods et al., "Osomometric and permeability characteristics of human placental/umbilical cord blood CD34+ cells and their application to cryopreservation," J. Hematother. Stem Cell Res. 9(2):161-173 (2000).

Xu et al., "BMP4 Initiates Human Embryonic Stem Cell Differentiation to Trophoblast," Nature Biology 20:1261-1264 (2002).

Xu et al., "High Sensitivity of Megakaryocytic Progenitor Cells Contained in Placental/Umbilical Cord Blood to the Stresses During Cryopreservation," Bone Marrow Transplantation 34: 537-543 (2004).

Ye et al., "Recovery of Placental-Derived Adherent Cells with Mesenchymal Stem Cell Characteristics," Blood 98(11):147b Abstract No. 4260 (2001).

Yeger et al., "Enzymatic Isolation of Human Trophoblast and Culture on Various Substrates: Comparison of First Trimester with Term Trophoblast," Placenta 10:137-151 (1989).

Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).

Young, et al., "Use of Mesenchymal Stem Cells in a Collagen Matrix for Achilles Tendon Repair," 16:4:406-413 (1998).

Yui et al., "Functional, Long-term Cultures of Human Term Trophoblasts Purified by Column-elimination of CD9 Expressing Cells," Placenta 15:231-246 (1994).

Zhang, et al., "Comparison of Mesenchymal Stem Cells from Human Placenta and Bone Marrow," Chinese Medical Journal, 117(6):882-87 (2004).

Zhang, et al., "Efficient Adena-Associated Virus-Mediated Gene Expression in Human Placenta-Derived Mesenchymal Cells," Microbiol. Immunol. 47(1)1 09-16 (2003).

Zhang, et al., "Human Placenta-Derived Mesenchymal Progenitor Cells Support Culture Expansion of Long-Term Culture-Initiating Cells from Cord Blood CD34+ Cells." Exp. Hematol. 32(7): 657-664 (2004).

Zhao, et al., "Microscopic Investigation of Erythrocyte Deformation Dynamics," Biorheology 43(6):747-65 (2006).

\* cited by examiner

FIG. 13

| Protein | OPAC | PDACs | MSC | Fibroblast | Bone formation |
|---|---|---|---|---|---|
| APRIL | + | + | + | + | → |
| CCR3 | + | + | + | + | → |
| Cerberus 1 | | + | + | + | |
| Csk | + | + | + | | |
| Coagulation Factor III / Tissue Factor | | | | | ← |
| Decorin | + | | | | |
| EDA-A2 | +++ | +++ | +++ | +++ | ← |
| Endostatin | | | | | ← |
| Epiregulin | + | + | | + | ← |
| Endothelin | + | + | | + | → |
| FAM3B | + | + | + | ++ | → |
| FGF-7 / KGF | | | | | |
| Follistatin-like 1 | +++ | + | + | | |
| Glypican 3 | | | | | |
| IGF BP-3 | + | | | | → |
| IGFBP-6 | | | | | |

| Protein | OPAC | PDACs | MSC | Fibroblast | Bone formation |
|---|---|---|---|---|---|
| IGFBP-rp1 / IGFBP-7 | ++ | +++ | ++ | | |
| IGF-II R | + | | + | | |
| IL-2 R alpha | + | + | | + | |
| IL-3 R alpha | | + | | + | |
| IL-5 R alpha | | + | | | |
| IL-9 | | | + | | |
| IL-12 R beta 2 | | | | | |
| IL-17RC | | | | | |
| IL-20 R beta | | + | | + | |
| IL-27 | + | + | + | | ← |
| Latent TGF-beta bp1 | + | | | | |
| LRP-1 | + | + | + | + | |
| LRP-6 | +++ | +++ | | ++++ | |
| NCAM-1/CD56 | | | | + | |
| Osteoprotegerin / TNFRSF11B | ++ | | | + | ← |
| Pentraxin3 / TSG-14 | + | + | | + | |

| Protein | OPAC | PDACs | MSC | Fibroblast | Bone formation |
|---|---|---|---|---|---|
| Prolactin | | +++ | +++ | +++ | → |
| sFRP-4 | + | + | + | | ← |
| Smad 4 | | | | | |
| SPARC | +++ | +++ | +++ | + | |
| Spinesin | + | | + | | |
| TFPI | + | | | | |
| TGF-beta RI / ALK-5 | + | | | + | → |
| TGF-beta RIII | | | | | |
| Thrombospondin (TSP) | | + | + | + | → |
| Thrombospondin-1 | +++ | + | + | + | ← |
| TIMP-1 | +++ | + | + | + | ← |
| TIMP-2 | + | | | | |
| TMEFF1 / Tomoregulin-1 | | | | | |
| TSG-6 | + | + | + | + | → |

US 8,728,805 B2

METHODS AND COMPOSITIONS FOR TREATMENT OF BONE DEFECTS WITH PLACENTAL CELL POPULATIONS

This application claims benefit of U.S. Provisional Patent Application No. 61/090,898, filed Aug. 22, 2008, and U.S. Provisional Patent Application No. 61/090,897, filed Aug. 22, 2008, the disclosures of which are hereby incorporated by reference in their entireties.

1. FIELD

Provided herein are methods of using isolated populations of osteogenic adherent placental cells (OPACs), and methods of using OPACs, e.g., in the treatment of multiple myeloma, and of reducing, stopping, or reversing bone loss associated with or caused by multiple myeloma.

2. BACKGROUND

Multiple myeloma (also known as MM, myeloma, plasma cell myeloma, or Kahler's disease) is a type of cancer of plasma cells, which are antibody-producing immune system cells. Symptoms of multiple myeloma include bone pain, infection, renal failure, anemia, and bone lesions. The disease is considered incurable, and only a few treatments, such as lenalidomide (REVLIMID®) are available and show promise. As such, a need exists for new treatments for multiple myeloma.

3. SUMMARY

Provided herein are isolated osteogenic placental adherent cells (OPACs), populations of OPACs, and cell populations comprising OPACs, wherein the OPACs are present in, and isolated from chorion. In certain embodiments, the OPACs are not isolated from chorionic skirt (laeve). The OPACs exhibit one or more characteristics of stem cells or multipotent cells (e.g., exhibit markers associated with stem cells or multipotent cells, replicate at least 10-20 times in culture in an undifferentiated state, differentiate into adult cells representative of at least one of the three germ layers, etc.), and can adhere to a tissue culture substrate (e.g., tissue culture plastic such as the surface of a tissue culture dish or multiwell plate). Further provided herein are methods of using OPACs in the treatment of bone defects, and in the treatment of bone-related cancers, e.g., multiple myeloma, and methods of using the OPACs to reduce, stop, or reverse bone loss associated with or caused by multiple myeloma.

In one aspect, provided herein is an isolated OPAC, i.e., an isolated osteogenic placental adherent cell that is adherent to tissue culture plastic, osteogenic, and isolated from, chorion, excluding the chorionic skirt (laeve). OPACs are not trophoblasts, cytotrophoblasts, embryonic stem cells, or embryonic germ cells as those cells are known and understood in the art.

In one embodiment, an OPAC is an isolated CD200$^-$ or CD200$^{dim}$ cell, e.g., one that is isolated from chorion, but not from chorionic skirt (laeve). In a specific embodiment, an OPAC is osteogenic. In a specific embodiment, an OPAC is positive for secretion of osteoprotegerin (OPG), e.g., as detected by flow cytometry. Osteoprotegerin is an osteoblast-secreted decoy receptor that specifically binds to osteoclast differentiation factor (ODF) and inhibits osteoclast maturation. Thus, OPACs promote bone formation and reduce osteoclast-mediated bone loss. In another specific embodiment, an OPAC does not express RANKL (Receptor Activator of Nuclear Factor κ B Ligand; see, e.g., GenBank Accession No. AAB86811.1), e.g., as detected by quantitative RT-PCR. RANKL is a protein that activates osteoclasts, which are involved in bone resorption. Thus, OPACs do not promote bone resorption. In another specific embodiment, an OPAC is CD200$^-$ or CD200$^{dim}$, and CD105$^+$. In another specific embodiment, an OPAC is negative for expression of α-smooth muscle actin (see, e.g., GenBank Accession No. NP_001604), negative for RANKL, or positive for expression of NG2 (neural/glial cell 2 chondroitin sulfate proteoglycan), e.g., as determined by antibody staining. In certain embodiments, staining for said NG2 in OPACs is diffuse, as compared to CD200$^+$ (non-dim) tissue culture plastic-adherent placental stem cells, in which NG2 staining is focused. In another specific embodiment, an OPAC is negative for expression of α-smooth muscle actin, negative for RANKL, positive for expression of NG2 and positive for secretion of osteoprotegerin. In another specific embodiment, an OPAC exhibits inducible alkaline phosphatase activity, e.g., as determined by a colorimetric assay. In a more specific embodiment, an OPAC is CD200$^-$ or CD200$^{dim}$, CD105$^+$, as detected by flow cytometry, and is negative for expression of α-smooth muscle actin, negative for RANKL, positive for expression of NG2, positive for expression of osteoprotegerin or exhibits inducible alkaline phosphatase activity. In another more specific embodiment, an OPAC is CD200$^-$ or CD200$^{dim}$, CD105$^+$, and is negative for expression of α-smooth muscle actin, positive for expression of NG2, positive for expression of osteoprotegerin, and exhibits inducible alkaline phosphatase activity.

In another specific embodiment, an OPAC is SSEA3$^+$ or SSEA4$^+$. In a more specific embodiment, an OPAC is SSEA3$^+$ and SSEA4$^+$. In another more specific embodiment, an OPAC is CD200$^-$, CD105$^+$, SSEA3$^+$, and is also negative for expression of α-smooth muscle actin, negative for expression of RANKL, positive for expression of NG2, positive for expression of osteoprotegerin or exhibits inducible alkaline phosphatase activity. In another more specific embodiment, an OPAC is CD200$^-$, CD105$^+$, SSEA4$^+$, and is also negative for expression of α-smooth muscle actin, negative for RANKL, positive for expression of NG2, positive for expression of osteoprotegerin or exhibits inducible alkaline phosphatase activity. In a more specific embodiment, an OPAC is CD200$^-$, CD105$^+$, SSEA3$^+$, SSEA4$^+$, and is also negative for expression of α-smooth muscle actin, negative for RANKL, positive for expression of NG2, positive for expression of osteoprotegerin or exhibits inducible alkaline phosphatase activity.

In certain embodiments, the OPAC, population of OPACs, or population of cells comprising the OPACs facilitates formation of a mineralized matrix in a population of placental cells when said population is cultured under conditions that allow the formation of a mineralized matrix.

Also provided herein are populations of cells comprising OPACs, wherein the population of cells is CD200$^-$ or CD200$^{dim}$. Thus, in one embodiment, provided herein is an isolated population of cells comprising OPACs, wherein said population of cells is not isolated from chorionic skirt (laeve), and wherein said population of cells is CD200$^-$ or CD200$^{dim}$. In a specific embodiment, the population of cells consists essentially of OPACs. In a specific embodiment, said population of cells is osteogenic. In another specific embodiment, said population of cells is CD200$^-$ and CD105$^+$ as detected by flow cytometry. In another specific embodiment, said population of cells is CD200$^{dim}$ and CD105$^+$ as detected by flow cytometry. In another specific embodiment, said population of cells is negative for expression of α-smooth muscle actin, positive for expression of NG2, or positive for secretion of osteoprotegerin. In certain embodiments, staining for said NG2 in OPACs is diffuse, as compared to CD200$^+$ (non-dim) tissue culture plastic-adherent placental stem cells, in which NG2 staining is focused. In another embodiment, said population of cells is negative for expression of RANKL, e.g., as detected by quantitative RT-PCR. In another embodiment, said population of cells is negative for expression of α-smooth muscle actin, positive for expression of NG2 and positive for secretion of osteoprotegerin. In another specific embodiment, said population of cells exhibits inducible alkaline phosphatase activity. In a more specific embodiment, said population is CD200$^-$, CD105$^+$ or CD200$^{dim}$, CD105$^+$ and is also one or more of negative for expression of α-smooth muscle actin, negative for expression of RANKL, positive for expression of NG2, positive for expression of osteoprotegerin or exhibits inducible alkaline phosphatase activity. In a more specific embodiment, said population of cells is CD200$^-$, CD105$^+$ or CD200$^{dim}$, CD105$^+$; is negative for expression of α-smooth muscle actin, negative for RANKL, positive for expression of NG2, positive for expression of osteoprotegerin; and exhibits inducible alkaline phosphatase activity.

In another specific embodiment, said population of cells is SSEA3$^+$ or SSEA4$^+$. In yet another embodiment, said population cells is SSEA3$^+$ and SSEA4$^+$. In yet another embodiment, said population of cells is CD200$^-$, CD105$^+$ or CD200$^{dim}$, CD105$^+$, SSEA3$^+$, and also negative for expression of α-smooth muscle actin, negative for expression of RANKL, positive for expression of NG2, positive for expression of osteoprotegerin or exhibits inducible alkaline phosphatase activity. In another more specific embodiment, said population of cells is CD200$^-$ or CD200$^{dim}$, is CD105$^+$ and SSEA4$^+$, and is also negative for expression of α-smooth muscle actin, negative for expression of RANKL, positive for expression of NG2, positive for expression of osteoprotegerin or exhibits inducible alkaline phosphatase activity. In another more specific embodiment, said population of cells is CD200$^-$ or CD200$^{dim}$; is CD105$^+$, SSEA3$^+$, SSEA4$^+$, negative for expression of α-smooth muscle actin, negative for expression of RANKL, positive for expression of NG2, positive for expression of osteoprotegerin, and/or exhibits inducible alkaline phosphatase activity.

In another specific embodiment, the population of cells comprising OPACs expresses matrix metallopeptidase 9 (MMP9) at a detectably higher level in osteogenic medium than an equivalent number of CD200$^+$, non-dim, adherent placental stem cells, as assessed by Ct values from quantitative real-time PCR.

In other specific embodiments, the population of cells comprising OPACs expresses one or more genes at a detectably higher level than an equivalent number of CD200$^+$, non-dim, adherent placental stem cells, wherein said one or more genes comprise one or more, or all, of BMP3 (bone morphogenetic protein 3), CDH11 (cadherin type 11), COL10A1 (collagen type X, alpha 1), COL14A1 (collagen, type XIV, alpha 1), COL15A1 (collagen, type XV, alpha 1), DMP1 (dentin matrix acidic phosphoprotein 1), DSPP (dentin sialophosphoprotein), ENAM (enamelin), FGFR2 (fibroblast growth factor receptor 2), MMP10 (matrix metalloprotease 10 (stromelysin 2)), TGFB3 (transforming growth factor, β3), and/or TGFBR1 (transforming growth factor β, receptor 1) when an OPAC and said CD200$^+$ placental stem cell are cultured in growth medium, as assessed by Ct values from quantitative real-time PCR.

In another specific embodiment, the population of cells comprising OPACs expresses one or more genes at a detectably higher level than an equivalent number of CD200$^+$, non-dim, adherent placental stem cells, wherein said one or more genes comprise one or more, or all, of AMBN (ameloblastin (enamel matrix protein)), BMP2 (bone morphogenetic protein 2), CALCR (calcitonin receptor), CDH11, COL11A1 (collagen, type XI, alpha 1), COL14A1, COL15A1, COL2A1 (collagen, type II, alpha 1), CSF2 (colony stimulating factor 2 (granulocyte-macrophage)), CSF3 (colony stimulating factor 3 (granulocyte)), DMP1, DSPP, ENAM, FGF3 (fibroblast growth factor 3), GDF10 (growth differentiation factor 10), IGF1 (insulin-like growth factor 1), ITGA1 (integrin, alpha 1 (CD49)), ITGA2 (integrin, alpha 2 (CD49B)), MMP8 (matrix metalloprotease 8 (neutrophil collagenase)), MMP9 (matrix metallopeptidase 9 (gelatinase B, 92 kDa gelatinase, 92 kDa type IV collagenase)), MMP10, PDGFA (platelet-derived growth factor A), SMAD1 (SMAD family member 1), TGFB3, TGFBR1 and/or TGFBR2 (transforming growth factor beta, receptor 2) when the OPACs and said placental stem cells are cultured in osteogenic medium, as assessed by Ct values from quantitative real-time PCR.

In another specific embodiment, the population of cells comprising OPACs expresses one or more genes at a detectably higher level than an equivalent number of adherent CD200$^+$, non-dim, placental stem cells, wherein said one or more genes comprise one or more, or all, of CDH11, COL14A1, COL15A1, DMP1, DSPP, ENAM, MMP10, TGFB3 and/or TGFBR1 regardless of whether the OPACs and said placental stem cells are cultured in growth medium or osteogenic medium, as assessed by Ct values from quantitative real-time PCR.

In another specific embodiment, the population of cells comprising OPACs expresses one or more genes at a detectably lower level than an equivalent number of adherent CD200$^+$, non-dim, placental stem cells, wherein said one or more genes comprise one or more, or all, of AHSG (alpha-2-HS-glycoprotein), ALPL (alkaline phosphatase liver/bone/kidney), EGF (epidermal growth factor), FLT1 (fms-related tyrosine kinase 1 (vascular endothelial growth factor/vascular permeability factor receptor)), IGF2, ITGA2, ITGAM (integrin, alpha M (complement component 3 receptor 3 subunit)), SCARB1 (scavenger receptor class B, member 1), SOX9 (SRY (sex determining region Y)-box 9), TNF (tumor necrosis factor), TWIST1 (Twist homolog 1; formerly blepharophimosis, epicanthus inversus and ptosis 3, acrocephalosyndactyly 3), VCAM1 (vascular cell adhesion molecule 1) and/or VDR (vitamin D (1,25-dihydroxyvitamin D3) receptor) when said OPACs and said placental stem cells are cultured in growth medium, as assessed by Ct values from quantitative real-time PCR In another specific embodiment, the population of cells comprising OPACs expresses one or more genes at a detectably lower level than an equivalent number of adherent CD200$^+$, non-dim, placental stem cells, wherein said one or more genes comprise one or more, or all, of BGN (biglycan), COL11A1, COMP (cartilage oligomeric matrix protein), FGF1 and/or VCAM1 when said OPACs and said placental stem cells are cultured in osteogenic medium, as assessed by Ct values from quantitative real-time PCR.

In another specific embodiment, the population of cells comprising OPACs expresses VCAM1 at a detectably lower level than an equivalent number of adherent CD200$^+$, non-dim, placental stem cells, regardless of whether said OPACs and said placental stem cells are cultured in growth medium or osteogenic medium, as assessed by Ct values from quantitative real-time PCR In another specific embodiment, the population of cells comprising OPACs expresses one or more genes at a detectably higher level than an equivalent number of bone marrow-derived mesenchymal stem cells, wherein said one or more genes comprise one or more, or all, of BMP4, CALCR, CD36, CDH11, COL12A1, COL14A1, COL15A1, COL3A1, COL5A1, DMP1, DSPP, FLT1, MSX1, PDGFA, TGFB3, TGFBR1 and/or TUFT1 (Tuftelin 1), when the OPACs and mesenchymal stem cells are cultured in growth medium, as assessed by Ct values from quantitative real-time PCR;

In another specific embodiment, the population of cells comprising OPACs expresses one or more genes at a detectably higher level than an equivalent number of bone marrow-derived mesenchymal stem cells, wherein said one or more genes comprise one or more, or all, of AMBN, CALCR, COL14A1, COL15A1, CSF3, DMP1, DSPP, ITGA1, ITGA2, MMP10, MMP9, MSX1, PDGFA, TGFB1, TGFB3, TGFBR1 and/or TGFBR2, when the OPACs and mesenchymal stem cells are cultured in osteogenic medium, as assessed by Ct values from quantitative real-time PCR.

In another specific embodiment, the population of cells comprising OPACs expresses one or more genes at a detectably higher level than an equivalent number of bone marrow-derived mesenchymal stem cells, wherein said one or more genes comprise one or more, or all, of CALCR, COL14A1, COL15A1, DMP1, DSPP, MSX1, PDGFA, TGFB3 and/or TGFBR1 regardless of whether said OPACs and said mesenchymal stem cells are cultured in growth medium or osteogenic medium, as assessed by Ct values from quantitative real-time PCR;

In another specific embodiment, the population of cells comprising OPACs expresses one or more genes at a detectably lower level than an equivalent number of bone marrow-derived mesenchymal stem cells, wherein said one or more genes comprise one or more, or all, of ALPL, BGLAP (bone gamma-carboxyglutamate (gla) protein), IGF2, ITGA2, ITGAM, SCARB1 and/or SOX1, when the OPACs and mesenchymal stem cells are cultured in growth medium, as assessed by Ct values from quantitative real-time PCR.

In another specific embodiment, the population of cells comprising OPACs expresses one or more genes at a detectably lower level than an equivalent number of bone marrow-derived mesenchymal stem cells, wherein said one or more genes comprise one or more, or all, of AHSG, ALPL, BGLAP, BGN, BMP3, BMP5, CD36, COL10A1, COL11A1, COL12A1, COL2A1, COL4A3, COMP, EGF, FGF1, FGFR2, IGF2, MMP8, PHEX (phosphate regulating endopeptidase homolog, X-linked), RUNX2 (runt-related transcription factor 2), SCARB1, SOX1, VCAM1 and/or VEGFB, when the OPACs and mesenchymal stem cells are cultured in osteogenic medium, as assessed by Ct values from quantitative real-time PCR.

In another specific embodiment, the population of cells comprising OPACs expresses one or more genes at a detectably lower level than an equivalent number of bone marrow-derived mesenchymal stem cells, wherein said one or more genes comprise one or more, or all, of ALPL, BGLAP, IGF2, SCARB1 and/or SOX9, regardless of whether said OPACs and said mesenchymal stem cells are cultured in growth medium or osteogenic medium, as assessed by Ct values from quantitative real-time PCR. In a more specific embodiment of each of the above embodiments, OPACs and said CD200$^+$ placental stem cells or mesenchymal stem cells have undergone an equivalent number of passages or cell doublings.

In another embodiment, provided herein is a population of cells comprising OPACs, e.g., a population of OPACs, wherein a gene encoding matrix metallopeptidase 9 (MMP9) is induced in said OPACs in osteogenic medium, as compared to expression of MMP9 in growth medium, at least 2, 3, 4 or 5 orders of magnitude greater than said MMP9 is induced in placental stem cells, e.g., CD34$^-$, CD10$^+$, CD105$^+$ tissue culture-adherent multipotent placental cells, in said osteogenic medium, as compared to expression of MMP9 in said growth medium, e.g., as assessed by Ct values from quantitative real-time PCR. In another embodiment, provided herein is a population of cells comprising OPACs, e.g., a population of OPACs, wherein a gene encoding matrix metallopeptidase 9 (MMP9) is induced in said OPACs in osteogenic medium, as compared to expression of MMP9 in growth medium, at least 2, 3, 4 or 5 orders of magnitude greater than said MMP9 is induced in bone marrow-derived mesenchymal stem cells (MSCs) in said osteogenic medium, as compared to expression of MMP9 in said growth medium, e.g., as assessed by Ct values from quantitative real-time PCR. In another embodiment, provided herein is a population of cells comprising OPACs, e.g., a population of OPACs, wherein a gene encoding matrix metallopeptidase 9 (MMP9) is induced in said OPACs in osteogenic medium, as compared to expression of MMP9 in growth medium, at least 2, 3, 4 or 5 orders of magnitude greater than said MMP9 is induced in fibroblasts in said osteogenic medium, as compared to expression of MMP9 in said growth medium, e.g., as assessed by Ct values from quantitative real-time PCR.

In specific embodiments, at least 20%, 30%, 40%, 50%, 60%, 70%, 80%, 90% or 95% of the cells in the population of cells comprising OPACs are CD200$^-$ and/or CD200$^{dim}$. In other specific embodiments, at least 20%, 30%, 40%, 50%, 60%, 70%, 80%, 90% or 95% of the OPACs in the population of cells comprising OPACs are CD200$^-$ and/or CD200$^{dim}$.

Further provided herein is an isolated population of OPACs, wherein said population is produced by isolating chorionic tissue from a placenta, wherein said chorionic tissue is not chorionic skirt (laeve) tissue; digesting the isolated chorionic tissue with a tissue-disrupting enzyme to obtain a population of chorion cells comprising OPACs; and isolating said OPACs from said chorion cells. In a specific embodiment, the tissue-disrupting enzyme is trypsin, dispase or collagenase. In various embodiments, the OPACs, contained within a population of cells obtained from digesting chorionic tissue, are at least about 10%, 20%, 30%, 40%, 50%, 60%, 70%, 80%, 90%, 95%, 99% or at least 99.5% of said population of chorionic cells.

The OPACs, and cell populations comprising OPACs provided herein, include OPACs and OPAC-containing cell populations that have been cultured, e.g., for 1, 2, 3, 4, 5, 6, 7, 8, 9, 10, 11, 12, 13, 14, 15, 16, 17, 18, 19, 20 or more passages, or for 1, 2, 3, 4, 5, 6, 7, 8, 9, 10, 11, 12, 13, 14, 15, 16, 17, 18, 19, 20 population doublings. OPAC populations also includes populations of, e.g., two or more, OPACs in culture, and a population in a container, e.g., a bag.

In another aspect, provided herein is a method of producing osteogenic cells with the ability to mineralize matrix, comprising culturing a plurality of OPACs provided herein or a population of isolated OPACs provided herein, under conditions in which said OPACs differentiate into osteogenic cells, said culturing being for a time sufficient for said osteogenic cells to produce, or facilitate the production of, detectable amounts of mineralized matrix comprising calcium and/or phosphate. In certain embodiments, the OPACs produce, or facilitate the production of, bone.

In another aspect, provided herein is a composition, e.g., an implantable composition, comprising OPACs. In a specific embodiment, the implantable composition comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons. In certain embodiments, the matrix is a synthetic degradable polymer such as, for example, polylactic acid or polyglycolic acid. In certain embodiments, the implantable scaffolding substrate is a β-tricalcium phosphate substrate, a β-tricalcium phosphate-collagen substrate, a collagen substrate, a calcium phosphate substrate, a mineralized human placental collagen substrate, a hyaluronic acid substrate, or a ceramic substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate.

In another aspect, provided herein is a method for treating bone defects in a subject, comprising administering to a subject in need thereof an implantable or injectable composition comprising a population of OPACs provided herein, thereby treating the bone defect in the subject. In certain embodiments, the bone defect is an osteolytic lesion associated with a cancer, a bone fracture, or a spine, e.g., in need of fusion. In certain embodiments, the osteolytic lesion is associated with multiple myeloma, bone cancer, or metastatic cancer. In certain embodiments, the bone fracture is a non-union fracture. In certain embodiments, an implantable composition is surgically implanted, e.g., at the site of the bone defect In certain embodiments, an injectable composition is surgically administered to the region of the bone defect. In certain embodiments, the injectable composition is systemically administered.

In another aspect, provided herein is a method of producing osteogenic cells comprising culturing a plurality of OPACs or a population of isolated OPACs under conditions in which said OPACs differentiate into osteogenic cells, said culturing being for a time sufficient for said OPACs to produce, or facilitate the production of, detectable amounts of mineralized calcium, bone tissue, or bone.

In certain embodiments, provided herein is a method for formulating an injectable composition, comprising combining a population of OPACs with injectable hyaluronic acid or collagen, In certain embodiments, the composition comprises injectable hyaluronic acid. In certain embodiments, the composition comprises injectable collagen. Also provided herein are compositions comprising a population of OPACs and injectable hyaluronic acid or collagen.

In another aspect, provided herein are methods of treating individuals having a bone-related cancer, e.g., multiple myeloma, bone cancer, breast cancer, lung cancer, neuroblastoma, osteosarcoma, Ewing's sarcoma, chondrosarcoma, chordoma, malignant fibrous histiocytoma of bone, fibrosarcoma of bone, metastatic cancer, multiple myeloma, and any form of metastatic cancer characterized by bone metastases. In one embodiment, provided herein is a method of treating an individual having a bone-related cancer, comprising administering to said individual isolated OPACs, e.g., an isolated population of cells comprising OPACs, wherein said OPACs are obtained from chorion, and are adherent to tissue culture plastic, and wherein said OPACs are negative for CD200 or are CD200$^{dim}$, and positive for CD105, and wherein said administering detectably reduces the progression of, halts the progression of, or improves, one or more symptoms of said multiple myeloma. In a specific embodiment, said OPACs are SSEA3$^+$ or SSEA4$^+$. In another specific embodiment, said OPACs are SSEA3$^+$ and SSEA4$^+$. In another specific embodiment, the OPACs are CD200$^-$, CD105$^+$, SSEA3$^+$, and are also negative for expression of α-smooth muscle actin, negative for expression of RANKL, positive for expression of NG2, positive for expression of osteoprotegerin or exhibits inducible alkaline phosphatase activity. In another more specific embodiment, the OPACs are CD200$^-$ and/or CD200$^{dim}$, CD105$^+$, SSEA4$^+$, and are also negative for expression of α-smooth muscle actin, negative for RANKL, positive for expression of NG2, positive for expression of osteoprotegerin or exhibits inducible alkaline phosphatase activity. In a more specific embodiment, the OPACs are CD200$^-$ and/or CD200$^{dim}$, CD105$^+$, SSEA3$^+$, SSEA4$^+$, and are also negative for expression of α-smooth muscle actin, negative for RANKL, positive for expression of NG2, positive for expression of osteoprotegerin or exhibits inducible alkaline phosphatase activity. In other specific embodiments, the OPACs comprise any of the characteristics, or combinations of characteristics, recited in Section 5.1, below.

In another specific embodiment of the method of treatment, said OPACs express one or more genes at a detectably higher level than an equivalent number of CD200$^+$, non-dim, adherent placental stem cells, wherein said one or more genes comprise one or more, or all, of BMP3, CDH1, COL10A1, COL14A1, COL15A1, DMP1, DSPP, ENAM, FGFR2, MMP10, TGFB3, and/or TGFBR1, when said OPACs and said CD200$^+$ placental stem cells are cultured in growth medium, as assessed by Ct values from quantitative real-time PCR.

In another specific embodiment of the method of treatment, said OPACs express one or more genes at a detectably higher level than an equivalent number of adherent CD200$^+$, non-dim, placental stem cells, wherein said one or more genes comprise one or more, or all, of AMBN, BMP2, CALCR, CDH11, COL11A1, COL14A1, COL15A1, COL2A1, CSF2, CSF3, DMP1, DSPP, ENAM, FGF3, GDF10, IGF1, ITGA1, ITGA2, MMP10, MMP8, MMP9, PDGFA, SMAD1, TGFB3, TGFBR1 and/or TGFBR2 when said OPACs and said placental stem cells are cultured in osteogenic medium, as assessed by Ct values from quantitative real-time PCR.

In another specific embodiment of the method of treatment, said OPACs express one or more genes at a detectably higher level than an equivalent number of adherent CD200$^+$, non-dim, placental stem cells, wherein said one or more genes comprise one or more, or all, of CDH11, COL14A1, COL15A1, DMP1, DSPP, ENAM, MMP10, TGFB3 and/or TGFBR1 regardless of whether said OPACs and said placental stem cells are cultured in growth medium or osteogenic medium, as assessed by Ct values from quantitative real-time PCR.

In another specific embodiment of the method of treatment, said OPACs express one or more genes at a detectably lower level than an equivalent number of adherent CD200$^+$, non-dim, placental stem cells, wherein said one or more genes comprise one or more, or all, of AHSG, ALPL, EGF, FLT1, IGF2, ITGA2, ITGAM, SCARB1, SOX9, TNF, TWIST1, VCAM1 or VDR when said OPACs and said placental stem cells are cultured in growth medium, as assessed by Ct values from quantitative real-time PCR.

In another specific embodiment of the method of treatment, said OPACs express one or more genes at a detectably lower level than an equivalent number of adherent CD200+, non-dim, placental stem cells, wherein said one or more genes comprise one or more, or all, of BGN, COL11A1, COMP, FGF1 and/or VCAM1 when said OPACs and said placental stem cells are cultured in osteogenic medium, as assessed by Ct values from quantitative real-time PCR.

In another specific embodiment of the method of treatment, said OPACs express VCAM1 at a detectably lower level than an equivalent number of adherent CD200+, non-dim, placental stem cells, regardless of whether said OPACs and said placental stem cells are cultured in growth medium or osteogenic medium, as assessed by Ct values from quantitative real-time PCR.

In another specific embodiment of the method of treatment, said OPACs express one or more genes at a detectably higher level than an equivalent number of bone marrow-derived mesenchymal stem cells, wherein said one or more genes comprise one or more, or all, of BMP4, CALCR, CD36, CDH11, COL12A1, COL14A1, COL15A1, COL3A1, COL5A1, DSPP, FLT1, MSX1, PDGFA, TGFB3, TGFBR1 and/or TUFT1, when the OPACs and mesenchymal stem cells are cultured in growth medium, as assessed by Ct values from quantitative real-time PCR.

In another specific embodiment of the method of treatment, said OPACs express one or more genes at a detectably higher level than an equivalent number of bone marrow-derived mesenchymal stem cells, wherein said one or more genes comprise one or more, or all, of AMBN, CALCR, COL14A1, COL15A1, CSF3, DMP1, DSPP, ITGA1, ITGA2, MMP10, MMP9, MSX1, PDGFA, TGFB1, TGFB3, TGFBR1 and/or TGFBR2, when the OPACs and mesenchymal stem cells are cultured in osteogenic medium, as assessed by Ct values from quantitative real-time PCR.

In another specific embodiment of the method of treatment, said OPACs express one or more genes at a detectably higher level than an equivalent number of bone marrow-derived mesenchymal stem cells, wherein said one or more genes comprise one or more, or all, of CALCR, COL14A1, COL15A1, DMP1, DSPP, MSX1, PDGFA, TGFB3 and/or TGFBR1 regardless of whether said OPACs and said mesenchymal stem cells are cultured in growth medium or osteogenic medium, as assessed by Ct values from quantitative real-time PCR.

In another specific embodiment of the method of treatment, said OPACs express one or more genes at a detectably lower level than an equivalent number of bone marrow-derived mesenchymal stem cells, wherein said one or more genes comprise one or more, or all, of ALPL, BGLAP (bone gamma-carboxyglutamate (gla) protein), IGF2, ITGA2, ITGAM, SCARB1 and/or SOX1, when the OPACs and mesenchymal stem cells are cultured in growth medium, as assessed by Ct values from quantitative real-time PCR.

In another specific embodiment of the method of treatment, said OPACs express one or more genes at a detectably lower level than an equivalent number of bone marrow-derived mesenchymal stem cells, wherein said one or more genes comprise one or more, or all, of AHSG, ALPL, BGLAP, BGN, BMP3, BMP5, CD36, COL10A1, COL11A1, COL12A1, COL2A1, COL4A3, COMP, EGF, FGF1, FGFR2, IGF2, MMP8, PHEX, RUNX2, SCARB1, SOX1, VCAM1 and/or VEGFB, when the OPACs and mesenchymal stem cells are cultured in osteogenic medium, as assessed by Ct values from quantitative real-time PCR.

In another specific embodiment of the method of treatment, said OPACs or express one or more genes at a detectably lower level than an equivalent number of bone marrow-derived mesenchymal stem cells, wherein said one or more genes comprise one or more, or all, of ALPL, BGLAP, IGF2, SCARB1 and/or SOX9, regardless of whether said OPACs and said mesenchymal stem cells are cultured in growth medium or osteogenic medium, as assessed by Ct values from quantitative real-time PCR.

In another specific embodiment of the method of treating multiple myeloma, said OPACs: express one or more genes at a detectably higher level than an equivalent number of bone marrow derived mesenchymal stem cells, wherein said one or more genes comprise one or more of BMP4, BMP6, CD36, CDH11, COL14A1, COL15A1, COL1A1, COL3A1, COL5A1, CSF2, CTSK, FGF2, FGFR1, FLT1, ITGA1, MINPP1, MMP9, MSX1, PDGFA, SERPINH1, TGFB3 and TGFBR1, wherein said OPACs and said mesenchymal stem cells have undergone an equivalent number of passages or cell doublings; or express one or more genes at a detectably higher level than an equivalent number of fibroblast cells, wherein said one or more genes comprise one or more of BMP4, BMP6, CDH11, COL14A1, COL15A1, COL1A1, COL3A1, COL5A1, FLT1, IGF1R, ITGA1, MINPP1, PDGFA, SERPINH1, SMAD3, TGFB1, TGFB2, TGFB3, TGFBR1, TNF, TUFT1, VCAM1 and VEGFA, and wherein said fibroblast cells have undergone an equivalent number of passages or cell doublings.

In another specific embodiment of the method of treating an individual having multiple myeloma, said OPACs secrete one or more of the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 or TIMP-2. In a more specific embodiment, said OPACs secrete the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 and TIMP-2.

In another specific embodiment of the method of treatment, said one or more symptoms of multiple myeloma are bone pain, osteocytic lesions (e.g., visible by X-ray or magnetic resonance imaging (MRI)), osteoporosis, anemia, hypercalcemia or a symptom due to hypercalcemia, or renal failure. In another specific embodiment, said administering causes a detectable increase in, or lessening of the reduction of, bone mineral density or bone mineral content in said individual. In another specific embodiment, said administering comprises administering at least $1 \times 10^8$ OPACs/kg to said individual. In other specific embodiments, said individual has never been treated for multiple myeloma; said individual has been treated for multiple myeloma and responds to non-OPAC therapy; said individual has been treated for multiple myeloma and has not responded to non-OPAC therapy, but the course of multiple myeloma in said individual has not progressed; or said individual has progressive multiple myeloma.

In yet another aspect, provided herein is a method for treating bone defects in a subject, comprising administering to a subject in need thereof an implantable or injectable composition comprising a population of OPACs, thereby treating the bone defect in the subject. In certain embodiments, the bone defect is (a) an osteolytic lesion associated with a cancer, (b) a bone fracture, (c) a spine in need of fusion, (d) a nonunion fracture, or (e) osteoporosis. In certain embodiments, the osteolytic lesion is associated with multiple myeloma, bone cancer, or metastatic cancer. In certain embodiments, the bone fracture is a non-union fracture. In certain embodiments, an implantable composition comprising a population of OPACs is administered to the subject. In certain embodiments, the implantable composition is surgically implanted. In certain embodiments, an injectable composition comprising a population of OPACs is administered to the subject. In certain embodiments, the injectable composition is surgically administered to the region of the bone defect. In certain embodiments, the injectable composition is systemically administered.

In yet another aspect, provided herein is a method for treating bone defects in a subject, comprising administering to a subject in need thereof an implantable or injectable composition comprising a population of OPACs, wherein said OPACs cause or facilitate the formation of bone or bone tissue in the subject, and thereby treating the bone defect in the subject. In certain embodiments, the bone defect is (a) an osteolytic lesion associated with a cancer, (b) a bone fracture, (c) a spine in need of fusion, (d) a nonunion fracture, or (e) osteoporosis. In certain embodiments, the osteolytic lesion is associated with multiple myeloma, bone cancer, or metastatic cancer. In certain embodiments, the bone fracture is a nonunion fracture. In certain embodiments, an implantable composition comprising a population of OPACs is administered to the subject. In certain embodiments, the implantable composition is surgically implanted. In certain embodiments, an injectable composition comprising a population of OPACs is administered to the subject. In certain embodiments, the injectable composition is surgically administered to the region of the bone defect. In certain embodiments, the injectable composition is systemically administered.

3.1 DEFINITIONS

As used herein, "consisting essentially of," in the context of a population of cells comprising OPACs, means that the population of cells is, e.g., at least 95%, at least 96%, at least 97%, at least 98%, at least 95% or at least 95.5% OPACs.

As used herein, the terms "OPAC" and OPACs" refer to the cells described in Section 5.1, below.

As used herein, "$CD200^{dim}$", when referring to a cell, means that the cell displays fluorescence intensity for CD200 in flow cytometry that is no more than 20-30% above isotype control. As used herein, a population of cells is $CD200^{dim}$ if at least 60% of the cells in the population either do not express CD200 or are $CD200^{dim}$, and the cell population, as a whole, in a flow cytometric assay, displays a CD200 fluorescence intensity that is no more than 40-60% above isotype control. It is noted that a $CD200^{dim}$ population can comprise $CD200^+$ (non-dim) cells.

As used herein, the term "SH2" refers to an antibody that binds an epitope on the marker CD105. Thus, cells that are referred to as $SH2^+$ are $CD105^+$.

As used herein, the terms "SH3" and SH4" refer to antibodies that bind epitopes present on the marker CD73. Thus, cells that are referred to as $SH3^+$ and/or $SH4^+$ are $CD73^+$.

As used herein, the term "isolated OPAC" means an OPAC that is substantially separated from other, non-OPAC of the tissue, e.g., chorion, from which the OPACs is derived. An OPAC is "isolated" if at least about 50%, 60%, 70%, 80%, 90%, 95%, or at least 99% of the non-OPACs with which the OPACs are naturally associated are removed from the OPACs, e.g., during collection and/or culture of the OPACs.

As used herein, the term "population of isolated cells" means a population of cells that is substantially separated from other cells of the tissue, e.g., placenta, from which the population of cells is derived. A population of OPACs is "isolated" if at least about 50%, 60%, 70%, 80%, 90%, 95%, or at least 99% of the cells with which the population of OPACs, or cells from which the population of OPACs is derived, is naturally associated are removed from the population of OPACs, e.g., during collection and/or culture.

As used herein, the term "placental stem cell" refers to a stem cell or progenitor cell that is derived from a mammalian placenta, regardless of morphology, cell surface markers, or the number of passages after a primary culture. The term "placental stem cell" as used herein does not, however, refer to a trophoblast. A cell is considered a "stem cell" if the cell retains at least one attribute of a stem cell, e.g., a marker or gene expression profile associated with one or more types of stem cells; the ability to replicate at least 10-40 times in culture, the ability to differentiate into cells of all three germ layers; the lack of adult (i.e., differentiated) cell characteristics, or the like. The terms "placental stem cell" and "placenta-derived stem cell" may be used interchangeably.

As used herein, a cell is "positive" for a particular marker when that marker is detectable. For example, an OPACs is positive for, e.g., CD105 because CD105 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell. similarly, a population of cells is positive for a marker when, e.g., at least 50%, 55%, 60%, 65%, 70%, 75%, 80%, 85%, 90% or 95% of cells in the population express the marker.

As used herein, an "osteogenic cell" is a cell that is capable of either depositing hydroxyapatite, the main component of bone, or differentiating into a cell that is capable of depositing hydroxyapatite. An "osteogenic cell" is specifically contemplated as encompassing a cell ordinarily referred to as an osteoblast or an osteocyte. See Section 5.1.6, below, for exemplary conditions under which an osteogenic placental adherent cell can differentiate into a cell that can deposit hydroxyapatite.

As used herein, a "matrix" refers to a three-dimensional substance that is characterized by pores dispersed throughout the substance. The pores are suitable, for example, for growth of cells, e.g., stem cells, OPACs, and/or osteogenic cells, within the matrix. Exemplary matrices include, but are not limited to, a β-tricalcium phosphate substrate, a β-tricalcium phosphate-collagen substrate, a collagen substrate, a calcium phosphate substrate, a mineralized human placental collagen substrate, a hyaluronic acid substrate, and a ceramic substrate. Preferably, the matrix can be mineralized by an osteogenic cell present in the pores of the matrix.

4. BRIEF DESCRIPTION OF THE FIGURES

FIG. 1: Gene expression of OPACs obtained by selective adhesion. X axis: $\log_{10}$ relative quantification alkaline phosphatase gene expression. X axis: Experimental conditions.

Figure 2:
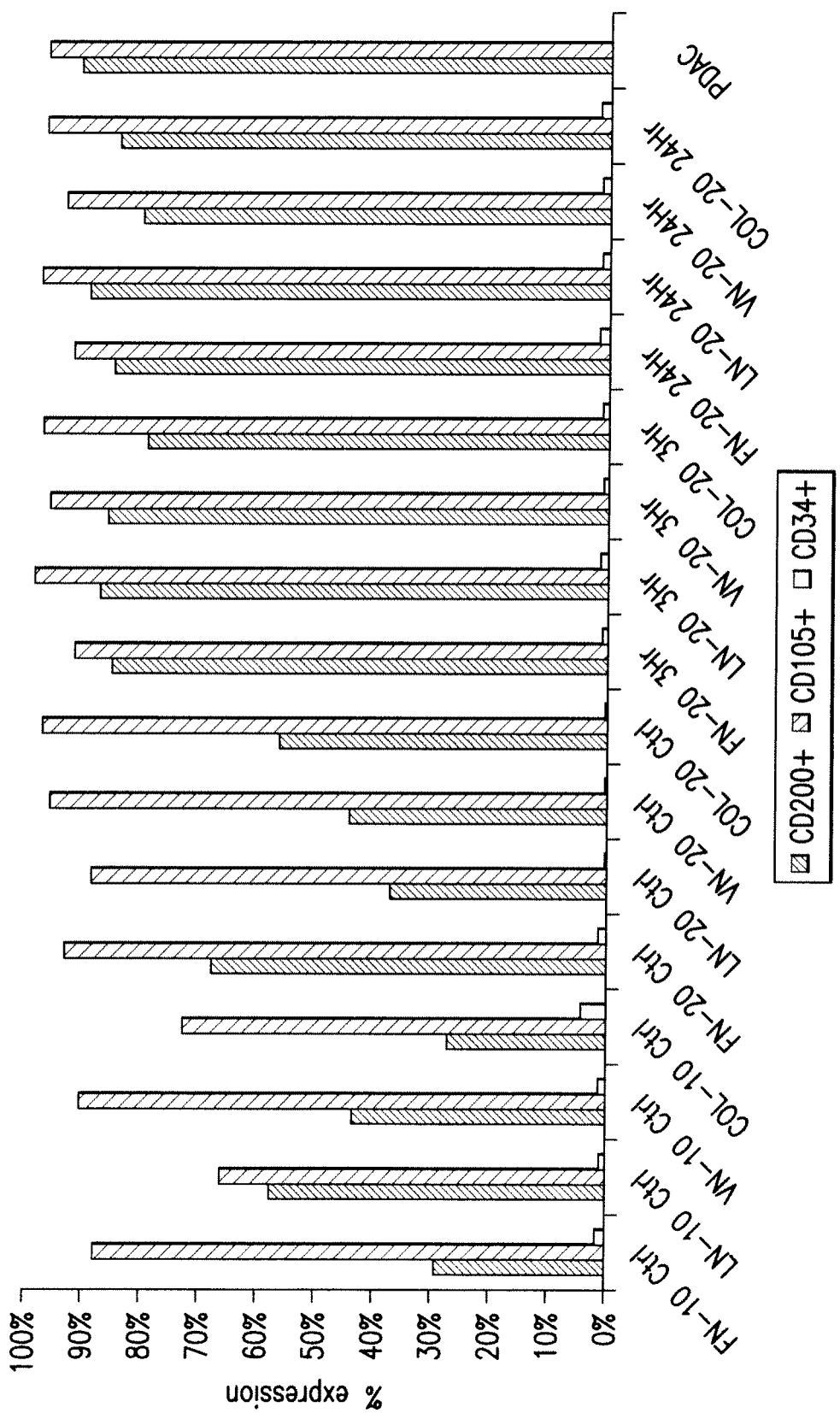

FIG. 2: Immunophenotype of OPACs obtained by selective adhesion with respect to CD34, CD105 and CD200. LN: laminin. VN: vitronectin. FN: fibronectin. COL: collagen. 10: 10% fetal bovine serum. 20: 20% fetal bovine serum. Ctrl: culture of OPACs on the indicated surface coating for 6 days.

Figure 3:
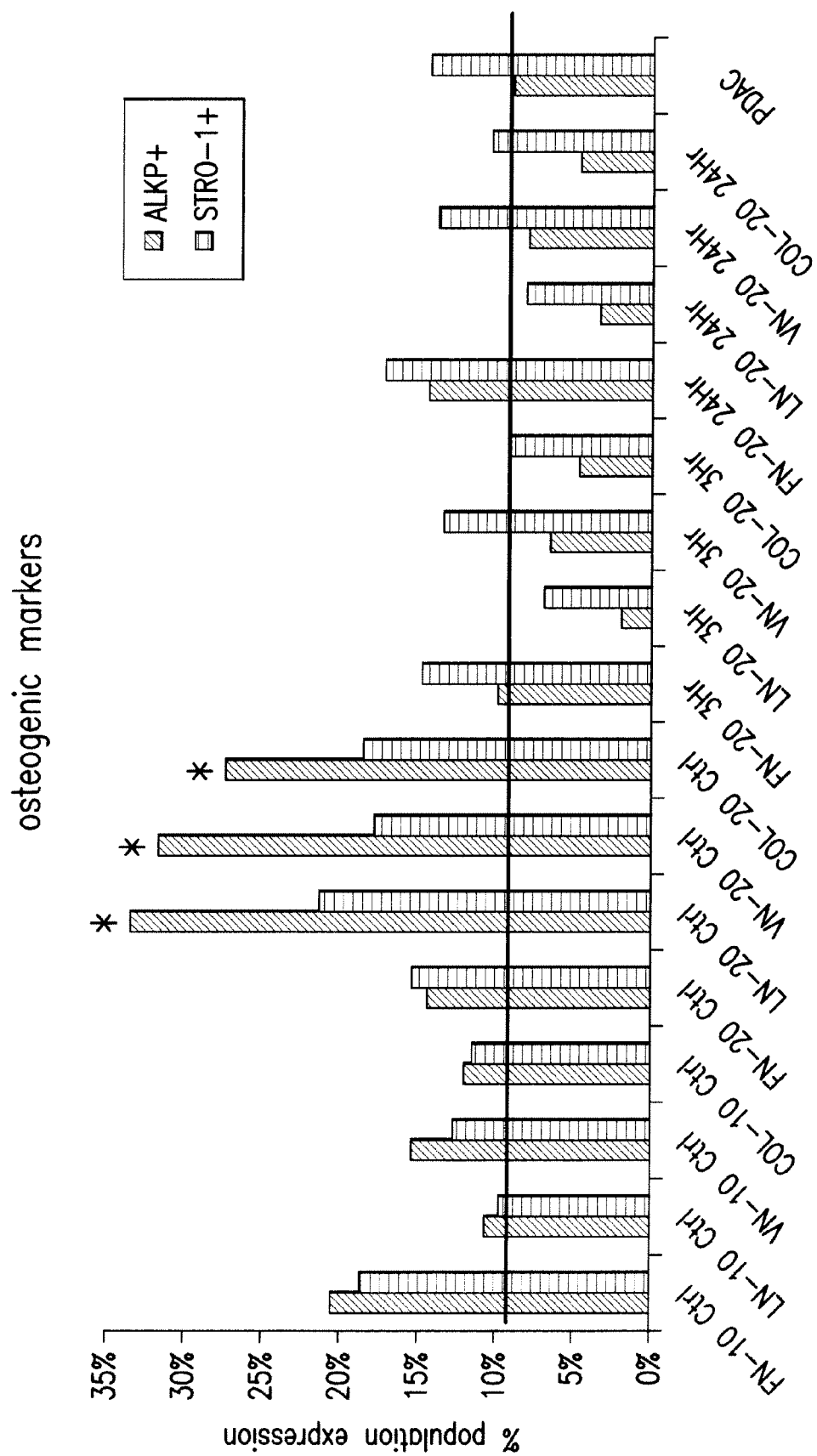

FIG. 3: Immunophenotype of osteogenic markers of OPACs obtained by selective adhesion. LN: laminin. VN: vitronectin. FN: fibronectin. COL: collagen. 10: 10% fetal bovine serum. 20: 20% fetal bovine serum. Ctrl: culture of OPACs on the indicated surface coating for 6 days. Asterisks: significant difference compared to $CD10^+$, $CD34^-$, $CD105^+$ placental stem cell control (horizontal line).

Figure 4:
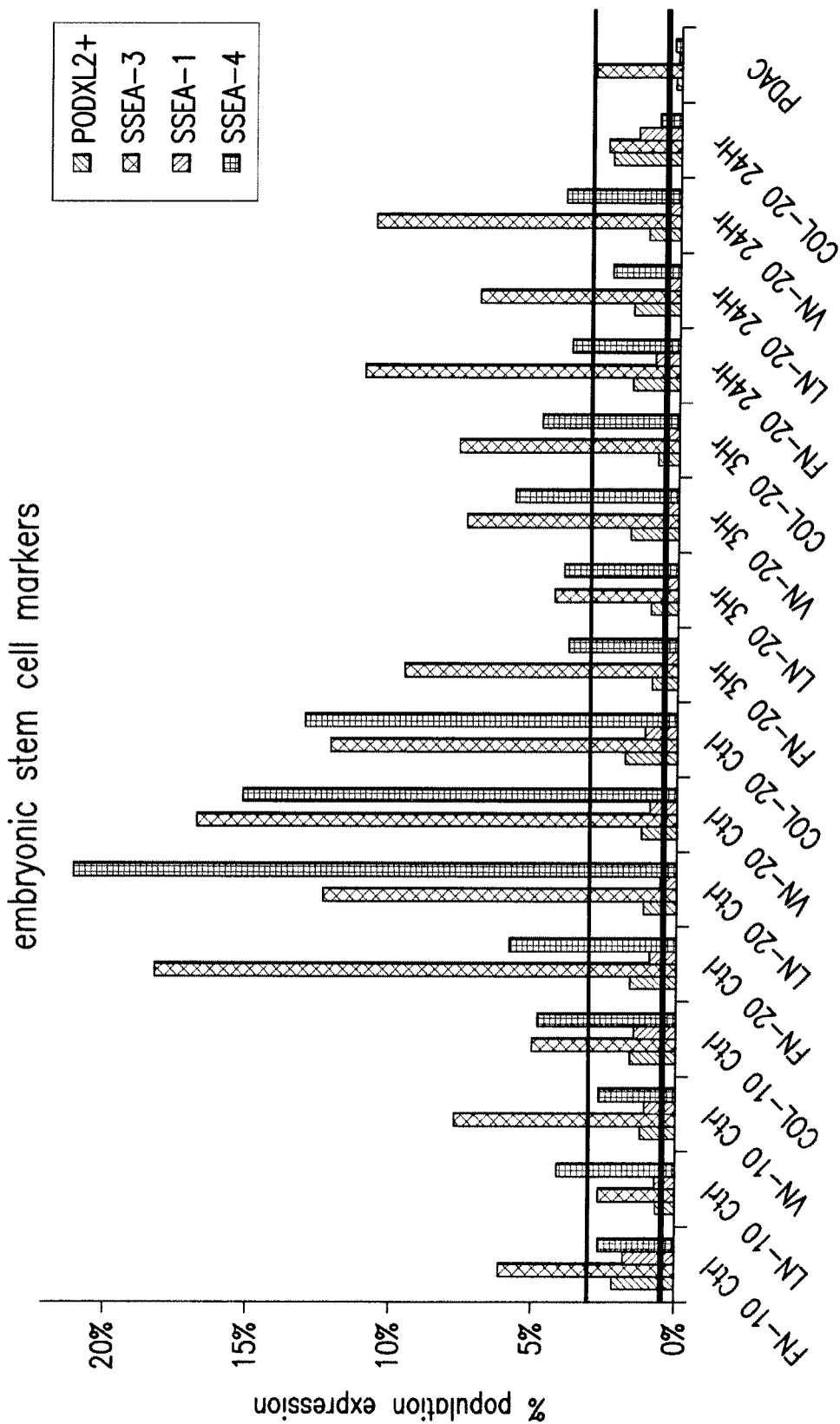

FIG. 4: Immunophenotype of embryonic stem cells markers of OPACs obtained by selective adhesion. LN: laminin. VN: vitronectin. FN: fibronectin. COL: collagen. 10: 10% fetal bovine serum. 20: 20% fetal bovine serum. Ctrl: culture of OPACs on the indicated surface coating for 6 days. Upper horizontal line: $CD10^+$, $CD34^-$, $CD105^+$ placental stem cell expression of SSEA-3; lower horizontal line: $CD10^+$, $CD34^-$, $CD105^+$ placental stem cell expression of SSEA-4.

Figure 5:
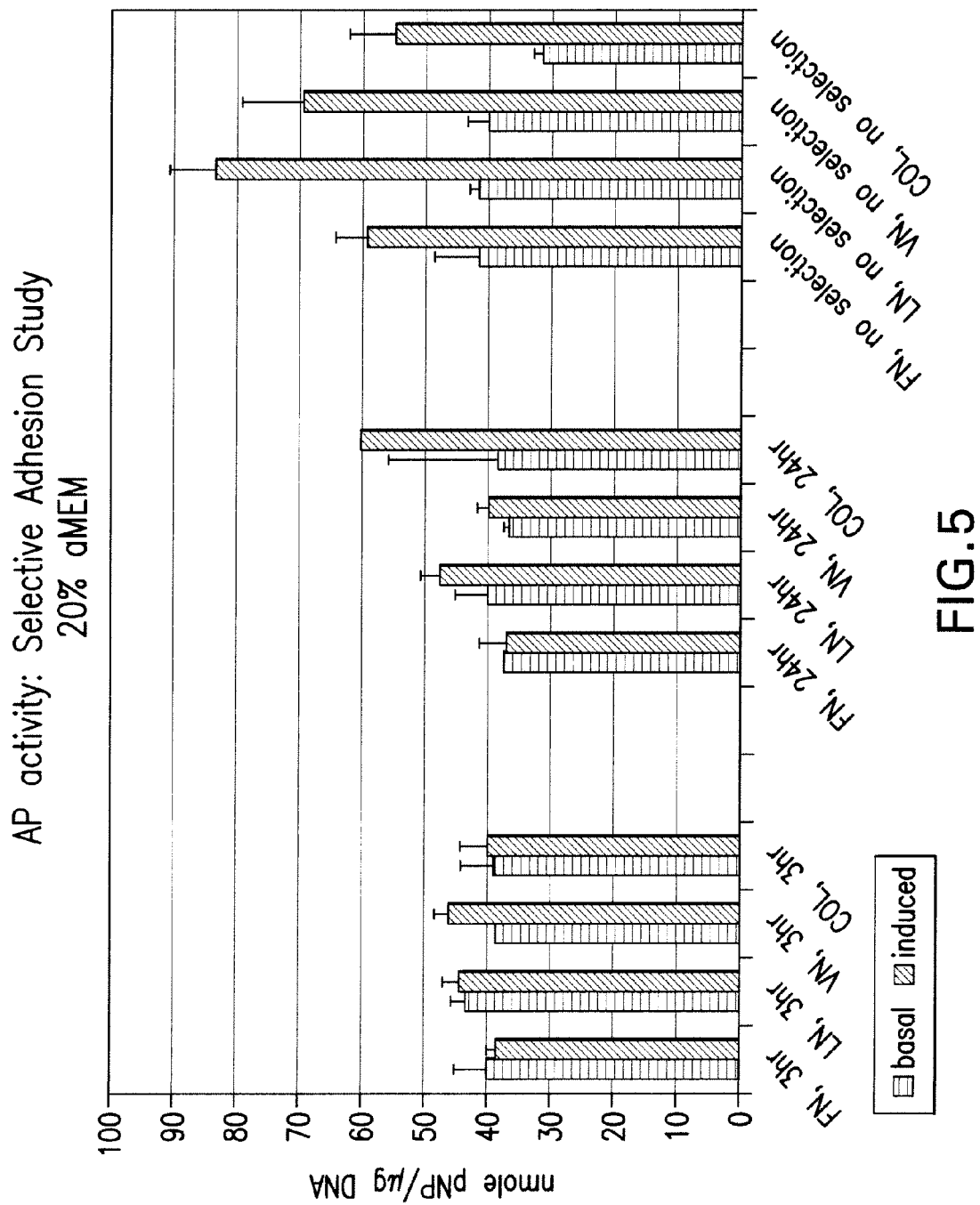

FIG. 5: Alkaline Phosphatase (AP) activity of OPACs obtained by selective adhesion.

Figure 6:
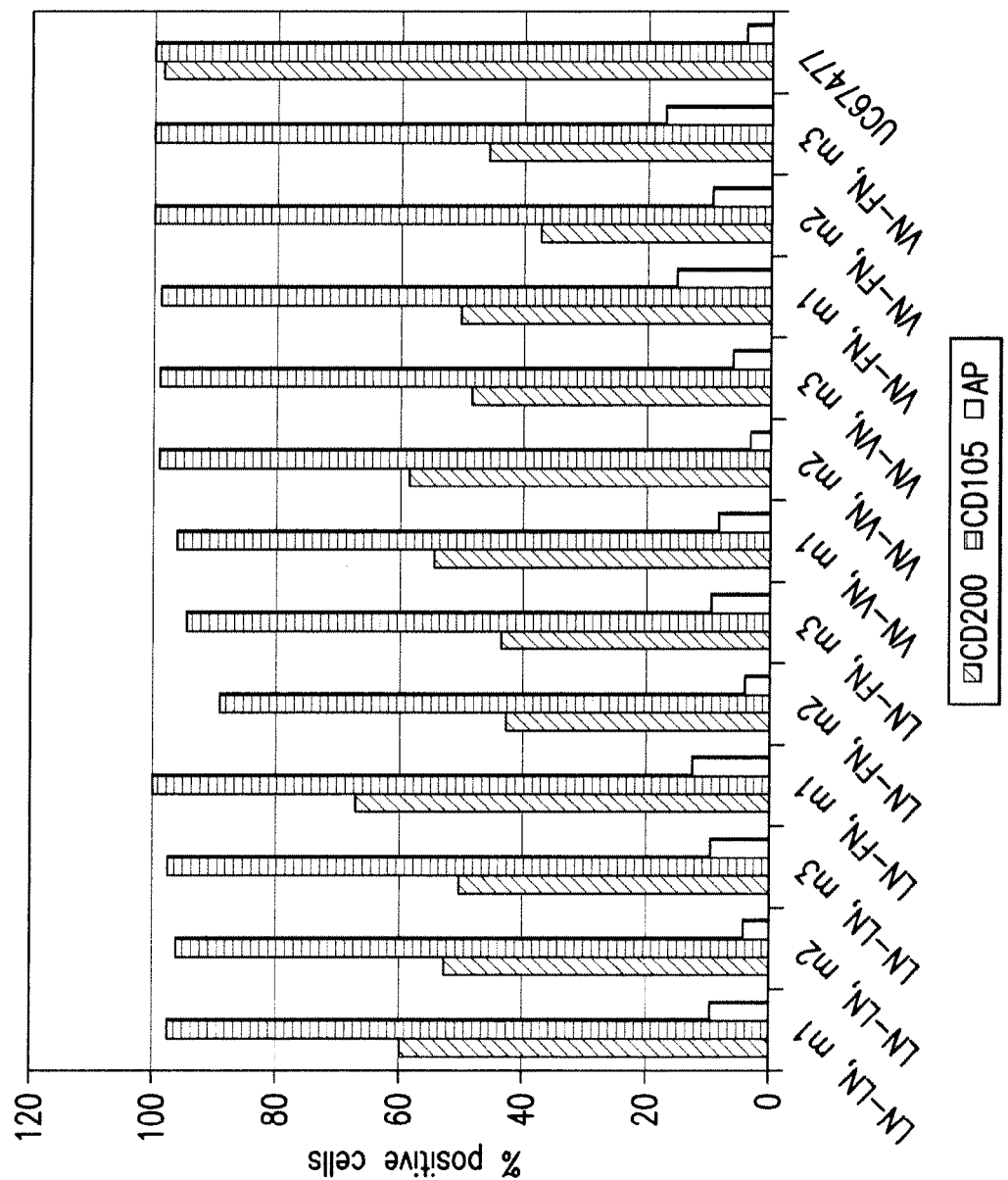

FIG. 6: Immunophenotype of culture expanded OPACs.

Figure 7:
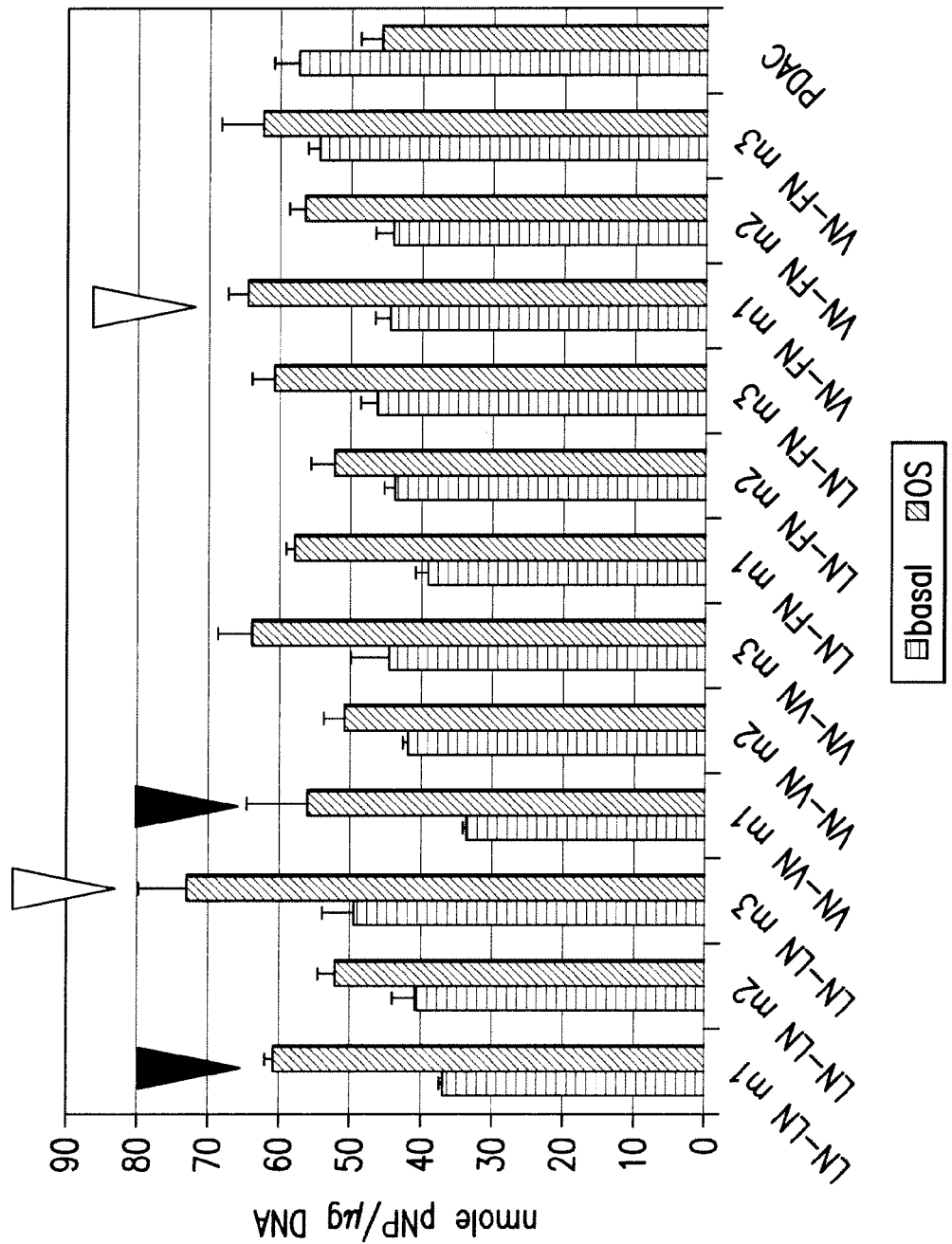

FIG. 7: Alkaline phosphatase activity of culture expanded OPACs. Basal: growth medium. OS: osteogenic medium. m1: medium 1—20% FBS (Hyclone)/α-MEM comprising 100 units/mL penicillin, 100 μg/mL streptomycin, 2 mM L-glutamine. m2: medium 2—Mesenchymal Stem Cell Growth Medium (MSCGM; Lonza). m3: medium 3—10% FBS (Mesenchymal Stem Cell Qualified FBS, Stem Cell Technologies)/α-MEM comprising 100 Units/mL, 100 μg/mL streptomycin and 2 mM L-glutamine.

Figure 8:
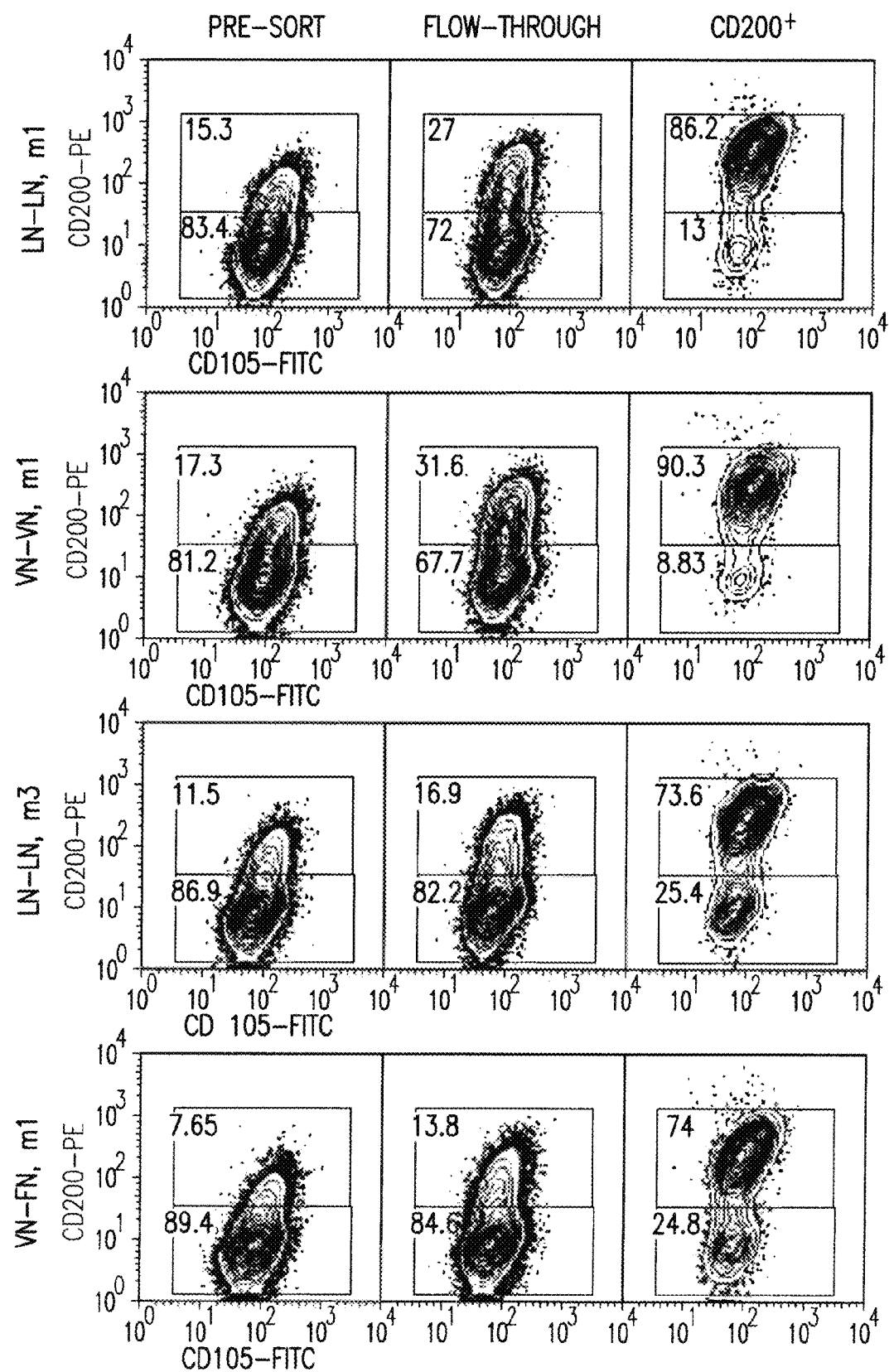

FIG. 8: Immunophenotype (CD200, CD105) of OPACs after magnetic activated cell sorting. LN: laminin. VN: vitronectin. FN: fibronectin. m1: medium 1—20% FBS (Hyclone)/α-MEM comprising 100 units/mL penicillin, 100 μg/mL streptomycin, 2 mM L-glutamine. m3: medium 3—10% FBS (Mesenchymal Stem Cell Qualified FBS, Stem Cell Technologies)/α-MEM comprising 100 Units/mL, 100 μg/mL streptomycin and 2 mM L-glutamine.

Figure 9:
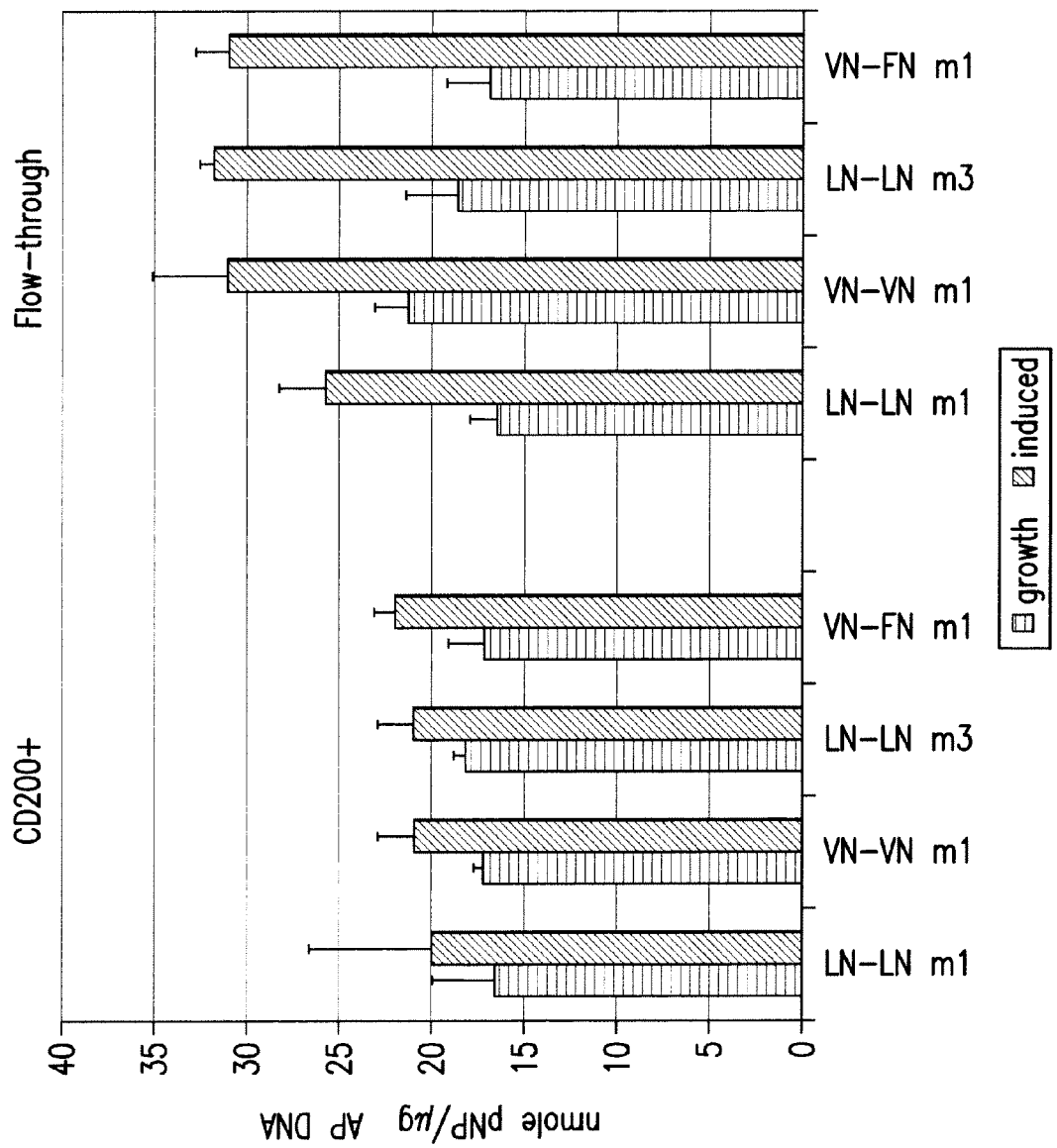

FIG. 9: Alkaline phosphatase activity of a $CD200^+$ population and a flow-through fraction (comprising $CD200^-$ cells) after magnetic activated cell sorting. LN: laminin. VN: vitronectin. FN: fibronectin. m1: medium 1—20% FBS (Hyclone)/α-MEM comprising 100 units/mL penicillin, 100 μg/mL streptomycin, 2 mM L-glutamine. m3: medium 3—10% FBS (Mesenchymal Stem Cell Qualified FBS, Stem Cell Technologies)/α-MEM comprising 100 Units/mL, 100 μg/mL streptomycin and 2 mM L-glutamine. Basal: AP expression in growth medium. Induced: AP expression in osteogenic medium.

Figure 10:
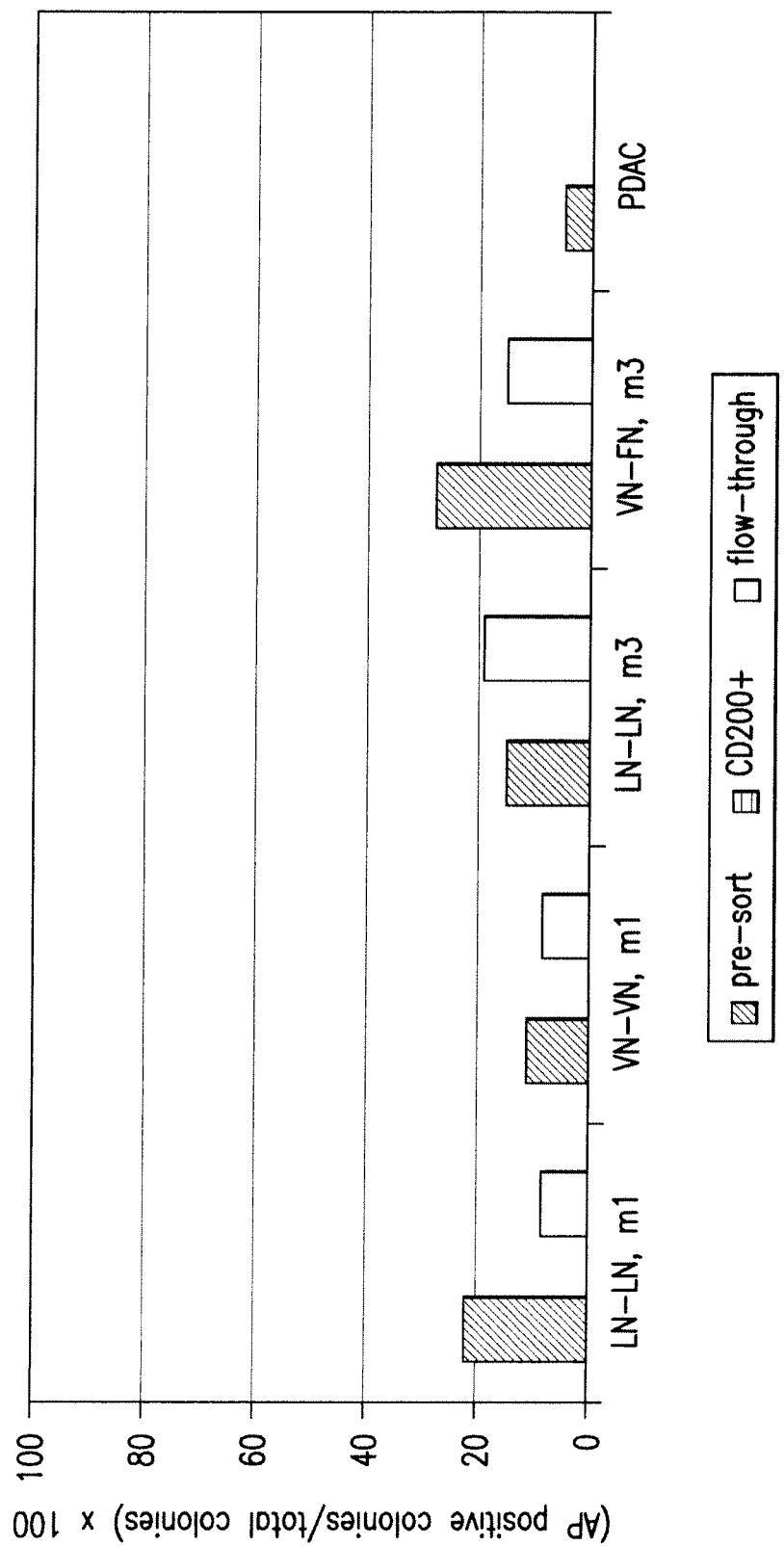

FIG. 10: Colony forming unit-alkaline phosphatase (CFU-AP) activity of populations of chorion derived stem cells after magnetic activated cell sorting. LN: laminin. VN: vitronectin. FN: fibronectin. m1: medium 1—20% FBS (Hyclone)/α-MEM comprising 100 units/mL penicillin, 100 μg/mL streptomycin, 2 mM L-glutamine. m3: medium 3—10% FBS (Mesenchymal Stem Cell Qualified FBS, Stem Cell Technologies)/α-MEM comprising 100 Units/mL, 100 μg/mL streptomycin and 2 mM L-glutamine. $CD200^+$ condition is substantially zero for AP expression.

Figure 11:
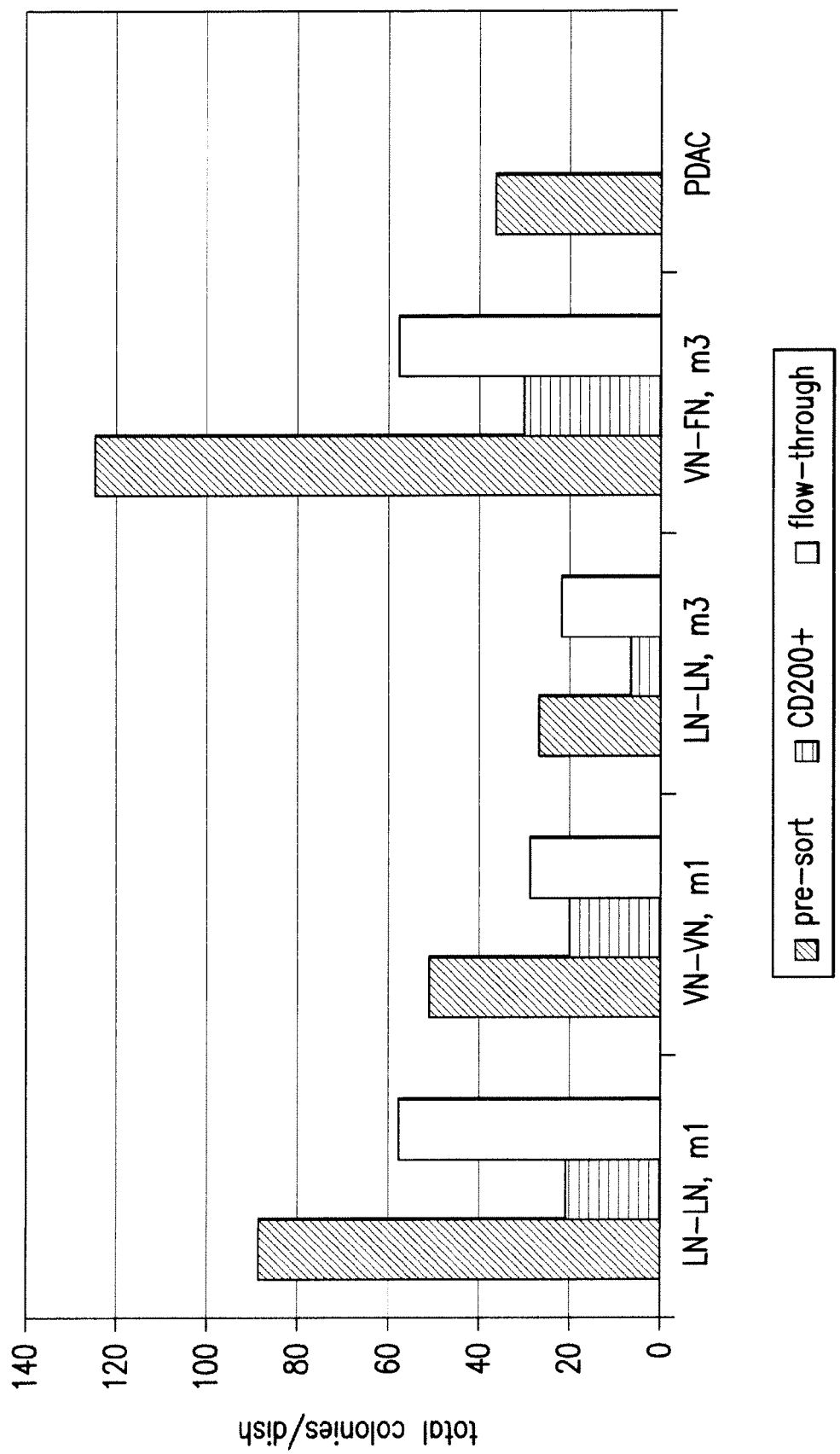

FIG. 11: Total colony formation of fractions of OPACs after magnetic activated cell sorting. FN: fibronectin. m1: medium 1—20% FBS (Hyclone)/α-MEM comprising 100 units/mL penicillin, 100 μg/mL streptomycin, 2 mM L-glutamine. m3: medium 3—10% FBS (Mesenchymal Stem Cell Qualified FBS, Stem Cell Technologies)/α-MEM comprising 100 Units/mL, 100 μg/mL streptomycin and 2 mM L-glutamine. PDAC: $CD10^+$, $CD34^-$, $CD105^+$, $CD200^+$ tissue culture plastic-adherent placental multipotent cells.

Figure 12:
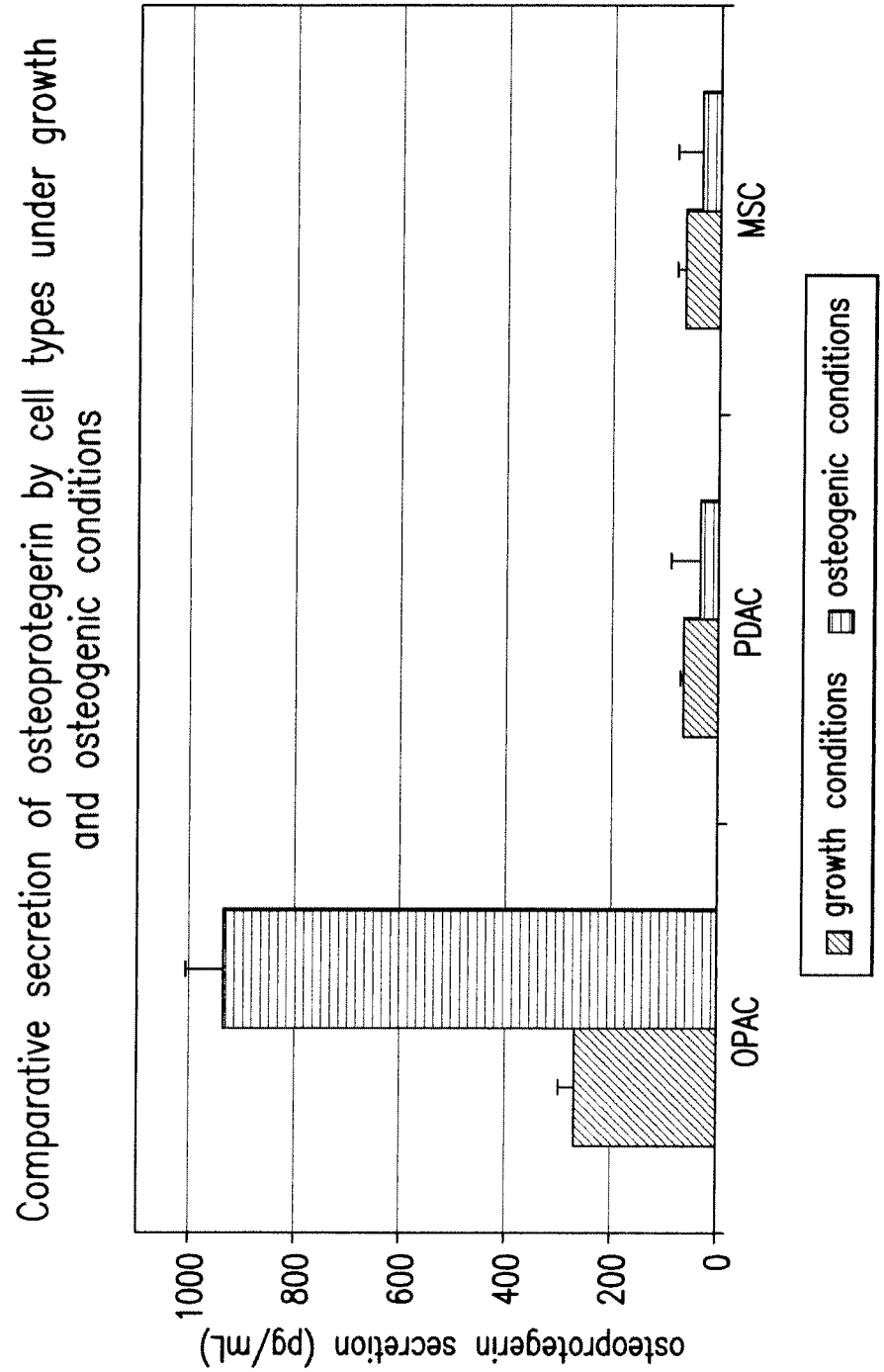

FIG. 12: Inducible osteoprotegerin secretion by OPACs after osteogenic stimulation.

FIG. 13: List of secreted proteins identified in OPACs, PDACs™, MSCs, and fibroblasts using RayBiotech 507 protein RayBio® Biotin Label-based Antibody Array. Protein expression is classified as + (low), ++ (medium), and +++ (high) compared to an internal positive control. The implication of the protein in bone formation (↑) or resorption (↓) is indicated.

Figure 14:
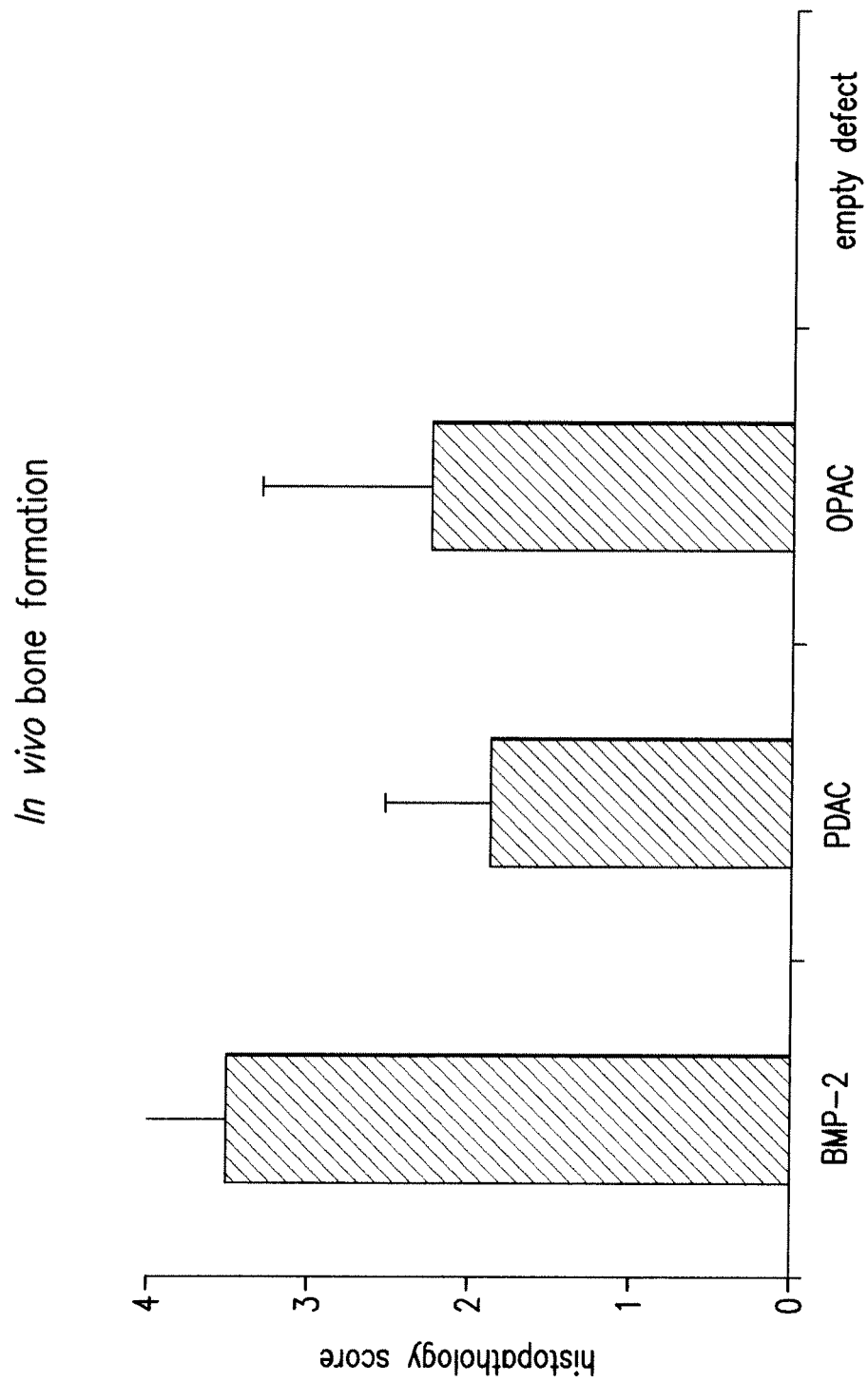

FIG. 14: Mean amount of osseous tissue formation by treatment group; scored as 0-4, with 4 as the largest amount.

Figure 15:
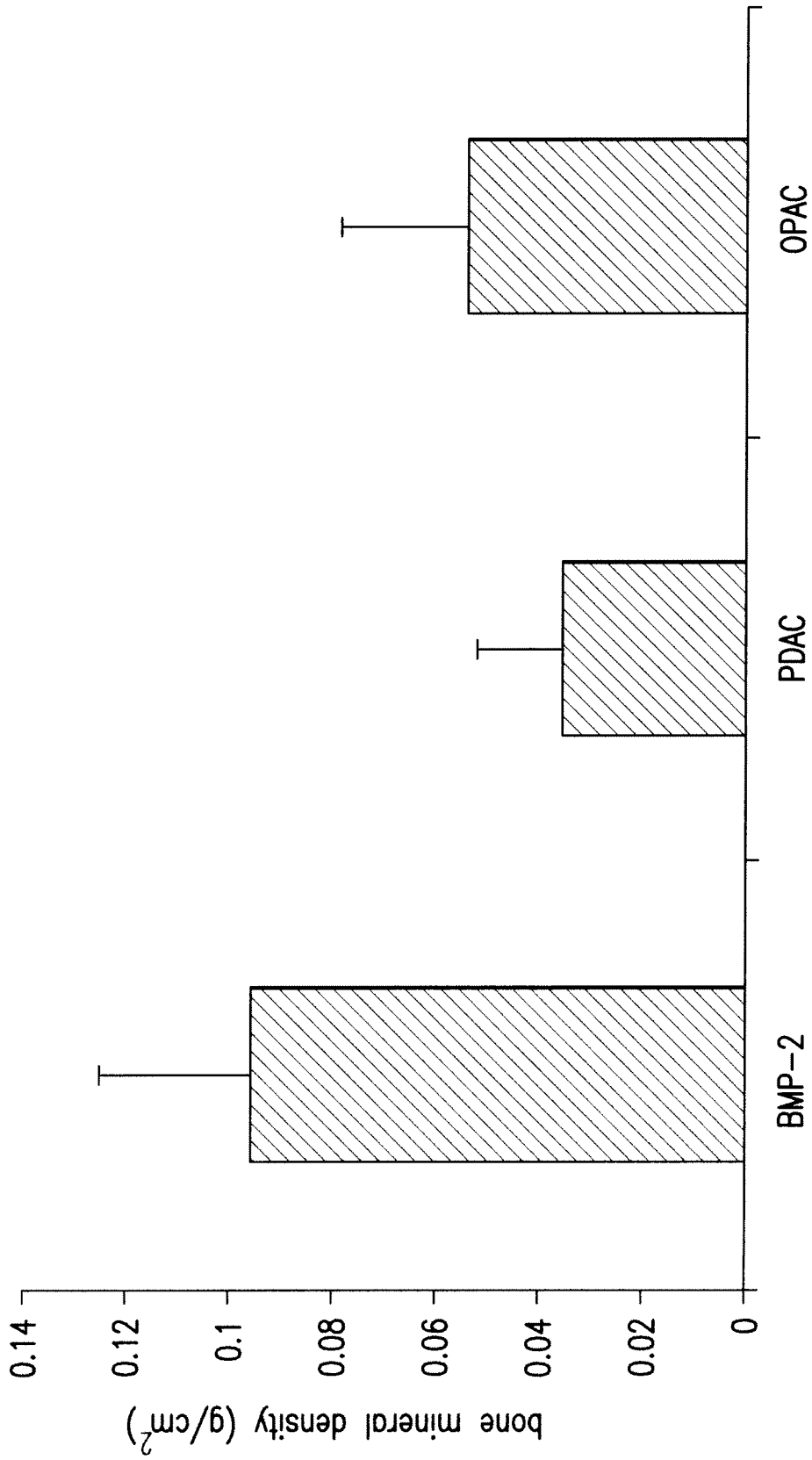

FIG. 15: Bone mineral density of cranial defect site by treatment group.

Figure 16:
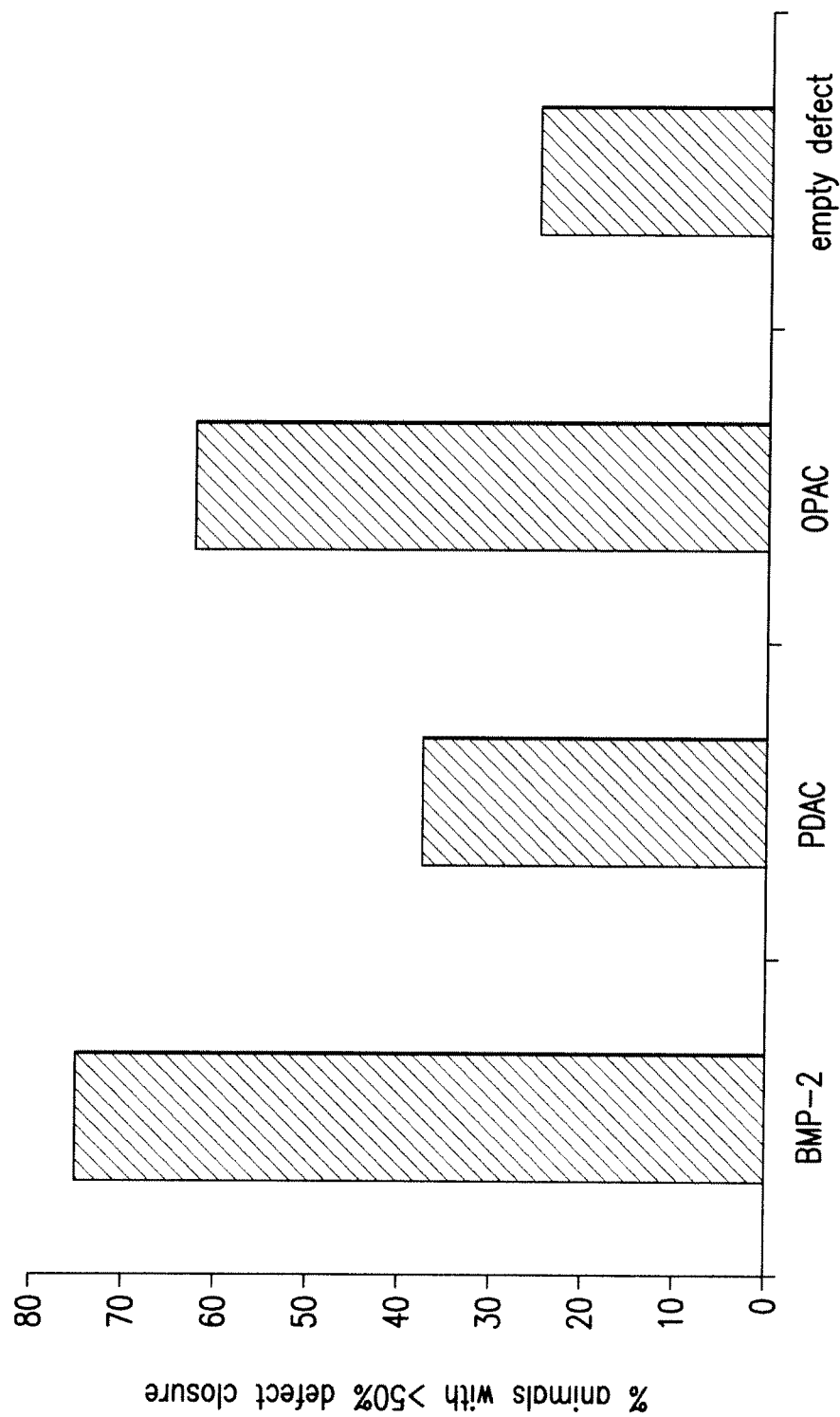

FIG. 16: Distribution of animals with >50% defect closure as determined by measurement of residual defect from X-ray scans at the time of sacrifice.

Figure 17:
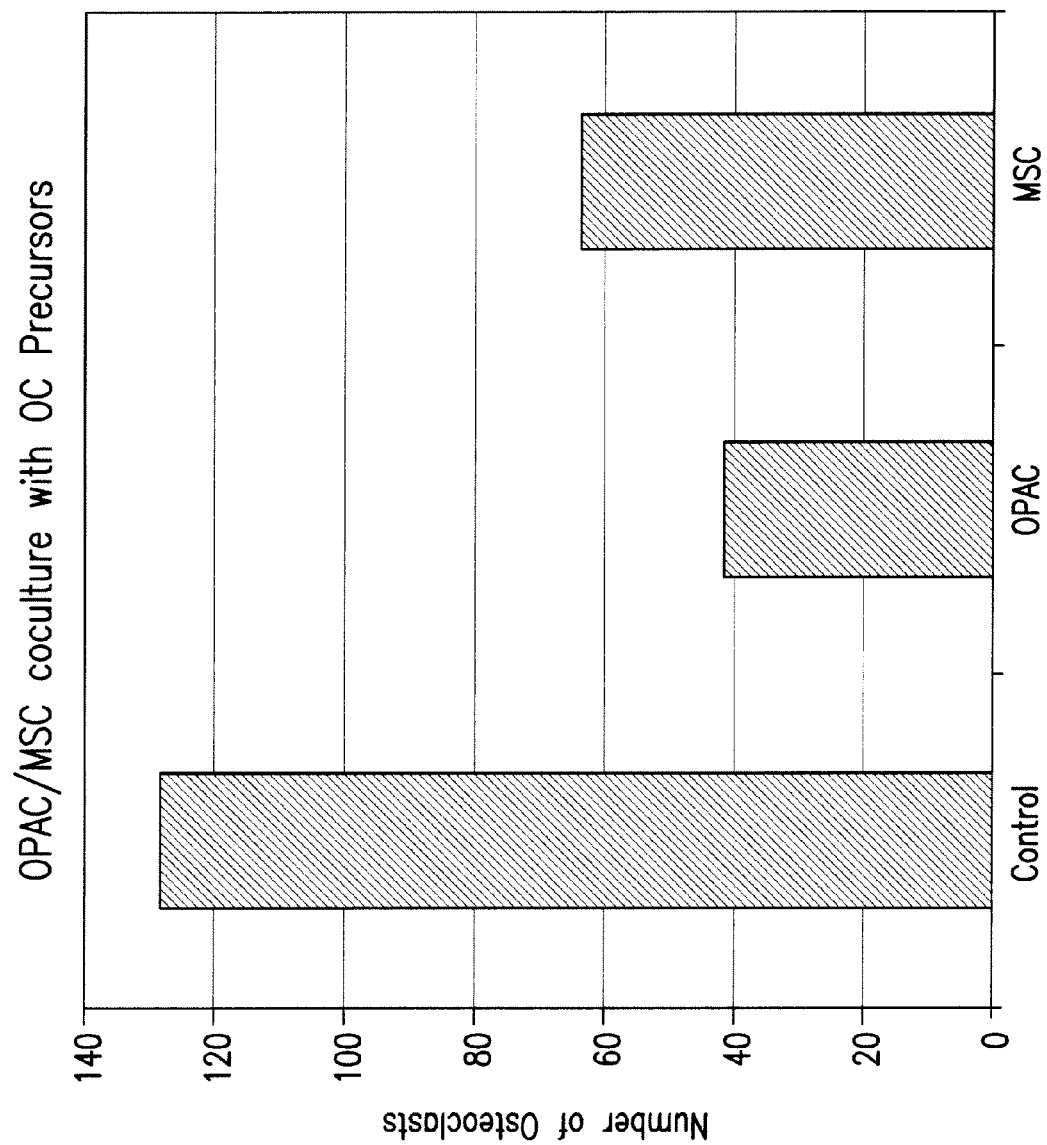

FIG. 17: Effects of OPACs and MSCs on osteoclastic differentiation. OC: osteoclast. control: osteoclasts without OPACs or MSCs.

Figure 18:
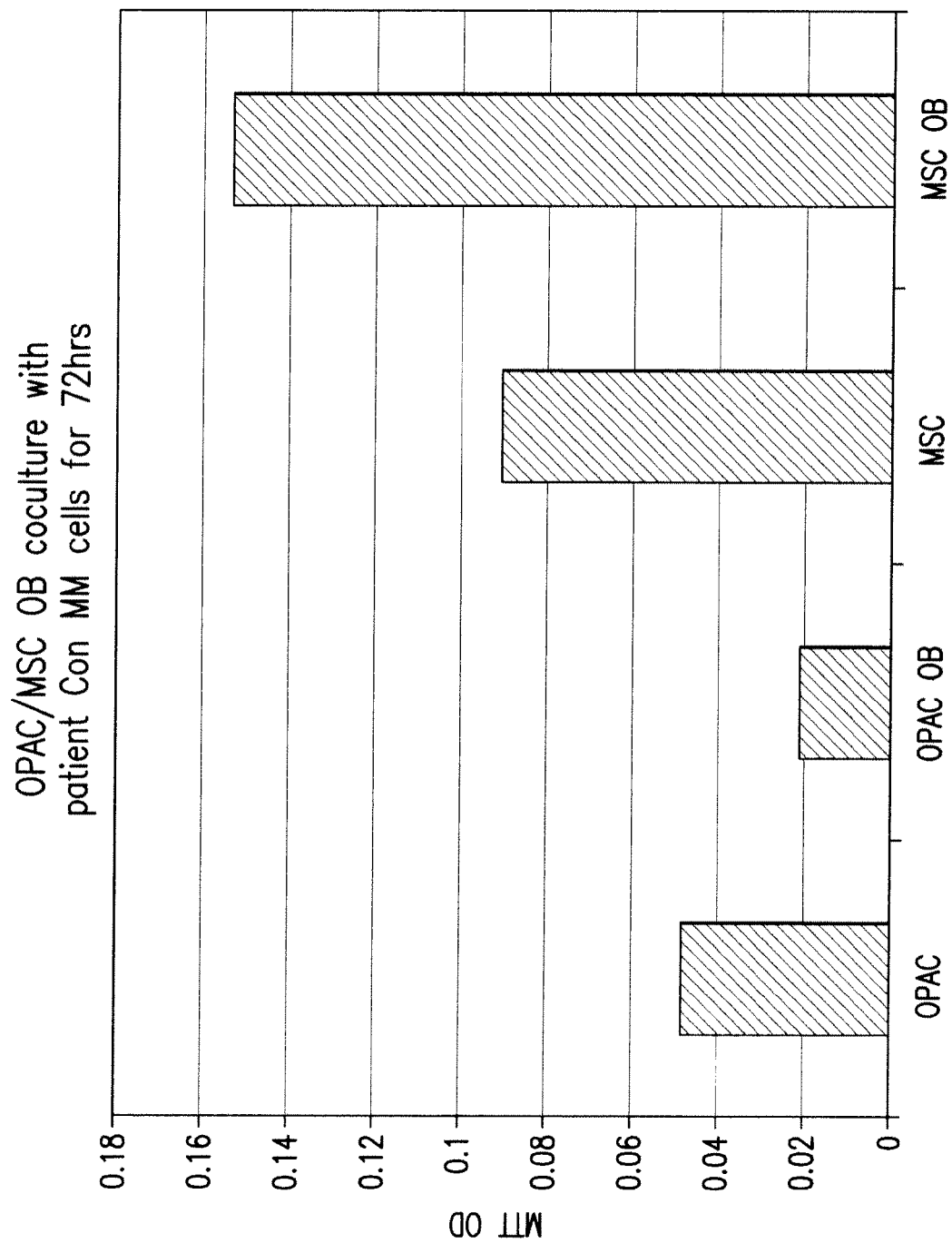

FIG. 18: Effect of OPACs and MSCs on the proliferation of multiple myeloma cells. OB: osteoblasts or osteoblast-like cells obtained from MSCs or PDACs under osteogenic conditions. MTT OD: optical density in MTT assay; higher values indicate a higher degree of multiple myeloma cell survival. Con MM: Multiple myeloma cells from 27 human multiple myeloma patients.

Figure 19:
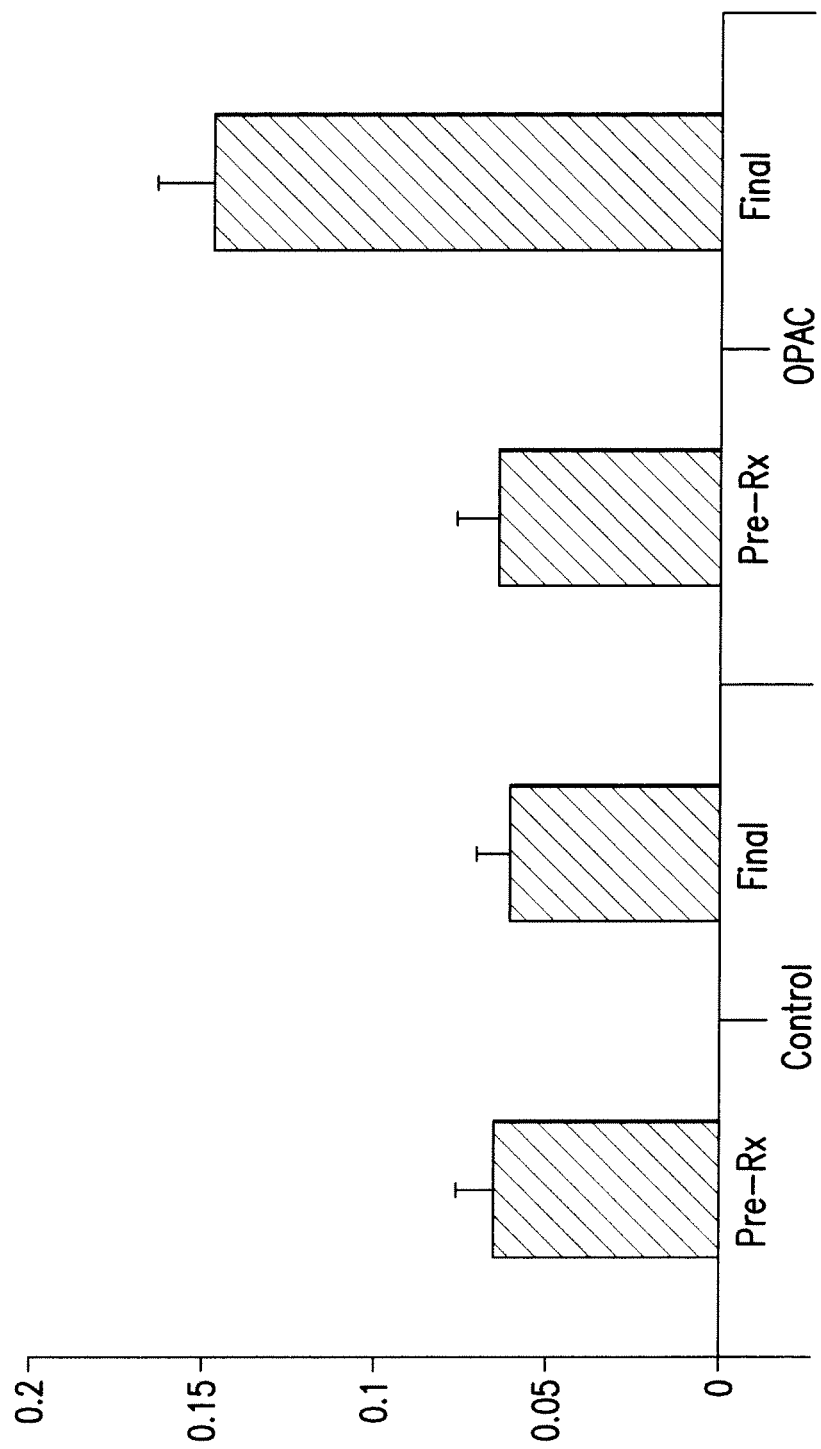

FIG. 19: Effect of OPACs on bone mineral density in primary myelomatous SCID-rab mice. Control: PBS only. Pre-Rx: bone mineral density (BMD) prior to administration of OPACs. Final: Bone mineral density after 8-16 weeks post-injection. Changes in the bone mineral density (BMD) of the implanted bones were determined using a PIXImus DEXA (GE Medical Systems Lunar, Madison, Wis.)

Figure 20:
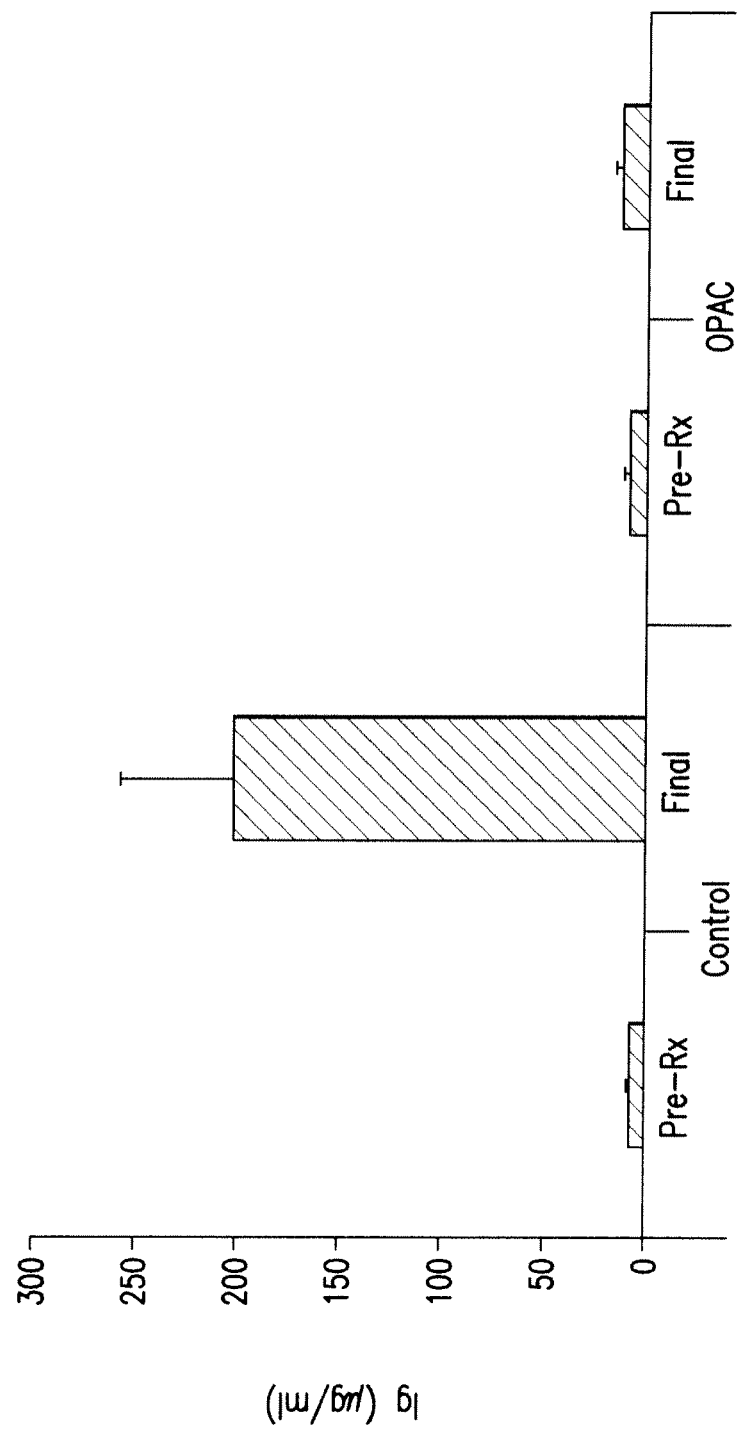

FIG. 20: Effect of OPACs on human immunoglobulin (hIg) levels in primary myelomatous mice. Ig: Human immunoglobulin in mouse sera.

Figure 21:
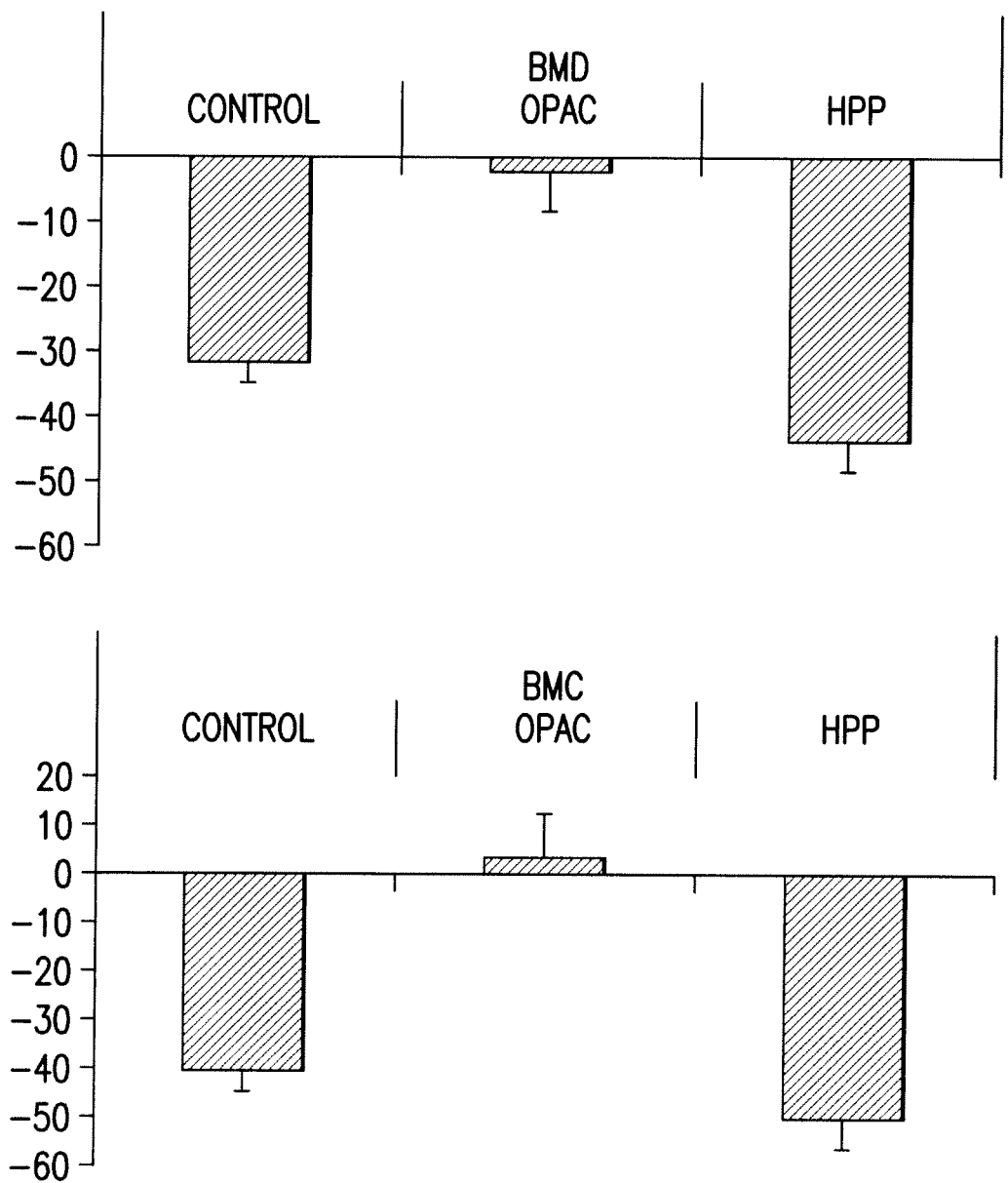

FIG. 21: Effect of OPACs on bone mass in primary myelomatous SCID-rab mice. BMD: bone mineral density. BMC: bone mineral content.

5. DETAILED DESCRIPTION

5.1 Osteogenic Placental Adherent Cells (OPACs)

5.1.1 Characteristics

5.1.1.1 Physical and Morphological Characteristics

The osteogenic placental adherent cells (OPACs) provided herein, when cultured in primary cultures or in cell culture, adhere to the tissue culture substrate, e.g., tissue culture container surface (e.g., tissue culture plastic). The OPACs in culture assume a generally fibroblastoid, stellate appearance, with a number of cytoplasmic processes extending from the central cell body. The OPACs are, however, morphologically distinguishable from fibroblasts cultured under the same conditions, as the OPACs generally exhibit a greater number of such processes than do fibroblasts. Morphologically, OPACs are also distinguishable from hematopoietic stem cells, which generally assume a more rounded, or cobblestone, morphology in culture.

5.1.1.2 Cell Surface, Molecular and Genetic Markers

In one embodiment, provided herein is an isolated OPAC (osteogenic placental adherent cell), i.e., an isolated cell that is adherent, osteogenic, and isolated from chorion. In one embodiment, the OPACs are not isolated from the chorionic skirt (laeve). OPACs provided herein, and populations of OPACs, express a plurality of cellular and genetic markers that can be used to identify and/or isolate the OPACs, or populations of cells that comprise the OPACs. The OPACs, and cell populations comprising OPACs provided herein, include OPACs and OPACs-containing cell populations obtained directly from the chorion, e.g., primary cultures.

OPAC populations also include populations of, e.g., two or more, OPACs in culture, OPACs in single-cell suspension, and a population in a container, e.g., a bag. In a specific embodiment, a population of OPACs is a plurality of OPACs in cell culture. OPACs are not trophoblasts, cytotrophoblasts, embryonic stem cells, or embryonic germ cells as those cells are known an understood in the art.

Provided herein is an isolated OPAC, where the OPAC is CD200⁻ or CD200$^{dim}$. In a specific embodiment, an OPAC is osteogenic. In a specific embodiment, an OPAC is positive for secretion of osteoprotegerin (OPG; see, e.g., GenBank Accession No. AAB53709). Osteoprotegerin is an osteoblast-secreted decoy receptor that specifically binds to osteoclast differentiation factor and inhibits osteoclast maturation. Thus, OPACs promote bone formation and reduce osteoclast-mediated bone loss. In another specific embodiment, an OPAC is negative for expression of RANKL (Receptor Activator of Nuclear Factor κB). RANKL is a protein that activates osteoclasts, which are involved in bone resorption. Thus, OPACs do not to promote bone resorption. In another specific embodiment, an OPAC is CD200⁻ or CD200$^{dim}$, and CD105⁺. In another specific embodiment, an OPAC is negative for expression of α-smooth muscle actin, e.g., as determined by immunofluorescence staining. It is noted that other populations of cells from placenta, e.g., the cells described in U.S. Patent Application Publication No. 2005/0058631, are positive for α-smooth muscle actin. In another specific embodiment, an OPAC is one or more of negative for expression of α-smooth muscle actin, negative for expression of RANKL, or positive for expression of NG2 (neural/glial cell 2 chondroitin sulfate proteoglycan). In another specific embodiment, an OPAC is negative for expression of α-smooth muscle actin, negative for expression of RANKL, positive for expression of NG2, and positive for secretion of osteoprotegerin. In another specific embodiment, an OPAC exhibits inducible alkaline phosphatase activity. In a more specific embodiment, an OPAC is CD200⁻ or CD200$^{dim}$, and CD105⁺, and is one or more of negative for expression of α-smooth muscle actin, negative for expression of RANKL, positive for expression of NG2, positive for expression of osteoprotegerin, or exhibits inducible alkaline phosphatase activity. In another more specific embodiment, an OPAC is CD200⁻ or CD200$^{dim}$, and CD105⁺, and also negative for expression of α-smooth muscle actin, negative for expression of RANKL, positive for expression of NG2, positive for expression of osteoprotegerin, and exhibits inducible alkaline phosphatase activity. The lack of expression, or the low expression, of CD200 by OPACs distinguishes OPACs from other tissue culture plastic-adherent placenta-derived multipotent cells, e.g., PDACs™, e.g., the placental multipotent cells described in Edinger et al., U.S. Patent Application Publication No. 2007/0275362.

In another specific embodiment, an OPAC is SSEA3⁺ or SSEA4⁺. In a more specific embodiment, an OPAC is SSEA3⁺ and SSEA4⁺. In another more specific embodiment, an OPAC is CD200⁻ or CD200$^{dim}$, and CD105⁺, SSEA3⁺, and also negative for expression of α-smooth muscle actin, negative for expression of RANKL, positive for expression of NG2, positive for expression of osteoprotegerin, and/or exhibits inducible alkaline phosphatase activity. In another more specific embodiment, an OPAC is CD200⁻ or CD200$^{dim}$, and CD105⁺, SSEA4⁺, and is also negative for expression of α-smooth muscle actin, negative for expression of RANKL, positive for expression of NG2, positive for expression of osteoprotegerin or exhibits inducible alkaline phosphatase activity. In a more specific embodiment, an OPAC is CD200⁻ or CD200$^{dim}$, CD105⁺, SSEA3⁺, SSEA4⁺, and is also negative for expression of α-smooth muscle actin, negative for expression of RANKL, positive for expression of NG2, positive for expression of osteoprotegerin or exhibits inducible alkaline phosphatase activity. The expression of SSEA3 and SSEA4 by OPACs serves to distinguish OPACs from other placenta-derived cells, e.g., tissue culture plastic adherent placental stem cells described in Hariri, U.S. Pat. No. 7,468,276.

In certain embodiments, an OPAC facilitates formation of a mineralized matrix in a population of placental cells when said population is cultured under conditions that allow the formation of a mineralized matrix.

Also provided herein are populations of cells comprising OPACs, wherein the population of cells is CD200⁻ or CD200$^{dim}$. Thus, in one embodiment, provided herein is an isolated population of cells comprising OPACs, wherein said population of cells is not isolated from chorionic skirt (laeve), and wherein said population of cells is CD200⁻ or CD200$^{dim}$. In a specific embodiment, the population of cells consists essentially of OPACs. In a specific embodiment, said population of cells is osteogenic. In another specific embodiment, said population of cells is CD200⁻ and CD105⁺ as detected by flow cytometry. In another specific embodiment, said population of cells is CD200$^{dim}$ and CD105⁺ as detected by flow cytometry. In another specific embodiment, said population of cells is negative for expression of α-smooth muscle actin, negative for expression of RANKL, positive for expression of NG2, and/or positive for secretion of osteoprotegerin. In another embodiment, said population of cells is negative for expression of α-smooth muscle actin, negative for expression of RANKL, positive for expression of NG2, and positive for secretion of osteoprotegerin. In another specific embodiment, said population of cells exhibits inducible alkaline phosphatase activity. In a more specific embodiment, said population is CD200⁻, CD105⁺ or CD200$^{dim}$, CD105⁺ and is also one or more of negative for expression of α-smooth muscle actin, negative for expression of RANKL, positive for expression of NG2, positive for expression of osteoprotegerin or exhibits inducible alkaline phosphatase activity. In a more specific embodiment, said population of cells is CD200⁻, CD105⁺ or CD200$^{dim}$, CD105⁺; is negative for expression of α-smooth muscle actin, negative for expression of RANKL, positive for expression of NG2, positive for expression of osteoprotegerin; and exhibits inducible alkaline phosphatase activity.

In another specific embodiment, said population of cells is SSEA3⁺ or SSEA4⁺. In yet another embodiment, said population cells is SSEA3⁺ and SSEA4⁺. In yet another embodiment, said population of cells is CD200⁻ and/or CD200$^{dim}$, CD105⁺, CD105⁺, SSEA3⁺, and also negative for expression of α-smooth muscle actin, negative for expression of RANKL, positive for expression of NG2, positive for expression of osteoprotegerin or exhibits inducible alkaline phosphatase activity. In another more specific embodiment, said population of cells is CD200⁻ or CD200$^{dim}$, is CD105⁺ and SSEA4⁺, and is also negative for expression of α-smooth muscle actin, negative for expression of RANKL, positive for expression of NG2, positive for expression of osteoprotegerin or exhibits inducible alkaline phosphatase activity. In another more specific embodiment, said population of cells is CD200⁻ or CD200$^{dim}$; is CD105⁺, SSEA3⁺, SSEA4⁺, negative for expression of α-smooth muscle actin, negative for expression of RANKL, positive for expression of NG2, positive for expression of osteoprotegerin, and/or exhibits inducible alkaline phosphatase activity.

In specific embodiments, at least 20%, 30%, 40%, 50%, 60%, 70%, 80%, 90% or 95% of the cells in the population are CD200⁻.

Further provided herein is an isolated population of OPACs, wherein said population is produced by isolating chorionic tissue from a placenta, wherein said chorionic tissue is not chorionic skirt (laeve) tissue; digesting the isolated chorionic tissue with a tissue-disrupting enzyme to obtain a population of chorion cells comprising OPACs; and isolating said OPACs from said chorion cells. In a specific embodiment, the tissue-disrupting enzyme is trypsin, dispase or collagenase. In various embodiments, the chorionic stem cells, contained within a population of cells obtained from digesting chorionic tissue, are at least about 10%, 20%, 30%, 40%, 50%, 60%, 70%, 80%, 90%, 95%, 99% or at least 99.5% of said population of chorionic cells.

Isolated populations of cells comprising OPACs, e.g., populations of OPACs, are distinguishable from other cells, e.g., CD200⁺, non-dim, placenta-derived adherent cells (referred to herein as PDAC™s), as described, for example, in U.S. Pat. Nos. 7,468,276 and 7,255,879, and in U.S. Patent Publication No. 2007/02753621, the disclosures of which are hereby incorporated by reference in their entireties, e.g., as shown by gene profiling. PDACs™ are identified, e.g., as CD10⁺, CD34⁻, CD105⁺, CD200⁺, non-dim, cells from placenta or umbilical cord, which are adherent to tissue culture surfaces, e.g., tissue culture plastic. PDACs™ can be further characterized as being CD10⁺, CD34⁻, CD45⁻, CD90⁺, CD105⁺, and CD200⁺ cells from placenta or umbilical cord, which are adherent to tissue culture surfaces, e.g., tissue culture plastic. In a specific embodiment, the population of cells consists essentially of OPACs.

The OPACs described herein can be distinguished from PDACs™ on the basis of the expression of one or more genes, the expression of which, or the degree of expression of which, is specific to OPACs as compared to PDACs™. In one embodiment, for example, provided herein is a population of cells comprising OPACs, wherein said population of cells express one or more genes at a detectably higher level (e.g., at least a twofold higher level) than an equivalent number of adherent CD200⁺, non-dim, placental stem cells that are not trophoblasts or cytotrophoblasts (PDACs™), wherein said one or more genes comprise one or more, or all, of BMP6 (bone morphogenetic protein 6; see, e.g., GenBank Accession No. NM_001718), CDH11 (cadherin 11, type 2, osteoblast cadherin; see, e.g., GenBank Accession No. NM_001797), COL10A1 (collagen, type X, alpha 1; see, e.g., GenBank Accession No. NM_000493), COL14A1 (collagen, type XIV, alpha 1; see, e.g., GenBank Accession No. NM_021110), COL15A1 (collagen, type XV, alpha 1; see, e.g., GenBank Accession No. NM_001855), COL1A1 (collagen, type I, alpha 1; see, e.g., GenBank Accession No. NM_000088), COL1A2 (collagen, type I, alpha 2; see, e.g., GenBank Accession No. NM_000089), COL3A1 (collagen, type III, alpha 1; see, e.g., GenBank Accession No. NM_000090), COL4A3 (collagen, type IV, alpha 3; see, e.g., GenBank Accession No. NM_000091), COL5A1 (collagen, type V, alpha 1; see, e.g., GenBank Accession No. NM_000093), CSF3 (colony-stimulating factor 3 (granulocyte); see, e.g., GenBank Accession No. NM_000759), CTSK (cathepsin K; see, e.g., GenBank Accession No. NM_000396), IGF1R (insulin-like growth factor 1 receptor; see, e.g., GenBank Accession No. NM_000875), MINPP1 (multiple inositol polyphosphate histidine phosphatase 1; see, e.g., GenBank Accession No. NM_004897), MMP2 (matrix metalloprotease 2 (also known as gelatinase A, 72 kDa gelatinase, 72 kDa type IV collagenase); see, e.g., GenBank Accession No. NM_004530), MMP9 (matrix metallopeptidase 9 (also known as gelatinase B, 92 kDa gelatinase, 92 kDa type IV collagenase); see, e.g., GenBank Accession No. NM_004994), MSX1 (msh homeobox 1; see, e.g., GenBank Accession No. NM_002448), SMAD1 (SMAD family member 1; see, e.g., GenBank Accession No. NM_001003688), SMAD3 (SMAD family member 3; see, e.g., GenBank Accession No. NM_005902), TGFB3 (transforming growth factor, beta 3; see, e.g., GenBank Accession No. NM_003239), TGFBR1 (transforming growth factor, beta receptor 1; see, e.g., GenBank Accession No. NM_004612) and VEGFB (vascular endothelial growth factor B; see, e.g., GenBank Accession No. XM_001128909), when the OPACs and placental stem cells are grown under equivalent conditions, e.g., as assessed by Ct values from quantitative real-time PCR. In a specific embodiment, population of cells consists essentially of OPACs. In a specific embodiment, the population of cells consists essentially of OPACs.

In another embodiment, provided herein is a population of cells comprising OPACs, wherein said population of cells express one or more genes at a detectably higher level (e.g., at least a twofold higher level) than an equivalent number of adherent CD200⁺, non-dim, placental stem cells that are not trophoblasts or cytotrophoblasts, wherein said one or more genes comprise one or more, or all, of BMP3 (bone morphogenetic protein 3; see, e.g., GenBank Accession No. NM_001201), CDH11, COL10A1, COL14A1, COL15A1, DMP1 (dentin matrix acidic phosphoprotein 1; see, e.g., GenBank Accession No. NG_008988), DSPP (dentin sialophosphoprotein; see, e.g., GenBank Accession No. NM_014208), ENAM (enamelin; see, e.g., GenBank Accession No. NM_031889), FGFR2 (fibroblast growth factor receptor 2; see, e.g., GenBank Accession No. NM_000141), MMP10 (matrix metalloprotease 10 (stromelysin 2); see, e.g., GenBank Accession No. NM_002425), TGFB3, and/or TGFBR1 when said OPACs and said placental stem cells are cultured in growth medium, e.g., as assessed by Ct values from quantitative real-time PCR. In a specific embodiment, said growth medium is αMEM/20% Fetal Bovine Serum containing 100 units/mL penicillin, 100 µg/mL streptomycin and 2 mM L-glutamine. In a specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of adherent CD200⁺, non-dim, placental stem cells that are not trophoblasts or cytotrophoblasts, wherein said one or more genes comprise one or more, or all, of AMBN (ameloblastin (enamel matrix protein); see, e.g., GenBank Accession No. NM_031889), BMP2 (bone morphogenetic protein 2; see, e.g., GenBank Accession No. NM_001200), CALCR (calcitonin receptor; see, e.g., GenBank Accession No. NM_001742), CDH11, COL11A1 (collagen type XI, alpha 1; NM_001854), COL14A1, COL15A1, COL2A1 (collagen type II, alpha 1; see, e.g., GenBank Accession No. NM_001844), CSF2 (colony-stimulating factor 2; NM_000758), CSF3, DMP1, DSPP, ENAM, FGF3, GDF10 (growth differentiation factor 10; see, e.g., GenBank Accession No. NM_004962), IGF1 (insulin-like growth factor 1; see, e.g., GenBank Accession No. NM_000618), ITGA1 (integrin, alpha 1 (CD49); see, e.g., GenBank Accession No. NM_181501), ITGA2 (integrin, alpha 2 (CD49B); see, e.g., GenBank Accession No. NM_002203), MMP10, MMP8 (matrix metalloprotease 8 (neutrophil collagenase); see, e.g., GenBank Accession No.

NM_002424), MMP9, PDGFA (platelet-derived growth factor A; see, e.g., GenBank Accession No. XM_001126441), SMAD1, TGFB3, TGFBR1 and/or TGFBR2 (transforming growth factor beta, receptor 2; see, e.g., GenBank Accession No. NM_001024847) when said OPACs and said placental stem cells are cultured in osteogenic medium, e.g., as assessed by Ct values from quantitative real-time PCR. In a specific embodiment, said osteogenic medium is αMEM/20% Fetal Bovine Serum containing 100 units/mL penicillin, 100 µg/mL streptomycin, 2 mM L-glutamine, 50 µg/mL ascorbic acid, and 100 nM dexamethasone. In a specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of adherent CD200+, non-dim, placental stem cells that are not trophoblasts or cytotrophoblasts, wherein said one or more genes comprise one or more, or all, of CDH11, COL14A1, COL15A1, DMP1, DSPP, ENAM, MMP10, TGFB3 and/or TGFBR1 regardless of whether said OPACs and said placental stem cells are cultured in growth medium or osteogenic medium, e.g., as assessed by Ct values from quantitative real-time PCR. In a specific embodiment, the population of cells consists essentially of OPACs.

In another embodiment, provided herein is a population of cells comprising OPACs, wherein said population of cells, e.g., the OPACs, express one or more genes at a detectably lower level (e.g., at least a twofold lower level) than an equivalent number of adherent CD200+, non-dim, placental stem cells that are not trophoblasts or cytotrophoblasts, wherein said one or more genes comprise one or more, or all, of AHSG (alpha-2-HS-glycoprotein; see, e.g., GenBank Accession No. NM_001622), ALPL (alkaline phosphatase liver/bone/kidney; see, e.g., GenBank Accession No. NM_000478), EGF (epidermal growth factor; see, e.g., GenBank Accession No. NM_001963), FLT1 (fms-related tyrosine kinase 1 (vascular endothelial growth factor/vascular permeability factor receptor); see, e.g., GenBank Accession No. NM_002019), IGF2, ITGA2, ITGAM (integrin, alpha M (complement component 3 receptor 3 subunit); see, e.g., GenBank Accession No. NM_000632), SCARB1 (scavenger receptor class B, member 1; see, e.g., GenBank Accession No. NM_005505), SOX9 (SRY (sex determining region Y)-box 9; see, e.g., GenBank Accession No. NM_000346), TNF, TWIST1 (Twist homolog 1; formerly blepharophimosis, epicanthus inversus and ptosis 3, acrocephalosyndactyly 3; see, e.g., GenBank Accession No. NM_000474), VCAM1 (vascular cell adhesion molecule 1; see, e.g., GenBank Accession No. NM_001078) and/or VDR when said OPACs and said placental stem cells are cultured in growth medium, e.g., as assessed by Ct values from quantitative real-time PCR. In a specific embodiment, said growth medium is osteogenic medium is αMEM/20% Fetal Bovine Serum comprising 100 units/mL penicillin, 100 µg/mL streptomycin and 2 mM L-glutamine. In a specific embodiment, the population of cells consists essentially of OPACs.

In another embodiment, provided herein is a population of cells comprising OPACs, wherein said population of cells, e.g., the OPACs, express one or more genes at a detectably lower level (e.g., at least a twofold lower level) than an equivalent number of adherent CD200+, non-dim, placental stem cells that are not trophoblasts or cytotrophoblasts, wherein said one or more genes comprise one or more, or all, of BGN, COL11A1, COMP (cartilage oligomeric matrix protein), FGF1 and/or VCAM1 when said OPACs and said placental stem cells are cultured in osteogenic medium, e.g., as assessed by Ct values from quantitative real-time PCR. In a specific embodiment, said osteogenic medium is osteogenic medium is αMEM/20% Fetal Bovine Serum comprising 100 units/mL penicillin, 100 µg/mL streptomycin, 2 mM L-glutamine, 50 µg/mL ascorbic acid, and 100 nM dexamethasone. In a specific embodiment, the population of cells consists essentially of OPACs.

In another embodiment, provided herein is a population of cells comprising OPACs, wherein said population of cells, e.g., the OPACs, express VCAM1 at a detectably lower level (e.g., at least a twofold lower level) than an equivalent number of adherent CD200+, non-dim, placental stem cells that are not trophoblasts or cytotrophoblasts, regardless of whether said OPACs and said placental stem cells are cultured in growth medium or osteogenic medium, e.g., as assessed by Ct values from quantitative real-time PCR. In a specific embodiment, the population of cells consists essentially of OPACs.

Gene profiling also shows that isolated populations of cells comprising OPACs, e.g., populations of OPACs, are distinguishable from mesenchymal stem cells, e.g., bone-marrow derived mesenchymal stem cells. In one embodiment, for example, provided herein is a population of cells comprising OPACs, wherein said population of cells, e.g., the OPACs, express one or more genes at a detectably higher level (e.g., at least a twofold higher level) than an equivalent number of bone marrow-derived mesenchymal stem cells, wherein said one or more genes comprise one or more, or all, of BMP4, BMP6, CD36, CDH11, COL14A1, COL15A1, COL1A1, COL3A1, COL5A1, CSF2, CTSK, FGF2, FGFR1, FLT1, ITGA1, MINPP1, MMP9, MSX1, PDGFA, SERPINH1, TGFB3 and TGFBR1, when the OPACs and stem cells are grown under equivalent conditions, e.g., as assessed by Ct values from quantitative real-time PCR. In a specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of bone marrow-derived mesenchymal stem cells, wherein said one or more genes comprise one or more, or all, of BMP4, CALCR, CD36, CDH11, COL12A1, COL14A1, COL15A1, COL3A1, COL5A1, DMP1, DSPP, FLT1, MSX1, PDGFA, TGFB3, TGFBR1 and/or TUFT1, when the OPACs and mesenchymal stem cells are cultured in growth medium, e.g., as assessed by Ct values from quantitative real-time PCR. In a specific embodiment, said growth medium is osteogenic medium is αMEM/20% Fetal Bovine Serum comprising 100 units/mL penicillin, 100 µg/mL streptomycin and 2 mM L-glutamine. In a specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of bone marrow-derived mesenchymal stem cells, wherein said one or more genes comprise one or more, or all, of AMBN, CALCR, COL14A1, COL15A1, CSF3, DMP1, DSPP, ITGA1, ITGA2, MMP10, MMP9, MSX1, PDGFA, TGFB1, TGFB3, TGFBR1 and/or TGFBR2, when the OPACs and mesenchymal stem cells are cultured in osteogenic medium, e.g., as assessed by Ct values from quantitative real-time PCR. In a specific embodiment, said osteogenic medium is osteogenic medium is αMEM/20% Fetal Bovine Serum comprising 100 units/mL penicillin, 100 µg/mL streptomycin, 2 mM L-glutamine, 50 µg/mL ascorbic acid, and 100 nM dexamethasone. In a specific embodiment, the population of cells consists essentially of OPACs. In a specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of bone marrow-derived mesenchymal stem cells, wherein said one or more genes comprise one or more, or all, of CALCR, COL14A1, COL15A1, DMP1, DSPP, MSX1, PDGFA, TGFB3 and/or TGFBR1 regardless of whether said OPACs and said mesenchymal stem cells are cultured in growth medium or osteogenic medium, e.g., as assessed by Ct values from quantitative real-time PCR. In another specific embodiment, the population of cells consists essentially of OPACs.

In another embodiment, provided herein is a population of cells comprising OPACs, wherein said population of cells, e.g., the OPACs, express one or more genes at a detectably lower level (e.g., at least a twofold lower level) than an equivalent number of bone marrow-derived mesenchymal stem cells, wherein said one or more genes comprise one or more, or all, of ALPL, BGLAP, IGF2, ITGA2, ITGAM, SCARB1 and/or SOX1, when the OPACs and mesenchymal stem cells are cultured in growth medium, e.g., as assessed by Ct values from quantitative real-time PCR. In a specific embodiment, said growth medium is osteogenic medium is αMEM/20% Fetal Bovine Serum comprising 100 units/mL penicillin, 100 µg/mL streptomycin and 2 mM L-glutamine. In another embodiment, provided herein is a population of cells comprising OPACs, wherein said population of cells express one or more genes at a detectably lower level (e.g., at least a twofold lower level) than an equivalent number of bone marrow-derived mesenchymal stem cells, wherein said one or more genes comprise one or more, or all, of AHSG, ALPL, BGLAP, BGN, BMP3, BMP5, CD36, COL10A1, COL11A1, COL12A1, COL2A1, COL4A3, COMP, EGF, FGF1, FGFR2, IGF2, MMP8, PHEX, RUNX2 (runt-related transcription factor 2; see, e.g., GenBank Accession No. NM_001015051), SCARB1, SOX1, VCAM1 and/or VEGFB, when the OPACs and mesenchymal stem cells are cultured in osteogenic medium, e.g., as assessed by Ct values from quantitative real-time PCR. In a specific embodiment, said osteogenic medium is osteogenic medium is αMEM/20% Fetal Bovine Serum comprising 100 units/mL penicillin, 100 µg/mL streptomycin, 2 mM L-glutamine, 50 µg/mL ascorbic acid, and 100 nM dexamethasone. In a specific embodiment, the population of cells consists essentially of OPACs.

In another embodiment, provided herein is a population of cells comprising OPACs, wherein said population of cells, e.g., the OPACs, express one or more genes at a detectably lower level (e.g., at least a twofold lower level) than an equivalent number of bone marrow-derived mesenchymal stem cells, wherein said one or more genes comprise one or more, or all, of ALPL, BGLAP, IGF2, SCARB1 and/or SOX9, regardless of whether said OPACs and said mesenchymal stem cells are cultured in growth medium or osteogenic medium, e.g., as assessed by Ct values from quantitative real-time PCR. In another specific embodiment, the population of cells consists essentially of OPACs.

In another embodiment, provided herein is a population of cells comprising OPACs, wherein said population of cells, e.g., the OPACs, express one or more genes at a detectably higher level (e.g., at least a twofold higher level) than an equivalent number of adherent $CD200^+$, non-dim, placental stem cells, and an equivalent number of bone marrow-derived mesenchymal stem cells, wherein said one or more genes comprise one or more, or all, of COL14A1, COL14A2, DMP, DSPP, TGFB3 and/or TGFBR1, regardless of whether said OPACs, placental stem cells, and bone marrow-derived mesenchymal stem cells are cultured in growth medium or osteogenic medium, e.g., as assessed by Ct values from quantitative real-time PCR. In another specific embodiment, the population of cells consists essentially of OPACs.

Gene profiling also confirms that isolated populations of cells comprising OPACs, e.g., populations of OPACs, are distinguishable from human dermal fibroblast cells. In one embodiment, for example, provided herein is a population of cells comprising OPACs, wherein said population of cells express one or more genes at a detectably higher level (e.g., at least a twofold higher level) than an equivalent number of dermal fibroblast cells, wherein said one or more genes comprise one or more, or all, of BMP4, BMP6, CDH11, COL14A1, COL15A1, COL1A1, COL3A1, COL5A1, FLT1, IGF1R, ITGA1, MINPP1, PDGFA, SERPINH1, SMAD3, TGFB1, TGFB2, TGFB3, TGFBR1, TNF, TUFT1, VCAM1 and VEGFA, wherein the expression of these genes is higher in OPACs than in fibroblast cells, when the OPACs and fibroblasts are grown under equivalent conditions, e.g., as assessed by Ct values from quantitative real-time PCR. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold higher than an increase in said one or more of said genes in osteogenic medium, as compared to growth medium, in an equivalent number of adherent $CD200^+$, non-dim, placental stem cells, wherein said adherent $CD200^+$ placental stem cells are not trophoblasts or cytotrophoblasts, and wherein said one or more genes comprise one or more, or all, of BMP2, CSF3, ITGA2, MMP9, MMP10, and/or TGFB2. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold lower than an increase in said one or more of said genes in osteogenic medium, as compared to growth medium, in an equivalent number of adherent $CD200^+$, non-dim, placental stem cells, wherein said adherent $CD200^+$ non-dim, placental stem cells are not trophoblasts or cytotrophoblasts, and wherein said one or more genes comprise one or more, or all, of COL1A1, COL11A1, COL4A3, COL5A1, COMP (cartilage oligomeric matrix protein; see, e.g., GenBank Accession No. NM_000095), CTSK, FGF1 (fibroblast growth factor 1; see, e.g., GenBank Accession No. NM_000800), and/or FGFR2. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold higher than an increase in said one or more of said genes in osteogenic medium, as compared to growth medium, in an equivalent number of bone marrow-derived mesenchymal stem cells, and wherein said one or more genes comprise one or more, or all, of CSF3, IGF2, ITGA2, ITGA3, MMP9, MMP10, and/or TGFB2. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold lower than an increase in said one or more of said genes in osteogenic medium, as compared to growth medium, in an equivalent number of bone marrow-derived mesenchymal stem cells, and wherein said one or more genes comprise one or more, or all, of ALPL (alkaline phosphatase, liver/bone/kidney), CD36, COL10A1, COL11A1, COL12A1, COL1A1, COL4A3, COMP, CTSK, FGF1, and/or FGFR2. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold higher than an increase in said one or more of said genes in osteogenic medium, as compared to growth medium, in an equivalent number of fibroblast cells, and wherein said one or more genes comprise one or more, or all, of BMP2, CSF2, CSF3, IGF1, ITGA2, MMP9 and/or MMP10. In a specific embodiment, the population of cells consists essentially of OPACs.

In another embodiment, provided herein is a population of cells comprising OPACs, wherein an increase in expression in said population of cells, e.g., in the OPACs, of one or more genes in osteogenic medium, as compared to growth medium, is at least tenfold lower than an increase in said one or more of said genes in osteogenic medium, as compared to growth medium, in an equivalent number of fibroblast cells, and wherein said one or more genes comprise one or more, or all, of BMP4, COL12A1, COMP, FGF1, and/or MMP8. In a specific embodiment, the population of cells consists essentially of OPACs.

In another embodiment, provided herein is a population of cells comprising OPACs, e.g., a population of OPACs, wherein a gene encoding matrix metallopeptidase 9 (MMP9) is induced in said OPACs in osteogenic medium, as compared to expression of MMP9 in growth medium, at least 2, 3, 4 or 5 orders of magnitude greater than said MMP9 is induced in said osteogenic medium, as compared to expression of MMP9 in said growth medium, e.g., as assessed by Ct values from quantitative real-time PCR.

In another embodiment, provided herein is a population of cells comprising OPACs, e.g., a population of OPACs, wherein said population expresses one or more genes at least tenfold higher than an equivalent number of adherent CD200$^+$, non-dim, placental stem cells, wherein said one or more genes are CHRD (chordin; see, e.g., GenBank Accession No. NM_003741), GDF7 (growth differentiation factor 7; see, e.g., GenBank Accession No. NM_182828), IGFBP3 (Insulin-like growth factor binding protein 3; see, e.g., GenBank Accession No. NM_000598), and/or INHA (inhibin alpha; see, e.g., GenBank Accession No. NM_002191). In another embodiment, provided herein is a population of cells comprising OPACs, e.g., a population of OPACs, wherein said population expresses TGFB2 at least a tenfold lower level than an equivalent number of adherent CD200$^+$ (non-dim) placental stem cells.

In other embodiments, provided herein is a population of cells comprising OPACs, e.g., a population of OPACs, wherein the OPACs express α-smooth muscle actin, as detectable by immunofluorescent staining, and wherein said cells express a fibronectin-1 gene (FN1) and/or TGF-β2 gene (TGFB2) at approximately the same level as, or at an increased level compared to, an equivalent number of bone marrow-derived mesenchymal stem cells.

The level of expression of these genes can be used to confirm the identity of a population of OPACs, to identify a population of cells as comprising at least a plurality of OPACs, or the like. The population of OPACs can be clonal, e.g., a population of OPACs expanded form a single OPACs, or a mixed population of OPACs, e.g., a population of cells comprising solely OPACs that are expanded from multiple OPACs, or a population of cells comprising OPACs and at least one other type of cell.

The level of expression of these genes can be used to select populations of OPACs. For example, a population of cells, e.g., clonally-expanded cells, can be selected if the expression of one or more of these genes is significantly higher in a sample from the population of cells than in an equivalent population of mesenchymal stem cells. Such selecting can be of a population from a plurality of placental stem cell or chorionic stem cell populations, from a plurality of cell populations, the identity of which is not known, etc.

OPACs, and populations of cells comprising OPACs, can be selected on the basis of the level of expression of one or more such genes as compared to the level of expression in said one or more genes in a mesenchymal stem cell control. In one embodiment, the level of expression of said one or more genes in a sample comprising an equivalent number of mesenchymal stem cells is used as a control. In another embodiment, the control, for OPACs tested under certain conditions, is a numeric value representing the level of expression of said one or more genes in mesenchymal stem cells under said conditions.

OPACs, and populations of cells comprising OPACs, can also be selected on the basis of the expression of one or more secreted proteins as compared to the level of expression in a control, for example a placental stem cell, a mesenchymal stem cell or a fibroblast cell. In one embodiment, OPACs can be distinguished from placental stem cells, mesenchymal stem cells or fibroblast cells on the basis of secretion of one or more of decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 and TIMP-2, which are unique to OPACs as compared to adherent CD200$^+$ (non-dim) placental stem cells, mesenchymal stem cells or fibroblast cells. In another embodiment, proteins secreted by OPACs but not by PDACs™ include one or more of Tissue Factor, Follistatin-like 1, IGF-IIR, sFRP-4 and TSG-6.

The isolated populations of OPACs described above, and populations of OPACs generally, can comprise about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more OPACs.

5.1.1.3 Growth in Culture

The growth of the OPACs, as for any mammalian cell, depends in part upon the particular medium selected for growth. Under optimum conditions, OPACs typically double in number in 1-3 days. During culture, the OPACs provided herein adhere to a substrate in culture, e.g. the surface of a tissue culture container (e.g., tissue culture dish plastic, fibronectin-coated plastic, and the like) and form a monolayer.

5.1.2 Methods of Obtaining OPACs 5.1.2.1 Cell Collection Composition

Further provided herein are methods of collecting and isolating OPACs. Generally, OPACs are obtained from chorion using a physiologically-acceptable solution, e.g., a cell collection composition. A cell collection composition is described in detail in U.S. Application Publication No. 2007-0190042, the disclosure of which is incorporated by reference herein in its entirety.

The cell collection composition can comprise any physiologically-acceptable solution suitable for the collection and/or culture of cells, e.g., OPACs, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve OPACs, that is, prevent the OPACs from dying, or delay the death of the OPACs, reduce the number of OPACs in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/1); or an amiloride containing compound (e.g., amiloride, ethyl isopropyl amiloride, hexamethylene amiloride, dimethyl amiloride or isobutyl amiloride present at about 1.0 μM to about 5 μM).

5.1.2.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the chorion or OPACs isolated therefrom. For example, OPACs can be used, in light of the medical history, for personalized medicine for the infant associated with the placenta from which the chorion is obtained, or for parents, siblings or other relatives of the infant.

In certain embodiments, prior to recovery of OPACs, the umbilical cord blood and placental blood are removed from the placenta from which the chorion is to be removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of cells. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to collection or OPACs, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before OPACs are collected.

5.1.2.3 Physical Disruption and Enzymatic Digestion of Chorion Tissue

In one embodiment, OPACs are collected from a mammalian placenta by physical disruption, e.g., enzymatic digestion, of the organ. For example, the chorion, or a portion thereof, may be, e.g., crushed, sheared, minced, diced, chopped, macerated or the like, while in contact with the cell collection composition provided herein, and the resulting tissue subsequently digested with one or more enzymes. The chorion, or a portion thereof, may also be physically disrupted and digested with one or more enzymes, and the resulting material then immersed in, or mixed into, the cell collection composition. Any method of physical disruption can be used, provided that the method of disruption leaves a plurality, more preferably a majority, and more preferably at least about 60%, 70%, 80%, 90%, 95%, 98%, or 99% of the cells in said organ viable, as determined by, e.g., trypan blue exclusion. Typically, OPACs can be obtained by disruption of a small block of chorion, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred cell collection composition comprises one or more tissue-disruptive enzyme(s). Enzymatic digestion of chorion preferably uses a combination of enzymes, e.g., a combination of a matrix metalloprotease and a neutral protease, for example, a combination of collagenase and dispase. In other embodiments, enzymatic digestion of chorionic tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt chorionic tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate (tissue and cells resulting from enzymatic digestion) is preferably diluted so as to avoid trapping OPACs within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate OPACs. For example, in one embodiment, chorionic tissue is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In a specific embodiment, OPACs are obtained by separation of amnion from chorionic tissue; mincing the chorionic tissue, e.g., into pieces approximately 1 mm$^3$; digesting the tissue in dispase II, e.g., at about 1, 2, 3, 4 or 5 U/mL, e.g., 2.4 U/mL for a sufficient time, e.g., about 1 hour; digesting with collagenase II at about 100, 200, 300, 400 or 500 U/mL, e.g., about 270 U/ml for a sufficient time, e.g., about 1 hour, followed by enzyme neutralization, collection of single cells, and culture of the chorionic cells in a suitable medium, e.g., 20% FBS/αMEM.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the cell collection composition comprising the stem cells, or to a solution in which the tissue is disrupted and/or digested prior to isolation of the stem cells with the cell collection composition.

It will be appreciated that where an entire chorion, or portion of a chorion comprising both fetal and maternal cells, the OPACs collected can comprise a mix of OPACs derived from both fetal and maternal sources. Where a portion of the chorion that comprises no, or a negligible number of, maternal cells (for example, amnion), the OPACs collected will comprise almost exclusively fetal placental cells.

In one embodiment, OPACs are isolated from chorionic tissue as follows. Chorionic tissue is obtained and minced, e.g., into pieces approximately 1-2 mm$^3$. The minced tissue is digested with dispase II at a concentration of, e.g., about 1 U/mL to about 10 U/mL, e.g., 2.4 U/mL until digestion is complete, for example, for 1 hour at 37° C. The digested tissue is then digested with collagenase II, e.g., about 100 U/mL to about 1000 U/mL, e.g., about 27 U/mL, until digestion is complete, e.g, for about 1 hour at 37° C. Cells are collected by centrifugation, washed, and cultured on vitronectin-coated or laminin-coated tissue culture vessels and cultured in 10% FBS/DMEM or 20% FBS/αMEM for approximately 6 days. At 6 days' culture, non-adherent cells are removed, and adherent cells are allowed to proliferate. When the cells achieve about 80% to 90% confluence, the cells are removed, e.g., using trypsin, and transferred to vitronectin-coated or laminin-coated tissue culture vessels. Where cells are initially cultured on laminin-coated vessels, transfer to laminin-coated culture vessels is preferred; similarly, where cells are initially cultured on vitronectin-coated vessels, transfer to vitronectin-coated culture vessels is preferred Cells are optionally cryopreserved before transfer to second plates. Cells are analyzed, e.g., by flow cytometry for and are determined to be, e.g. CD34$^-$, CD105$^+$, CD200$^-$ and/or CD200$^{dim}$, positive for alkaline phosphatase (AP), α-smooth muscle actin (α-SMA) and osteoprotegerin (OP).

Thus, in one aspect, provided herein is a method of isolating osteogenic placental adherent cells (OPACs), comprising digesting chorion tissue serially with dispase II, then with collagenase II to produce a cell population; culturing said cell population on a first vitronectin-coated surface or laminin-coated surface for about six days, wherein said cell population comprises adherent cells and non-adherent cells; and removing non-adherent cells; and transferring the adherent cells to a second vitronectin-coated surface or laminin-coated surface, wherein said adherent cells are OPACs. In specific embodiments, said OPACs are one or more of CD34$^-$, CD105$^+$, CD200$^{dim}$, AP$^+$, α-SMA$^+$ and OP$^+$. In other embodiments, the OPACs have any of the cellular or genetic characteristics described elsewhere herein.

5.1.3 Culture of OPACs 5.1.3.1 Culture Media

Isolated OPACs, or populations of OPACs, can be used to initiate, or seed, cell cultures. Cells are generally transferred to sterile tissue culture vessels. The vessels are preferably coated with vitronectin, fibronectin, or both. In certain other embodiments, the tissue culture vessels are either uncoated or coated with extracellular matrix or ligands such as laminin, collagen (e.g., native or denatured), gelatin, ornithine, and/or extracellular membrane protein (e.g., MATRIGEL (BD Discovery Labware, Bedford, Mass.)).

Preferably, OPACs are obtained as follows. Chorionic cells comprising OPACs, obtained by digesting chorionic tissue, e.g., with dispase II and collagenase II as described above, are initially cultured on a tissue culture surface coated with collagen, vitronectin, or laminin, e.g., for about 1-6 days in 20% FBS/αMEM, followed by, or accompanied by, removal of non-adherent cells; non-adherent cells may be removed several times, e.g., after 3 hours, 1 day and 6 days of culture, or once, e.g., after 6 days of culture. Following selective adhesion, OPACs are selected by removal of CD200$^+$ (non-dim) cells, e.g., using an antibody to CD200, leaving a population of CD200$^{dim}$/CD200$^-$ cells.

OPACs can be cultured in any medium, and under any conditions, recognized in the art as acceptable for the culture of stem cells. Preferably, the culture medium comprises serum. OPACs can be cultured in, for example, DMEM-LG (Dulbecco's Modified Essential Medium, low glucose)/ MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX™ and gentamicin; DMEM comprising 10% FBS, GLUTAMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media that can be used to culture OPACs include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

OPACs can be cultured in standard tissue culture conditions, e.g., in tissue culture dishes or multiwell plates. OPACs can also be cultured using a hanging drop method. In this method, OPACs are suspended at about $1 \times 10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the cells are cultured.

5.1.3.2 Expansion and Proliferation of OPACs

Once an isolated OPAC, or isolated population of OPACs (e.g., an OPAC or population of OPACs separated from at least about 50% of the chorionic cells with which an OPAC or population of OPACs is normally associated in vivo) is obtained, the OPAC or population of OPACs can be proliferated and expanded in vitro. For example, a population of OPACs can be cultured in tissue culture containers, e.g., dishes, flasks, multiwell plates, or the like, for a sufficient time for the cells to proliferate to 70-90% confluence, that is, until the cells and their progeny occupy 70-90% of the culturing surface area of the tissue culture container.

OPACs can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. OPACs preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 cells, preferably about 50,000 cells, are passaged to a new culture container containing fresh culture medium. Typically, the new medium is the same type of medium from which the cells were removed. Provided herein are populations of placental cells that have been passaged at least 1, 2, 3, 4, 5, 6, 7, 8, 9, 10, 12, 14, 16, 18, or 20 times, or more.

5.1.3.3 OPAC Populations

Further provided herein are populations of OPACs. OPACs can be isolated directly from chorions from one or more placentas. Isolated OPACs provided herein can also be cultured and expanded to produce populations of OPACs. Populations of chorionic cells comprising OPACs can also be cultured and expanded to produce populations of OPACs.

OPACs populations provided herein comprise OPACs, for example, the OPACs as described herein. In various embodiments, at least about 10%, 20%, 30%, 40%, 50%, 60%, 70%, 80%, 90%, 95%, or 99% of the cells in an isolated cell population are OPACs. That is, a population of OPACs can comprise, e.g., as much as 1%, 5%, 10%, 20%, 30%, 40%, 50%, 60%, 70%, 80%, 90% non-OPAC cells.

Provided herein are methods of producing isolated populations of OPACs by, e.g., selecting cells from chorion that express particular markers and/or particular culture or morphological characteristics. In one embodiment, for example, provided herein is a method of producing a cell population comprising selecting chorionic cells that adhere to a substrate, and express CD105 but do not express CD200; and isolating said cells from other chorionic cells to form a cell population, e.g., a population of OPACs. In a specific embodiment CD105$^+$, CD200$^-$ chorionic cells that are also NG2$^+$, osteoprotegerin$^+$, alpha smooth muscle actin negative, and/or exhibit inducible alkaline phosphatase activity, are isolated from other chorionic cells.

In the above embodiments, the substrate can be any surface on which culture and/or selection of cells, e.g., OPACs, can be accomplished. Typically, the substrate is plastic, e.g., tissue culture dish or multiwell plate plastic. Tissue culture plastic can be coated with a biomolecule, e.g., laminin, vitronectin, collagen or fibronectin.

OPACs, and populations of OPACs, can be selected by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, CD200 (Abcam), or CD105 (Abcam; BioDesign International, Saco, Me.), etc. can be used to select OPACs or populations of OPACs.

Populations of OPACs can comprise chorionic cells that are not OPACs, or cells that are not chorionic cells or OPACs.

Isolated OPAC populations can be combined with one or more populations of non-OPAC cells or non-chorionic cells. For example, an isolated population of OPACs can be combined with blood (e.g., placental blood or umbilical cord blood), blood-derived stem cells (e.g., stem cells derived from placental blood or umbilical cord blood), populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated OPAC population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated OPAC population can be combined with a plurality of cells of a plurality of cell types, as well.

In one embodiment, an isolated population of OPACs is combined with a plurality of hematopoietic stem cells. Such hematopoietic stem cells can be, for example, contained within unprocessed placental blood, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.1.4 Combinations of OPACs and Placental Perfusate or Placental Perfusate Cells Provided herein are combinations of placental perfusate with isolated placental perfusate cells and/or the OPACs provided herein. In one embodiment, for example, provided herein is a volume of placental perfusate supplemented with a plurality of placental perfusate cells and/or a plurality of OPACs. In specific embodiments, for example, each milliliter of placental perfusate is supplemented with about $1\times10^4$, $5\times10^4$, $1\times10^5$, $5\times10^5$, $1\times10^6$, $5\times10^6$ or more placental perfusate cells or OPACs. In another embodiment, a plurality of placental perfusate cells is supplemented with placental perfusate and/or OPACs. In another embodiment, a plurality of OPACs is supplemented with placental perfusate and/or a plurality of placental perfusate cells. In certain embodiments, when perfusate is used for supplementation, the volume of perfusate is about, greater than about, or less than about, 50%, 45%, 40%, 35%, 30%, 25%, 20%, 15%, 10%, 8%, 6%, 4%, 2% or 1% of the total volume of cells (in solution) plus perfusate. When placental perfusate cells are used to supplement a plurality of OPACs, the placental perfusate cells generally comprise about, greater than about, or fewer than about, 50%, 45%, 40%, 35%, 30%, 25%, 20%, 15%, 10%, 8%, 6%, 4%, 2% or 1% of the total number of placental perfusate cells plus OPACs. Similarly, when OPACs are used to supplement a plurality of placental perfusate cells, the OPACs generally comprise about, greater than about, or fewer than about, 50%, 45%, 40%, 35%, 30%, 25%, 20%, 15%, 10%, 8%, 6%, 4%, 2% or 1% of the total number of placental perfusate cells plus OPACs. When OPACs or placental perfusate cells are used to supplement placental perfusate, the volume of solution (e.g., saline solution, culture medium or the like) in which the cells are suspended comprises about, greater than about, or less than about, 50%, 45%, 40%, 35%, 30%, 25%, 20%, 15%, 10%, 8%, 6%, 4%, 2% or 1% of the total volume of perfusate plus cells, where the OPACs are suspended to about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter prior to supplementation.

Further provided herein is pooled placental perfusate that is obtained from two or more sources, e.g., two or more placentas, and combined, e.g., pooled. Such pooled perfusate can comprise approximately equal volumes of perfusate from each source, or can comprise different volumes from each source. The relative volumes from each source can be randomly selected, or can be based upon, e.g., a concentration or amount of one or more cellular factors, e.g., cytokines, growth factors, hormones, or the like; the number of placental cells in perfusate from each source; or other characteristics of the perfusate from each source. Perfusate from multiple perfusions of the same placenta can similarly be pooled.

Similarly, provided herein are placental perfusate cells, and OPACs, that are obtained from two or more sources, e.g., two or more placentas and/or chorions, and pooled. Such pooled cells can comprise approximately equal numbers of cells from the two or more sources, or different numbers of cells from one or more of the pooled sources. The relative numbers of cells from each source can be selected based on, e.g., the number of one or more specific cell types in the cells to be pooled, e.g., the number of $CD34^-$ stem cells, etc.

Pools can comprise, e.g., placental perfusate supplemented with placental perfusate cells; placental perfusate supplemented with OPACs; placental perfusate supplemented with both placental perfusate cells and OPACs; placental perfusate cells supplemented with placental perfusate; placental perfusate cells supplemented with OPACs; placental perfusate cells supplemented with both placental perfusate and OPACs; OPACs supplemented with placental perfusate; OPACs supplemented with placental perfusate cells; or OPACs supplemented with both placental perfusate cells and placental perfusate.

In certain embodiments, placental perfusate, placental perfusate cells, and OPACs are provided as pharmaceutical grade administrable units. Such units can be provided in discrete volumes, e.g., 100 mL, 150 mL, 200 mL, 250 mL, 300 mL, 350 mL, 400 mL, 450 mL, 500 mL, or the like. Such units can be provided so as to contain a specified number of, e.g., placental perfusate cells, placental perfusate-derived intermediate natural killer cells, or both, e.g., $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter, or $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more cells per unit. Such units can be provided to contain specified numbers of any two, or all three, of placental perfusate, placental perfusate cells, and/or OPACs.

In the above combinations of placental perfusate, placental perfusate cells and/or OPACs, any one, any two, or all three of the placental perfusate, placental perfusate cells and/or OPACs can be autologous to a recipient (that is, obtained from the recipient), or homologous to a recipient (that is, obtained from at last one other individual from said recipient).

Also provided herein are compositions comprising OPACs in combination with placental perfusate cells and/or placental perfusate. Thus, in another aspect, provided herein is a composition comprising isolated OPACs, wherein said placental stem are isolated from placental perfusate, and wherein said OPACs comprise at least 50% of cells in the composition. In a specific embodiment, said OPACs comprise at least 80% of cells in the composition. In another specific embodiment, the composition comprises isolated placental perfusate. In a more specific embodiment, said placental perfusate is from the same individual as said OPACs. In another more specific embodiment, said placental perfusate comprises placental perfusate from a different individual than said OPACs. In another specific embodiment, the composition comprises placental perfusate cells. In a more specific embodiment, said placental perfusate cells are from the same individual as said OPACs. In another more specific embodiment, said placental perfusate cells are from a different individual than said OPACs. In another specific embodiment, the composition additionally comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals.

5.1.5 Production of an OPAC Cell Bank

OPACs from postpartum chorion can be cultured in a number of different ways to produce a set of lots, e.g., a set of individually-administrable doses. Sets of lots of OPACs, obtained from a plurality of chorions, can be arranged in a bank of OPACs for, e.g., long-term storage. Generally, OPACs are obtained from an initial culture of chorionic material to form a seed culture, which is expanded under controlled conditions to form populations of cells from approximately equivalent numbers of doublings. Lots are preferably derived from the chorionic tissue of a single placenta, but can be derived from the tissue of a plurality of placentas.

In one embodiment, OPACs lots are obtained as follows. Chorionic tissue is first disrupted, e.g., by mincing, digested with a suitable enzyme, e.g., dispase or dispase and collagenase (see Section 5.2.3, above). The chorionic tissue preferably comprises, e.g., the entire chorion from a single placenta, but can comprise only a part of the chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ cells. Preferably, from about $2 \times 10^4$ to about $3 \times 10^4$ Passage 0 cells are used to seed each expansion culture. The number of expansion cultures can depend upon the number of Passage 0 cells, and may be greater or fewer in number depending upon the particular chorion(s) from which the OPACs are obtained.

Expansion cultures are grown until the density of cells in culture reaches a certain value, e.g., about $1 \times 10^5$ cells/cm². Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for approximately 4 doublings, then frozen in a first cell bank. Cells from the first cell bank are frozen and used to seed a second cell bank, the cells of which are expanded for about another eight doublings. Cells at this stage are collected and frozen and used to seed new expansion cultures that are allowed to proceed for about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making an OPAC-containing composition.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of OPACs cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.1.6 Differentiation of OPACs

OPACs can be induced to differentiate, e.g., down an osteogenic pathway. Osteogenic differentiation of OPACs can be induced, for example, by placing OPACs in cell culture conditions that induce differentiation into osteogenic cells. A preferred osteocytic medium comprises MSCGM (Cambrex) or DMEM supplemented with 15% cord blood serum, followed by Osteogenic Induction Medium (Cambrex) containing 0.1 μM dexamethasone, 0.05 mM ascorbic acid-2-phosphate, 10 mM beta glycerophosphate. In another embodiment, OPACs are cultured in medium (e.g., DMEM-low glucose) containing about $10^{-7}$ to about $10^{-9}$ M dexamethasone, about 10-50 μM ascorbate phosphate salt (e.g., ascorbate-2-phosphate) and about 10 nM to about 10 mM β-glycerophosphate. Osteogenic medium can also include serum, one or more antibiotic/antimycotic agents, transforming growth factor-beta (e.g., TGF-β1) and/or bone morphogenic protein (e.g., BMP-2, BMP-4, or a combination thereof).

Differentiation can be assayed using a calcium-specific stain, e.g., von Kossa staining, and RT/PCR detection of, e.g., alkaline phosphatase, osteocalcin, bone sialoprotein and/or osteopontin gene expression.

5.1.7 Preservation of OPACs

OPACs can be preserved, that is, placed under conditions that allow for long-term storage, or conditions that inhibit cell death by, e.g., apoptosis or necrosis.

OPACs can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Medium for Collecting Placental Stem Cells and Preserving Organs," filed on Dec. 25, 2005. In one embodiment, provided herein is a method of preserving a population of OPACs comprising contacting said population of OPACs with a cell collection composition comprising an inhibitor of apoptosis and an oxygen-carrying perfluorocarbon, wherein said inhibitor of apoptosis is present in an amount and for a time sufficient to reduce or prevent apoptosis in the population of OPACs, as compared to a population of OPACs not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said OPACs. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the OPACs. In another more specific embodiment, said apoptosis inhibitor and said perfluorocarbon are between about 2° C. and 10° C., or between about 2° C. and about 5° C., at the time of contacting the OPACs. In another more specific embodiment, said contacting is performed during transport of said population of OPACs. In another more specific embodiment, said contacting is performed during freezing and thawing of said population of OPACs.

In another embodiment, provided herein is a method of preserving a population of OPACs comprising contacting said population of OPACs with an inhibitor of apoptosis and an organ-preserving compound, wherein said inhibitor of apoptosis is present in an amount and for a time sufficient to reduce or prevent apoptosis in the population of OPACs, as compared to a population of OPACs not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, OPACs are contacted with a cell collection composition comprising an apoptosis inhibitor and oxygen-carrying perfluorocarbon, organ-preserving compound, or combination thereof, during perfusion. In another embodiment, said OPACs are contacted during a process of tissue disruption, e.g., enzymatic digestion. In another embodiment, OPACs are contacted with said cell collection compound after collection by perfusion, or after collection by tissue disruption, e.g., enzymatic digestion.

Typically, during cell collection, enrichment and isolation, it is preferable to minimize or eliminate cell stress due to hypoxia and mechanical stress. In another embodiment of the method, therefore, OPACs are exposed to a hypoxic condition during collection, enrichment or isolation for less than six hours during said preservation, wherein a hypoxic condition is a concentration of oxygen that is less than normal blood oxygen concentration. In a more specific embodiment, said OPACs are exposed to said hypoxic condition for less than two hours during said preservation. In another more specific embodiment, OPACs are exposed to said hypoxic condition for less than one hour, or less than thirty minutes, or are not exposed to a hypoxic condition, during collection, enrichment or isolation. In another specific embodiment, said OPACs are not exposed to shear stress during collection, enrichment or isolation.

The OPACs provided herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. OPACs are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.1.8 Compositions Comprising OPACs

Provided herein are compositions comprising OPACs, or biomolecules therefrom. The OPACs provided herein can be combined with any physiologically-acceptable or medically-acceptable compound, composition or device for use in, e.g., research or therapeutics.

5.1.8.1 Cryopreserved OPACs

The populations of OPACs provided herein can be preserved, for example, cryopreserved for later use. Methods for cryopreservation of cells, such as OPACs, are well known in the art. OPACs populations can be prepared in a form that is easily administrable to an individual. For example, provided herein is a OPACs population that is contained within a container that is suitable for medical use. Such a container can be, for example, a sterile plastic bag, flask, jar, or other container from which the OPACs population can be easily dispensed. For example, the container can be a blood bag or other plastic, medically-acceptable bag suitable for the intravenous administration of a liquid to a recipient. The container is preferably one that allows for cryopreservation of the combined cell population.

The cryopreserved OPACs population can comprise OPACs derived from a single donor, or from multiple donors. The population of OPACs can be completely HLA-matched to an intended recipient, or partially or completely HLA-mismatched.

Thus, in one embodiment, provided herein is a composition comprising a population of OPACs in a container. In a specific embodiment, the population is cryopreserved. In another specific embodiment, the container is a bag, flask, or jar. In more specific embodiment, said bag is a sterile plastic bag. In a more specific embodiment, said bag is suitable for, allows or facilitates intravenous administration of an OPAC population. The bag can comprise multiple lumens or compartments that are interconnected to allow mixing of the OPACs and one or more other solutions, e.g., a drug, prior to, or during, administration. In another specific embodiment, the composition comprises one or more compounds that facilitate cryopreservation of the cell population. In another specific embodiment, said population of OPACs is contained within a physiologically-acceptable aqueous solution. In a more specific embodiment, said physiologically-acceptable aqueous solution is a 0.9% NaCl solution. In another specific embodiment, said population of OPACs comprises placental cells that are HLA-matched to a recipient of said population. In another specific embodiment, said population of OPACs comprises cells that are at least partially HLA-mismatched to a recipient of said population. In another specific embodiment, said OPACs are derived from a plurality of donors.

5.1.8.2 Pharmaceutical Compositions

Populations of OPACs, or populations of cells comprising OPACs, can be formulated into pharmaceutical compositions for use in vivo. Such pharmaceutical compositions comprise a population of OPACs, or a population of cells comprising OPACs, in a pharmaceutically-acceptable carrier, e.g., a saline solution or other accepted physiologically-acceptable solution for in vivo administration. Pharmaceutical compositions provided herein can comprise any of the OPAC populations described elsewhere herein. The pharmaceutical compositions can comprise fetal, maternal, or both fetal and maternal OPACs. The pharmaceutical compositions provided herein can further comprise OPACs obtained from a single individual or chorion, or from a plurality of individuals or chorion.

The pharmaceutical compositions provided herein can comprise any therapeutically useful number of OPACs. For example, a single unit dose of OPACs can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more OPACs.

The pharmaceutical compositions provided herein can comprise populations of cells that comprise 50% viable cells or more (that is, at least about 50% of the cells in the population are functional or living). Preferably, at least about 60% of the cells in the population are viable. More preferably, at least about 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

5.1.8.3 OPAC Conditioned Media

The OPACs provided herein can be used to produce conditioned medium, that is, medium comprising one or more biomolecules secreted or excreted by the cells. In various embodiments, the conditioned medium comprises medium in which OPACs have grown for at least 1, 2, 3, 4, 5, 6, 7, 8, 9, 10, 11, 12, 13, 14 or more days. In other embodiments, the conditioned medium comprises medium in which OPACs have grown to at least about 30%, 40%, 50%, 60%, 70%, 80%, 90% confluence, or up to 100% confluence. Such conditioned medium can be used to support the culture of a separate population of OPACs, or stem cells of another kind. In another embodiment, the conditioned medium comprises medium in which OPACs have been differentiated into a terminally differentiated cell type, or a cell having one or more characteristics of a terminally differentiated cell. In another embodiment, the conditioned medium provided herein comprises medium in which OPACs and non-OPACs have been cultured.

5.1.8.4 Matrices Comprising OPACs

Further provided herein are matrices, hydrogels, scaffolds, and the like that comprise an OPAC, or a population of OPACs. In certain embodiments, the matrix can be any substrate known to one skilled in the art to be useful for treating bone defects. For example, the matrix can be a β-tricalcium phosphate substrate, a β-tricalcium phosphate-collagen substrate, a collagen substrate, a calcium phosphate substrate, a mineralized collagen substrate, and a hyaluronic acid substrate. In some embodiments, the collagen in the matrix can be placental collagen. Methods and compositions for isolating and preparing placental collagen are extensively described, for example, in U.S. Patent Application Publication No. 2007/0020225, the disclosure of which is incorporated by reference herein in its entirety.

OPACs can be seeded onto the matrix for treating bone prior to or after a differentiation step. For example, OPACs can be cultured in, e.g., osteogenic medium for, e.g., about 1-20 days, then seeded onto the matrix. Alternately, OPACs can be isolated and seeded onto the matrix, then cultured in osteogenic medium as described herein for, e.g., about 1-20 days. In another embodiment, OPACs are cultured in, e.g., osteogenic medium for, e.g., about 1-20 days, then seeded onto the matrix, then cultured in osteogenic medium as described herein for, e.g., about 1-20 days.

OPACs can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which OPACs can be seeded are described in Hariri, U.S. Application Publication No. 2004/0048796.

OPACs as provided herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. OPACs in such a matrix can also be cultured so that the cells are mitotically expanded prior to implantation. The hydrogel is, e.g., an organic polymer (natural or synthetic) that is crosslinked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix biodegradable.

In some embodiments, the formulation comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The OPACs or populations thereof can be seeded onto a three-dimensional framework or scaffold and implanted in vivo. Such a framework can be implanted in combination with any one or more growth factors, cells, drugs or other components that stimulate tissue formation or otherwise enhance or improve repair of tissue.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

OPACs provided herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, OPACs can be seeded onto, or contacted with, a felt, which can be, e.g., composed of a multifilament yarn made from a bioabsorbable material such as PGA, PLA, PCL copolymers or blends, or hyaluronic acid.

The OPACs provided herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the OPACs in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with OPACs. The scaffold can further comprise agents that stimulate bone growth and/or inhibit bone resorption. For example, the scaffold can comprise bone morphogenic proteins, e.g., BMP-2 and/or BMP-7, WNT inhibitors, and the like.

5.1.9 Immortalized OPAC Cell Lines

OPACs can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. In one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 μg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed as described herein. Cells carrying $neo^R$ may be selected by means known to those of ordinary skill in the art, such as the addition of, e.g., 100-200 μg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least about 30% of the cells to double in a 24 hour period. Preferably, the substrate is a polyornithine/laminin substrate, consisting of tissue culture plastic coated with polyornithine (10 μg/mL) and/or laminin (10 μg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized OPAC cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human OPAC cell line prepared as described above. In general, such clonal cell lines may be isolated using standard techniques, such as by limit dilution or using cloning rings, and expanded. Clonal cell lines may generally be fed and passaged as described above.

Conditionally-immortalized human OPAC cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.1.10 Assays

The OPACs provided herein can be used in assays to determine the influence of culture conditions, environmental factors, molecules (e.g., biomolecules, small inorganic molecules. etc.) and the like on OPACs proliferation, expansion, and/or differentiation, compared to OPACs not exposed to such conditions.

In a preferred embodiment, the OPACs provided herein are assayed for changes in proliferation, expansion or differentiation upon contact with a molecule. For example, osteogenic differentiation can be assayed by monitoring alkaline phosphatase activity and/or calcium mineralization.

In one embodiment, for example, provided herein is a method of identifying a compound that modulates the proliferation of a plurality of OPACs, comprising contacting said plurality of OPACs with said compound under conditions that allow proliferation, wherein if said compound causes a detectable change in proliferation of said plurality of OPACs compared to a plurality of OPACs not contacted with said compound, said compound is identified as a compound that modulates proliferation of OPACs. In a specific embodiment, said compound is identified as an inhibitor of proliferation. In another specific embodiment, said compound is identified as an enhancer of proliferation.

In another embodiment, provided herein is a method of identifying a compound that modulates the expansion of a plurality of OPACs, comprising contacting said plurality of OPACs with said compound under conditions that allow expansion, wherein if said compound causes a detectable change in expansion of said plurality of OPACs compared to a plurality of OPACs not contacted with said compound, said compound is identified as a compound that modulates expansion of OPACs. In a specific embodiment, said compound is identified as an inhibitor of expansion. In another specific embodiment, said compound is identified as an enhancer of expansion.

In another embodiment, provided herein is a method of identifying a compound that modulates the differentiation of OPACs, comprising contacting said OPACs with said compound under conditions that allow differentiation, wherein if said compound causes a detectable change in differentiation of said OPACs compared to OPACs not contacted with said compound, said compound is identified as a compound that modulates proliferation of OPACs. In a specific embodiment, said compound is identified as an inhibitor of proliferation. In another specific embodiment, said compound is identified as an enhancer of proliferation.

5.2 Uses of OPACs

5.2.1 Treatment of Bone-Related Cancers Using OPACs

Provided herein are methods of treating individuals having a bone-related cancer comprising administering to the individual a therapeutically-effective amount of OPACs. Bone-related cancers include, without limitation, multiple myeloma, bone cancer, breast cancer, lung cancer, neuroblastoma, osteosarcoma, Ewing's sarcoma, chondrosarcoma, chordoma, malignant fibrous histiocytoma of bone, fibrosarcoma of bone, metastatic cancer, multiple myeloma, and any form of metastatic cancer characterized by bone metastases. In certain embodiments, the administration of OPACs is therapeutically effective to reduce, ameliorate or reverse one or more symptoms associated with the bone-related cancer, e.g., a symptom caused by or related to an effect of the cancer on one or more bones in the individual. As one skilled in the art will recognize, treatment of bone defects caused by cancer may not necessarily abate the cancer itself. Treatment of cancer-related bone defects as provided herein can occur before, after, or concurrently with additional cancer therapies, as discussed below. Accordingly, in one embodiment, bone defects are treated before the cancer is treated with an anti-cancer therapy. In another embodiment, bone defects are treated at or near the same time that the cancer is treated with an anti-cancer therapy. In another embodiment, bone defects are treated after the cancer is treated with an anti-cancer therapy.

In certain embodiments, treatment of bone-related cancers, e.g., multiple myeloma, comprises administering a therapeutically-effective amount of OPACs to an individual having bone-related cancer cells, e.g., multiple myeloma cells, wherein at least some of said OPACs directly contact at least some multiple myeloma cells, e.g., there is direct cell-cell contact between at least some of said OPACs and some of said bone-related cancer cells. In certain other embodiments, treatment of bone-related cancers, e.g., multiple myeloma, comprises administering a therapeutically-effective amount of OPACs to an individual having bone-related cancer cells, e.g., multiple myeloma cells, wherein none, or substantially none, of said OPACs directly contact multiple myeloma cells, e.g., there is no, or substantially no, direct cell-cell contact between at least some of said OPACs and bone-related cancer cells.

In certain embodiments, the OPACs are administered intralesionally, e.g., directly into, or adjacent to (e.g., within 1-5 cm of) one or more bone lesions caused by the cancer. In certain embodiments, the OPACs are administered in combination with a matrix, e.g., an injectable matrix.

In certain other embodiments, OPACs are administered to an individual having a bone-related cancer in combination with a solid matrix, e.g., a bone substitute, a matrix or bone substitute described in Section 5.2.2, below.

In certain other embodiments, the OPACs are administered intravenously to the individual. The OPACs can be administered from any container, and by any delivery system, medically suitable for the delivery of fluids, e.g., fluids comprising cells, to an individual. Such containers can be, for example, a sterile plastic bag, flask, jar, or other container from which the OPACs population can be easily dispensed. For example, the container can be a blood bag or other plastic, medically-acceptable bag suitable for the intravenous administration of a liquid to a recipient.

Intralesional or intravenous administration can comprise, e.g., about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more OPACs in a single dose. OPACs may be administered once, or more than once, during a course of therapy. Preferably, the administered OPACs comprise 50% viable cells or more (that is, at least about 50% of the cells in the population are functional or living). Preferably, at least about 60% of the cells in the population are viable. More preferably, at least about 70%, 80%, 90%, 95%, or 99% of the cells in the population in the pharmaceutical composition are viable.

5.2.1.1 Treatment of Multiple Myeloma

Provided herein are methods of treating an individual having multiple myeloma, comprising administering to said individual a plurality of OPACs, wherein said OPACs have any combination of, or all of, the characteristics described in Section 5.1, above. In a specific embodiment, said plurality of OPACs is $CD105^+$ and $CD200^{dim}$ or $CD105^+$ and $CD200^-$. The methods of treatment provided herein encompass the use of any of the OPACs, populations of OPACs, or populations of cells comprising OPACs, described in Section 5.1, above.

Multiple myeloma is a cancer of plasma cells, which are antibody-producing cells of the immune system. The disease typically presents with four main characteristics: elevated calcium, renal failure, anemia, and bone lesions. These symptoms and others are discussed below.

Bone Pain—

Myeloma cells secrete IL-6, also known as osteoclast activating factor (OAF), which is a cytokine that activates osteoclasts to break down bone, creating painful bone lesions. These bone lesions are lytic in nature and are visible in radiographs, which may show "punched-out" resorptive lesions. Myeloma bone pain usually involves the spine and ribs, and worsens with activity. Persistent localized pain may be present, and can indicate a pathological bone fracture. Involvement of the vertebrae may lead to spinal cord compression. The breakdown of bone also leads to release of calcium into the blood, leading to hypercalcemia and its associated symptoms.

The areas of breakdown of bone, as viewed in a skeletal survey, typically appears as one or more lytic lesions on the bone, that is, regions in which the bone appears absent or "punched out."

Infection—

Another common symptom of multiple myeloma is infection, as the immune system is disrupted. The increased risk of infection is due to immune deficiency resulting from diffuse hypogammaglobulinemia, which is due to decreased production and increased destruction of normal antibodies. The most common infections are pneumonias and pyelonephritis. Common pneumonia pathogens causing disease in multiple myeloma patients include *Streptococcus pneumoniae*, *Staphylococcus aureus*, and *Klebsiella pneumoniae*, while common pathogens causing pyelonephritis include *Escherichia coli*. Typically, infection occurs in the initial few months after the start of chemotherapy.

Renal Failure—

Multiple myeloma also tends to result in renal failure, which may develop both acutely and chronically. Renal failure in multiple myeloma is largely attributable to hypercalcemia, which develops as osteoclasts dismantle existing bone. Renal failure is also caused by tubular damage from excretion of light chains, also called Bence Jones proteins, which can manifest as the Fanconi syndrome (type II renal tubular acidosis). Other causes include glomerular deposition of amyloid, hyperuricemia, recurrent infections (e.g., pyelonephritis), and local infiltration of tumor cells. Renal failure can be associated with elevated levels of serum creatinin.

Anemia—

The anemia found in myeloma is usually normocytic and normochromic, and results from the replacement of normal bone marrow by infiltrating tumor cells and inhibition of normal red blood cell production (hematopoiesis) by cytokines.

Neurological Symptoms—

Symptoms of multiple myeloma include a spectrum of neurological conditions, including weakness, confusion and fatigue due to hypercalcemial headache, visual changes and retinopathy, which can be the result of hyperviscosity of the blood depending on the properties of paraprotein (see below). Other neurological symptoms include radicular pain, loss of bowel or bladder control (for example, due to involvement of spinal cord leading to cord compression), and carpal tunnel syndrome and other neuropathies (for example, due to infiltration of peripheral nerves by amyloid). Multiple myeloma may give rise to paraplegia in late presenting cases.

Presence of Paraprotein—

A diagnostic symptom of multiple myeloma is the presence in the blood and/or urine of paraprotein, which is a monoclonal protein (M protein), e.g., an immunoglobulin light-chain that is produced by the clonal proliferation of plasma cells, or immunoglobulin fragments.

Symptomatic multiple myeloma is typically diagnosed when the following symptoms or signs are present: clonal plasma cells constituting greater than 10% of cells on bone marrow biopsy or, in any quantity in a biopsy from other tissues (e.g., plasmacytoma); paraprotein in either serum or urine; evidence of end-organ damage (related organ or tissue impairment), for example, hypercalcemia (e.g., corrected calcium >2.75 mmol/L in the blood), renal insufficiency attributable to myeloma, anemia defined as hemoglobin <10 g/dL blood, bone lesions (e.g., lytic lesions or osteoporosis with compression fractures, frequent severe infections (>2 a year), amyloidosis (the deposition of amyloid protein) of other organs, and hyperviscosity syndrome (increase in the viscosity of blood).

Individuals having multiple myeloma fall into one of the following groups. In one embodiment, the individual having multiple myeloma has never been treated for the disease. In another embodiment, the individual has responsive myeloma; that is, multiple myeloma that is responding to therapy. In a specific embodiment, such an individual exhibits a decrease in M protein (paraprotein) of at least 50% as a result of treatment. In another specific embodiment, the individual exhibits a decrease in M protein of between 25% and 50% as a result of treatment. In another embodiment, the individual has stable multiple myeloma, which refers to myeloma that has not responded to treatment (for example, the decrease in M protein has not reached 50%), but has not progressed or gotten worse. In another embodiment, the individual has progressive multiple myeloma, which refers to active myeloma that is worsening (for example, increasing M protein and worsening organ or tissue impairment or end organ damage).

In another embodiment, the individual has relapsed multiple myeloma, which refers to myeloma disease that initially responded to therapy but has then begun to progress again. In specific embodiments, the individual has relapsed after initial therapy or has relapsed after subsequent therapy. In another embodiment, the individual has refractory multiple myeloma. In a specific embodiment, the refractory multiple myeloma is multiple myeloma that has not responded to initial therapy. In another specific embodiment, the refractory multiple myeloma is relapsed multiple myeloma that has not responded to subsequent treatment. In another specific embodiment, the refractory multiple myeloma is non-responding progressing refractory disease, which refers to refractory disease that is progressing. In another specific embodiment, the refractory multiple myeloma is non-responding non-progressing refractory disease, which refers to refractory disease that is not worsening.

Thus, in one embodiment, provided herein is a method of treating an individual having multiple myeloma, comprising administering to the individual OPACs, a population of OPACs or a population of cells comprising OPACs, wherein said administration results in the detectable reduction of progression, detectable cessation of worsening, and/or detectable improvement, of one or more symptoms of multiple myeloma. In specific embodiments, said one or more symptoms comprise elevated blood or urine calcium compared to normal, the presence of bone lesions, anemia, or renal failure. In a more specific embodiment, said one or more symptoms comprises clonal plasma cells constituting greater than 10% of cells on bone marrow biopsy or, in any quantity in a biopsy from other tissues (e.g., plasmacytoma); paraprotein in either serum or urine; and/or evidence of end-organ damage. In a more specific embodiment, said one or more symptoms is a concentration of calcium in the blood of greater than 2.75 mmol/L, renal insufficiency, less than 10 g hemoglobin per deciliter of blood, the presence of bone lesions, or amyloidosis of one or more organs other than bone marrow.

In another specific embodiment, said symptom is a neurological symptom. In more specific embodiments, said neurological symptoms are weakness, confusion, fatigue, headache, visual changes, retinopathy, radicular pain, loss of bowel or bladder control, carpal tunnel syndrome, and/or paraplegia.

In a specific embodiment, provided herein is a method of treating an individual having multiple myeloma, comprising administering to the individual OPACs, a population of OPACs or a population of cells comprising OPACs, wherein said administration results in the detectable reduction in number of multiple myeloma cells, e.g., clonal multiple myeloma cells, in one or more organs of the individual.

In a specific embodiment, provided herein is a method of treating an individual having multiple myeloma, comprising administering to the individual OPACs, a population of OPACs or a population of cells comprising OPACs, wherein said administration results in the detectable increase in hemoglobin in the blood of the individual, e.g., an increase to within normal limits. Normal hemoglobin levels vary by the age and sex of the individual, as shown in Table 1, below:

TABLE 1

| | |
|---|---|
| Newborns | 17-22 gm/dl |
| One (1) week of age | 15-20 gm/dl |
| One (1) month of age | 11-15 gm/dl |
| Children | 11-13 gm/dl |
| Adult males | 14-18 gm/dl |
| Adult women | 12-16 gm/dl |
| Men after middle age | 12.4-14.9 gm/dl |
| Women after middle age | 11.7-13.8 gm/dl |

Thus, in a more specific embodiment, provided herein is a method of treating an individual having multiple myeloma, comprising administering to the individual OPACs, a population of OPACs or a population of cells comprising OPACs, wherein said administration results in the increase of blood hemoglobin levels in said individual to between 11 g/dL blood and 20 g/dL blood. In a more specific embodiment, said administering results in the increase of blood hemoglobin levels in said individual to between 11 g/dL blood and 13 g/dL blood. In another more specific embodiment, said administering results in the increase of blood hemoglobin levels in said individual to between 12 g/dL blood and 16 g/dL blood. In a more specific embodiment, said administering results in the increase of blood hemoglobin levels in said individual to between 14 g/dL blood and 18 g/dL blood.

In another embodiment, provided herein is a method of treating an individual having multiple myeloma, comprising administering to the individual OPACs, a population of OPACs or a population of cells comprising OPACs, wherein said administration results in detectable reduction in the level of paraprotein in blood or urine from said individual. In a specific embodiment, said administering results in the reduction of paraprotein in blood or urine of said individual to an undetectable level.

In another embodiment, provided herein is a method of treating an individual having multiple myeloma, comprising administering to the individual OPACs, a population of OPACs or a population of cells comprising OPACs, wherein said administration results in detectable reduction in the severity and/or number of bone lesions caused by multiple myeloma in said individual, as determined by, e.g., bone scan or radiography. In another embodiment, provided herein is a method of treating an individual having multiple myeloma, comprising administering to the individual OPACs, a population of OPACs or a population of cells comprising OPACs, wherein said administration results in detectable reduction in loss of bone mass or bone mineral content, cessation of loss of bone mass or bone mineral content, or increase in bone mass or bone mineral content, in said individual.

In another specific embodiment of the method of treatment, said one or more symptoms of multiple myeloma are bone pain, osteocytic lesions (e.g., visible by X-ray or magnetic resonance imaging (MRI)), osteoporosis, anemia, hypercalcemia or a symptom due to hypercalcemia, or renal failure. In other specific embodiments, said individual has never been treated for multiple myeloma; said individual has been treated for multiple myeloma and responds to non-OPAC therapy; said individual has been treated for multiple myeloma and has not responded to non-OPAC therapy, but the course of multiple myeloma in said individual has not progressed; or said individual has progressive multiple myeloma.

In another aspect, provided herein is a method of suppressing the proliferation of multiple myeloma cells, comprising contacting said multiple myeloma cells with a plurality of OPACs, such that proliferation of said multiple myeloma cells is detectably suppressed. In certain embodiments, provided herein is a method of suppressing the proliferation of multiple myeloma cells in vivo, comprising administering a therapeutically-effective amount of OPACs to an individual comprising multiple myeloma cells, wherein said administering detectably reduces proliferation of said multiple myeloma cells. In a specific embodiment, said administering detectably reduces (e.g., improves) one or more symptoms or signs of multiple myeloma, or lessens the worsening of said one or more symptoms or signs of multiple myeloma.

OPACs, useful in the methods provided herein, are adherent, osteogenic cells from chorion (but not chorionic skirt (laeve)) that can be identified and selected by the morphological, marker, and culture characteristics discussed at least in Section 5.1, above.

5.2.1.2 Combination Therapies

Treatment of a bone-related cancer, e.g., multiple myeloma, can comprise administration of OPACs, in combination with another therapy, to the individual having the cancer.

Thus, in another aspect, provided herein is a method of treating an individual having a bone-related cancer, e.g., multiple myeloma, comprising administering to the individual OPACs, a population of OPACs or a population of cells comprising OPACs, in combination with one or more other anticancer therapies, e.g., one or more chemotherapies or chemotherapeutic compounds. Such other anticancer therapies can be administered to the individual at the same time as, during the same course of treatment as, or separately from, said administration of OPACs. In a specific embodiment, the administration of said other anticancer therapies is administered sequentially with administration of said OPACs. In a more specific embodiment, said other anticancer therapy or anticancer therapies are administered to said individual before administration of said OPACs; e.g., a course of such other anticancer therapies is administered to the individual, and completed, prior to administration to the individual of OPACs. In another more specific embodiment, said OPACs are administered to the individual before administration of said other anticancer therapies; e.g., a course of OPACs is administered to said individual before administration of said other anticancer therapies, and completed, prior to administration to the individual said other anticancer therapy or anticancer therapies.

In a specific embodiment, the anticancer agent is melphalan (also known as L-phenylalanine mustard or L-PAM; trade name Alkeran). Thus, in one embodiment, the method of treating an individual having multiple myeloma comprises administering to said individual melphalan, e.g., a therapeutically effective dose or doses of melphalan. Administration is typically oral or intravenous. In another specific embodiment, the anticancer agent is thalidomide. In another specific embodiment, the anticancer agent is pomalidomide (sold under the trade name ACTIMID®); lenalidomide (sold under the trade name REVLIMID®); or lenalidomide in combination with dexamethasone. In another specific embodiment, the anticancer treatment is bortezomib (VELCADE®). In another specific embodiment, the anticancer agent comprises a combination of melphalan, prednisone, and thalidomide (administered separately or together). In another specific embodiment, the anticancer agent is bortezomib, melphalan and prednisone (administered separately or together).

Other anticancer agents are well-known in the art. Thus, in other specific embodiments, the anticancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS);

castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In other embodiments, the combination therapy comprises administration of OPACs to an individual in combination with an inhibitor of osteoclasts. In a specific embodiment, the osteoclast inhibitor is an inhibitor of RANKL, e.g., Denosumab. In another specific embodiment, the osteoclast inhibitor is an integrin or cathepsin K inhibitor.

In another embodiment, the combination therapy comprises administration of OPACs in combination with bisphosphonates. In specific embodiments, the bisphosphonates are clodronate and/or pamidronate.

5.2.2 Treatment of Bone Defects Using OPACs

Populations of OPACs can be used to treat bone defects, e.g., bone defects arising from trauma, or from disease, e.g., disease other than a bone-relate cancer. OPACs can also be used to treat any disease, disorder or condition that results in, or is related to, loss of bone. As used herein, "treat" encompasses the cure of, remediation of, improvement of, lessening of the severity of, or reduction in the time course of, a disease, disorder or condition, or any parameter or symptom thereof.

Isolated populations of OPACs may also be used to treat bone fractures, e.g., non-union bone fractures. Isolated populations of OPACs may also be used to fuse vertebrae together in order to, e.g., complete a spinal fusion in a subject in need thereof. Isolated populations of OPACs, in combination with stem or progenitor cell populations, may also be used to treat the foregoing.

OPACs can be combined with a substrate, e.g., a matrix, to form an implantable composition. For example, provided herein is a composition, e.g., an implantable composition, comprising OPACs. In a specific embodiment, the implantable composition comprises a matrix. In a more specific embodiment, said matrix is a three-dimensional scaffold. In another more specific embodiment, said matrix comprises collagen, gelatin, laminin, fibronectin, pectin, ornithine, or vitronectin. In another specific embodiment, said matrix comprises hydroxyapatite. In a more specific embodiment, said matrix comprises both collagen and hydroxyapatite, e.g., the matrix is HEALOS®. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons. In certain embodiments, the matrix is a synthetic degradable polymer such as, for example, polylactic acid or polyglycolic acid. In certain embodiments, the implantable scaffolding substrate is a β-tricalcium phosphate substrate, a β-tricalcium phosphate-collagen substrate, a collagen substrate, a calcium phosphate substrate, a mineralized human placental collagen substrate, a hyaluronic acid substrate, or a ceramic substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate.

OPACs, and populations of OPACs, can also be induced to differentiate into a particular cell type, either ex vivo or in vivo, in preparation for administration to an individual in need of such cells, or cells differentiated from such cells. For example, OPACs can be injected into a damaged organ, e.g., a damaged bone, for organ neogenesis and repair of injury in vivo. Such injury may be due to such conditions and disorders including, but not limited to, bone defects including lesions resulting from osteoporosis, cancer, fractures, and spinal conditions treatable with, e.g., spinal fusion. The OPACs can be injected into the damaged bone alone or can be introduced with an implantable substrate as described herein.

When OPACs are administered as a suspension or liquid injectable, the cells can be administered intravenously, or, preferably, at the site of the bone defect, e.g., break.

In certain aspects, provided herein is a method for treating bone defects in a subject, comprising administering to a subject in need thereof an implantable or injectable composition comprising a population of OPACs provided herein, thereby treating the bone defect in the subject. In certain embodiments, the bone defect is an osteolytic lesion associated with a cancer, a bone fracture, or a spine, e.g., in need of fusion. In certain embodiments, the osteolytic lesion is associated with multiple myeloma, bone cancer, or metastatic cancer. In certain embodiments, the bone fracture is a non-union fracture. In certain embodiments, an implantable composition is surgically implanted, e.g., at the site of the bone defect. In certain embodiments, an injectable composition is surgically administered to the region of the bone defect. In certain embodiments, the injectable composition is systemically administered.

In a specific embodiment, the implantable composition comprising OPACs comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons. In certain embodiments, the matrix is a synthetic degradable polymer such as, for example, polylactic acid or polyglycolic acid. In certain embodiments, the implantable scaffolding substrate is selected from the group consisting of a β-tricalcium phosphate substrate, a β-tricalcium phosphate-collagen substrate, a collagen substrate, a calcium phosphate substrate, a mineralized human placental collagen substrate, a hyaluronic acid substrate, and a ceramic substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate.

In another aspect, provided herein is a method for formulating an injectable composition, comprising combining a population of OPACs with injectable hyaluronic acid or collagen. In another aspect, provided herein is an injectable composition comprising OPACs and hyaluronic acid or collagen.

OPACs can be administered without being cultured under conditions that cause the OPACs to differentiate. Alternately, the OPACs can be cultured in, e.g., e.g., osteogenic medium for, e.g., about 1-20 days, prior to administration. Alternately, OPACs can be isolated and seeded on a matrix, then cultured in osteogenic medium for, e.g., about 1-20 days. In another embodiment, OPACs can be cultured in, e.g., osteogenic medium for, e.g., about 1-20 days, then seeded onto a matrix, then cultured in osteogenic medium as described herein for, e.g., about 1-20 days.

In other embodiments, isolated populations of OPACs may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

In certain embodiments, an isolated population of OPACs is used in hematopoietic reconstitution in an individual that has suffered a partial or total loss of hematopoietic stem cells, e.g., individuals exposed to lethal or sub-lethal doses of radiation (whether industrial, medical or military); individuals that have undergone myeloablation as part of, e.g., cancer therapy, and the like. Isolated populations of OPACs can be used in place of, or to supplement, bone marrow or populations of stem cells derived from bone marrow. Typically, approximately $1 \times 10^8$ to $2 \times 10^8$ bone marrow mononuclear cells per kilogram of patient weight are infused for engraftment in a bone marrow transplantation (i.e., about 70 ml of marrow for a 70 kg donor). To obtain 70 ml requires an intensive donation and significant loss of donor blood in the donation process. An isolated population of OPACs for hematopoietic reconstitution can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more OPACs.

The OPACs provided herein, alone or in combination with other stem cell or progenitor cell populations, can be used in the manufacture of a tissue or organ in vivo. The methods provided herein encompass using OPACs to seed a matrix and to be cultured under the appropriate conditions to allow the cells to differentiate and populate the matrix. The tissues and organs obtained by the methods provided herein can be used for a variety of purposes, including research and therapeutic purposes.

In a preferred embodiment, OPACs as provided herein, and populations of OPACs, may be used for autologous and allogenic transplants, including matched and mismatched HLA type hematopoietic transplants. In one embodiment of the use of OPACs as allogenic hematopoietic transplants, the host is treated to reduce immunological rejection of the donor cells, or to create immunotolerance (see, e.g., U.S. Pat. Nos. 5,800,539 and 5,806,529). In another embodiment, the host is not treated to reduce immunological rejection or to create immunotolerance.

6. EXAMPLES

The following examples are intended to illustrate the present embodiments and are not to be construed to be limiting in any way. All references, whether patent references, literature references, or otherwise, cited herein are hereby incorporated by reference for all purposes.

6.1 Example 1

Isolation and Characterization of OPACs 6.1.1 Materials and Methods
Isolation of OPACs:

Term placenta was collected from healthy donor mothers after informed consent was obtained. Chorionic tissue was manually separated from amnion, and 12 g of chorionic tissue was excised and minced into 1 mm³ pieces. Minced tissue was then transferred to a 240 mL solution of dispase II at a concentration of 2.4 U/mL; tissue was incubated with dispase II for 1 hour (hr) at 37 C with agitation at 80 RPM. After incubation with dispase, digested tissues were aliquoted into 50 mL tubes to allow for centrifugation; digested tissue sample was centrifuged at 220 g for 5 minutes at room temperature (RT). After carefully decanting supernatants, pelleted tissues were resuspended and pooled into a warm collagenase II solution (270 U/mL in a 240 mL volume) and incubated for 1 hr at 37 C with agitation at 80 RPM. Digestates were aliquoted into 50 mL tubes to allow for centrifugation; digested tissue sample was centrifuged at 220 g for 5 minutes at RT. Enzyme present in digested tissues was neutralized with a 5% FBS/PBS wash. Samples were again subject to centrifugation (220 g for 5 minutes at RT). Pellets (containing liberated cells as well as tissue) were then re-suspended in 20% FBS (Hyclone)/α-MEM (Invitrogen) containing 1× penicillin-streptomycin and 1× l-glutamine or 10% FBS(Hyclone)/DMEM (Invitrogen) media also containing 1× penicillin-streptomycin and 1× l-glutamine.

Selective Adhesion Isolation of OPACs

As part of the selective adhesion strategy, cell suspensions (obtained as described above) were added to flasks that had been precoated with fibronectin (FN, Sigma), collagen (COL, StemCell Technologies), vitronectin (VN, Sigma), and laminin (LN, Sigma). Flasks were coated by incubating flasks with 10 μg/mL solutions of each protein for 1 hr at room temperature for fibronectin and collagen, 1 hr at 37° C. for vitronectin, and 2 hours at 37 C for laminin; after these incubations flasks were washed 2× with PBS.

Three hours, 24 hours, and 6 days after seeding of cell suspensions onto coated flasks, non-adherent cells/tissues were removed from establishment cultures. Cells remaining in tissue culture flasks were then allowed to proliferate. Once cultures achieved about 80-90% confluence, cells were cryopreserved.

Chorion derived adherent cells (OPACs) were separated based on cell surface expression of CD200 using magnetic assisted cell sorting (MACs) technique using anti-human CD200-PE antibody (BD Biosciences, cat 552475), anti-PE microbeads (Miltenyi, cat#130-048-801), and MACs columns (Miltenyi) according to Miltenyi's MACs column protocol.

Culture of OPACs

Conditions from the selective adhesion strategy that displayed the highest levels of alkaline phosphatase (AP) induction (LN or VN coatings, 20% FBS/α-MEM, 6 day establishment adhesion) were further expanded in conditions that encourage osteogenic functionality. These conditions included subculturing on fibronectin-coated surfaces, using commercially-available mesenchymal stem cell media, or using mesenchymal stem cell-qualified fetal bovine serum. Two cell lines from the original selective adhesion matrix were subcultured according to the following matrix on LN, VN, or FN coated surfaces, and with the three media depicted in Table 2.

TABLE 2

| | | Establishment coating | | | |
|---|---|---|---|---|---|
| | | LN | | VN | |
| media | 1 | LN | FN | VN | FN |
| | 2 | LN | FN | VN | FN |
| | 3 | LN | FN | VN | FN |

1. Hyclone FBS/αMEM
2. Lonza MSC media
3. MSC-qualifd FBS (Stem Cell Tech)/αMEM

The cells obtained using the selective adhesion matrix shown in Table 2 were then analyzed by flow cytometry and for alkaline phosphatase activity. Cells were characterized using the following assays: flow cytometry, gene expression analysis, and alkaline phosphatase (AP) activity, and protein secretion.

Gene Expression

Cells were trypsinized and nucleated cell counts were performed to determine a minimum of $1\times10^6$ to $1\times10^7$ cells. Cells were then lysed using protocol for lysis from Qiagen RNEasy kit; lysates were then passed through QIA shredder to maximize cell lysis. RNA isolation was performed using a Qiagen RNEasy kit.

RNA quantity was determined using Nanodrop ND1000 spectrophotometer; a minimum of 28 ng/μl of RNA analyzed by Nanodrop ND1000. RNA quality was measured by Agilent 2100 bioanalyzer; an rRNA ratio 28S/18S of 2.0 was used as determinant of good quality RNA. cDNA reactions were generated from RNA using High capacity cDNA archive kit protocol. Real time PCR reactions were performed using TAQMAN® universal PCR master mix from Applied Biosystems. The PCR reaction uses the 5' activity of Amplitaq Gold DNA polymerase to cleave a TAQMAN® probe during PCR. The TAQMAN® probe contains a reporter dye at 5" end and a quencher dye a the 3" end of the probe. Accumulation of the PCR products is detected directly by monitoring the increase in fluorescence of the reporter dye.

RNA was isolated from OPACs, placental stem cells, mesenchymal stem cells (ScienCell Research Labs., Carlsbad, Calif.), and human dermal fibroblasts (ScienCell Research Labs., Carlsbad, Calif.) for the osteogenesis superarray, and from OPACs and placental stem cells (for the TGF-BMP array). Cells were cultured in basal media (growth conditions for each respective cell type) for 3 days and cultured in osteogenic media (osteogenic conditions) for one week. Samples were isolated in quadruplicate using Qiagen's RNeasy Plus Mini Kit. All RNA isolation was of good quality and sufficient yield was achieved to run (as measured by Nanodrop for concentration and Agilent chip for purity). Arrays were run according to the manufacturer's protocol and results quantified on an ABI 7900.

Alkaline Phosphatase Activity

To induce osteogenesis, cells were seeded in growth medium at $5 \times 10^3$ cells/cm$^2$ for about 3 days, and then maintained in growth medium or induced with OS medium (10% FBS/DMEM) containing ascorbic acid (50 µg/mL), dexamethasone (0.1 µM), and α-glycerophosphate (10 mM) for up to 2 weeks; cells were fed bi-weekly with fresh growth or osteogenic medium.

Alkaline phosphatase (AP) activity in cell lysates was determined using a colorimetric assay (Cell Biolabs, San Diego, Calif.), which measures the formation of p-nitrophenol product; AP activity was normalized to µg of DNA (to account for any differences in cell number) using the PicoGreen dsDNA fluorescent assay. The amount of p-nitrophenol formed by cell lysates was determined by linear regression analysis from a standard curve generated using known amounts of p-nitrophenol (provided by the kit). Alkaline phosphatase activity was also assessed histochemically per manufacturer's instructions using a kit (#85) from Sigma.

Colony-Forming Unit Assay—Alkaline Phosphatase Activity

Pre-sorted OPACs containing a mixture of CD200$^-$ and CD200$^+$ cells, CD200$^+$ populations, and flow-through fractions (which contained a relatively high concentration of CD200 negative/dim populations) were seeded in osteogenic differentiation media (10% FBS/DMEM/50 µg/ml ascorbic acid/0.1 µM dexamethasone) at 22.5 cells/cm$^2$ in 35 mm gridded dishes. Cells were fed bi-weekly with osteogenic media, and after 10 days cells were assessed histochemically for alkaline phosphatase activity per manufacturer's instructions using a kit (#85) from Sigma. The number of alkaline phosphatase positive colonies was quantified visually using a stereomicroscope.

Immunofluorescent Staining

Cells were cultured on Labtek slides at 5000 cells/cm$^2$ and cultured for 2-3 days. Cells were fixed with 3.7% formaldehyde for 9 minutes, then washed 3× with PBS. After blocking for 20 minutes at room temperature with blocking buffer (10% goat serum, 2× casein, 0.3% triton), cells were stained for NG2 (chondroitin sulfate) and α-smooth muscle actin using rabbit anti-human NG2 (Chemicon, 1:150 dilution), mouse anti-human α-smooth muscle actin (Dako, 1:30 dilution).antibodies.; cells were incubated with primary antibodies overnight at 4 C. Next samples were then washed with PBS and incubated with fluorescently labeled secondary antibodies, either AlexaFluor488 anti-rabbit (Invitrogen, 1:400 dilution) or AlexaFluor488 anti-mouse (Invitrogen, 1:400 dilution); cells were incubated with secondary antibodies for 30 minutes at room temperature. Next cells were washed 3× with PBS and mounted using mounting media containing DAPI in order to counterstain for nuclei. Cells were imaged using an epifluorescence microscope.

Luminex Assay

Secreted factors in conditioned medium samples from cells were analyzed using the human bone panel 1B-11plex (cat #HBN1B-51K-11) from Millipore, according to manufacturer's instructions.

Antibody Arrays

OPACs, mesenchymal stem cells, placental stem cells, and fibroblasts were cultured in basal media (growth conditions) for 3 days and then switched to serum free media for 24 hours. Media samples were run on RayBiotech RAYBIO® Biotin Label-based Antibody Array per the manufacturer's instructions. The chemiluminescence arrays were imaged and dot sizes were analyzed using a GelLogic 2200 Imaging System and a Kodak MI imaging program, respectively.

6.1.2 Results

Selective Adhesion and Gene Expression

All 6 day adhesion conditions yielded sufficient numbers of cells for analysis, however the 3 hr and 24 hr adhesion conditions in 10% FBS/DMEM did not proliferate sufficiently to yield enough cells for analysis. The genes chosen for mRNA expression analysis included: alkaline phosphatase (AP), DLX5 (transcription factor), bone sialoprotein, RUNX2 (transcription factor), collagenase III, osterix (transcription factor), and osteocalcin. Of these genes, cells derived from the 20% FBS/αMEM media, 6-day adhesion, LN, VN, and COL coating showed increased expression in AP mRNA levels compared to bone marrow-derived mesenchymal stem cells (FIG. 1). All other genes analyzed demonstrated lower levels of gene expression in newly isolated placental cells compared to mesenchymal stem cells.

Results from immunophenotyping showed significant increases in the CD200$^{dim}$/CD200$^-$ populations in the 6 day adhesion conditions compared to placental stem cells although the highest increases were detected in the LN, VN, COL coated conditions in 20% FBS/αMEM. (FIG. 2). Flow cytometry also confirmed that OPACs are CD34$^-$ and CD105$^+$ (FIG. 2).

Culture permutations, namely the LN, VN, COL coated conditions in 20% FBS/αMEM, which yielded the increased CD200$^{dim}$/CD200$^-$ populations, also demonstrated significant increases in AP$^+$ and Stro-1$^+$ populations by flow cytometry (FIG. 3); these conditions also displayed high levels of AP gene expression vs. MSC controls. These same conditions also demonstrated significant increases in SSEA3 and SSEA4 positive populations (FIG. 4).

Functional analysis, as determined by AP activity, demonstrated inducible AP activity under osteogenic differentiation conditions (10 day induction) in the FN, LN, VN, COL coated substrates in 20% FBS/αMEM conditions, although the FN coated condition demonstrated a more moderate induction (FIG. 5).

Characterization of Cultured Cells

Immunophenotyping of cells resulting from propagation in various growth conditions demonstrated that, in the CD200$^+$ populations, between 40-60% of the cells were CD200$^+$, vs ~100% for placental stem cells (PDAC™s) described, e.g., in US Application Publication No. 2007/0275362. There was also a modest increase in the percentage of AP positive cells relative to PDAC™s, whereas the percentage of CD105 positive cells remained the same as for PDAC™s (FIG. 6).

To better define chorion derived cells (OPACs), immunofluorescence staining was conducted to stain for markers associated with cells that display osteogenic activity. Pericytes, which are cells associated with vasculature and known to harbor osteogenic activity stain positively for NG2 and α-smooth muscle actin. Therefore immunofluorescence staining studies were conducted for these markers. OPACs displayed two differences in staining compared to PDAC™s: (1) a lack of staining for α-smooth muscle actin compared to α-smooth muscle actin-positive PDAC™s, and (2) diffuse cellular localization of NG2 compared to focal adhesion localized NG2 staining for standard PDAC™s; localization of NG2 to subcellular structures such as focal adhesions carries implications in the activity of NG2 (data not shown).

After a 10 day induction under osteogenic differentiation conditions, the LN-LN medium 1 and VN-VN medium 1 conditions, as shown in FIG. 7, showed highest induction (osteogenic/basal) of AP activity (black arrow) while LN-LN medium 3 and VN-FN medium 1 demonstrated highest overall AP activity (open arrow).

To address whether the functional activity, such as osteogenic activity and T cell suppression, derived from the CD200 low/negative fraction or in the CD200$^+$ fraction of these selective adhesion cell preparations, MACs (magnetic assisted cell separation) using an anti-human CD200 antibody was used to separate these 2 cell populations. The 4 cell lines identified above as having either highest AP induction or highest overall AP activity were processed for magnetic separation based on expression of CD200 and analyzed by flow cytometry, AP activity, and AP positive colony-forming unit formation.

The immunophenotyping displayed >85% pure CD200$^+$ populations for 2 out 4 samples and that the flow-through fraction still contained CD200$^+$ cells (FIG. 8).

Cells resulting from the separation were induced with osteogenic media for 10 days and analyzed for AP activity. The results show that the CD200$^+$ fraction had decreased AP inducibility compared to the CD200$^{dim}$/CD200$^-$ fractions (FIG. 9).

CFU (colony forming unit assay) assays measure progenitor cells in a population; for example, CFU-F assays are commonly used to measure the number of progenitors in bone marrow aspirate. The CFU-AP assay estimates the number of potential osteoblastic precursors in a population. The CD200 fractions were seeded in 35 mm gridded dishes for 10 days in osteogenic media and stained for alkaline phosphates. The number of colonies per dish and the number of AP positive colonies were quantified. CD200$^+$ fractions showed no CFU-AP and the lowest total CFU activity, whereas the pre-sort, which contain the highest CD200 dim/negative populations showed the greatest number of AP positive CFU and CFU activity. Comparatively, CD200$^+$ populations had much lower levels of CFU-AP and total CFU activity (FIGS. 10 and 11).

An 11-plex Luminex assay for bone-related secreted proteins was performed on conditioned media samples from OPACs, CD200$^+$ placental stem cells (PDAC™s) and mesenchymal stem cells (MSCs). Cells were cultured for 3 days in their respective media, then incubated with serum free DMEM for 24 hours. To ascertain behavior of cells under osteogenic conditions, cells were cultured for 3 days in growth conditions, subjected to osteogenic differentiation media (media supplemented with ascorbic acid and dexamethasone) for 7 days, then incubated with serum free DMEM overnight. The results show that of the 3 cell types, OPACs constitutively secreted the highest levels of levels osteoprotegerin. Furthermore, when the three cell types were cultured under osteogenic differentiation conditions, only OPACs displayed upregulation of osteoprotegerin secretion, whereas MSCs and PDAC™s showed downregulated osteoprotegerin. This implies that in a bone microenvironment, OPACs may be better suited to inhibit osteoclast activity via release of high levels of osteoprotegerin.

Analysis of expression of 84 genes relating to osteogenesis in OPACs, PDAC™s, MSCs, and fibroblasts cultured in growth medium and in osteogenic medium was performed using a SuperArray RT2 Profiler PCR Array-Human Osteogenesis (SABiosciences, Frederick, Md.). Growth medium used in the experiment was αMEM/20% Fetal Bovine Serum comprising 1× penicillin-streptomycin, and 1× L-glutamine, and osteogenic medium used in the experiment was osteogenic medium is αMEM/20% Fetal Bovine Serum comprising 1× penicillin-streptomycin, 1×L-glutamine, 50 μg/mL ascorbic acid, and 100 nM dexamethasone. Expression of the osteogenesis-related genes was measured in OPACs, PDAC™s, MSCs, and fibroblasts cultured under growth and osteogenic differentiation conditions.

Gene expression (as measured by Ct value, the PCR cycle at which a statistically significant increase of fluorescence signal is first detected) was found for most of the osteogenic genes measured in all cell types. OPACs showed a unique gene expression profile when compared to PDAC™s, MSCs, and fibroblasts (Tables 3A-3C, respectively), and a unique gene expression induction profile, when cells were shifted from growth to osteogenic medium, when compared to PDAC™s, MSCs, and fibroblasts (Tables 3D-3F, respectively). Ct values (Tables 3A-3C) are numbers obtained directly from the PCR cycler and reported as a range; as such, these values were converted to one, two, three or four plus signs, as explained below. To calculate fold-change in gene expression in growth medium compared to osteogenic medium, a correction factors is applied to the Ct values based on the expression of housekeeping genes. This correction factor normalizes for slight differences in amount of RNA used in the PCR.

Tables 3A-3C: Osteogenic gene expression (Ct values) of OPACs vs. PDACs™ (Table 3A), OPACs vs. MSCs (Table 3B) and OPACs vs. fibroblasts (Table 3C) in growth or osteogenic media, as defined above (n=2). The expression level of the genes was classified as ++++ (very high, Ct<20). +++ (high, 20<Ct<25), ++ (medium, 25<Ct<30), + (low 30<Ct<35), − (low 35<Ct<40) or blank (no signal detected).

TABLE 3A

| | OPAC | | PDAC ™ | |
|---|---|---|---|---|
| Symbol | G | O | G | O |
| AHSG | − | | + | |
| ALPL | + | + | ++ | + |
| AMBN | | + | | |
| AMELY | + | + | + | + |
| ANXA5 | ++++ | ++++ | ++++ | ++++ |
| BGLAP | ++ | ++ | ++ | ++ |
| BGN | +++ | ++ | +++ | +++ |
| BMP1 | +++ | +++ | +++ | +++ |
| BMP2 | ++ | ++ | ++ | |
| BMP3 | + | | | |
| BMP4 | +++ | +++ | +++ | +++ |
| BMP5 | + | | + | |
| BMP6 | ++ | ++ | ++ | ++ |
| CALCR | + | ++ | + | + |
| CD36 | ++ | + | ++ | + |
| CDH11 | ++++ | ++++ | +++ | +++ |
| COL10A1 | ++ | + | + | + |
| COL11A1 | ++ | ++ | ++ | +++ |
| COL12A1 | ++++ | +++ | ++++ | +++ |
| COL14A1 | +++ | ++++ | ++ | +++ |
| COL15A1 | ++++ | ++++ | ++ | ++ |
| COL1A1 | ++++ | ++++ | ++++ | ++++ |
| COL1A2 | ++++ | ++++ | ++++ | ++++ |

TABLE 3A-continued

| Symbol | OPAC G | OPAC O | PDAC™ G | PDAC™ O |
|---|---|---|---|---|
| COL2A1 | + | + | + | |
| COL3A1 | ++++ | ++++ | ++++ | ++++ |
| COL4A3 | + | + | + | + |
| COL5A1 | ++++ | ++++ | ++++ | ++++ |
| COMP | + | ++ | + | +++ |
| CSF2 | + | + | + | |
| CSF3 | + | ++ | + | − |
| CTSK | +++ | ++++ | +++ | ++++ |
| DMP1 | − | | | |
| DSPP | + | + | | |
| EGF | + | + | ++ | + |
| EGFR | +++ | +++ | +++ | +++ |
| ENAM | + | + | | |
| FGF1 | ++ | + | ++ | ++ |
| FGF2 | +++ | +++ | +++ | +++ |
| FGF3 | | + | | |
| FGFR1 | ++ | ++ | ++ | ++ |
| FGFR2 | ++ | + | + | + |
| FLT1 | ++ | ++ | +++ | ++ |
| FN1 | ++++ | ++++ | ++++ | ++++ |
| GDF10 | | − | | |
| ICAM1 | +++ | +++ | +++ | +++ |
| IGF1 | + | ++ | + | + |
| IGF1R | +++ | +++ | +++ | +++ |
| IGF2 | + | ++ | ++ | ++ |
| ITGA1 | +++ | ++++ | +++ | +++ |
| ITGA2 | ++ | +++ | +++ | ++ |
| ITGA3 | +++ | +++ | +++ | +++ |
| ITGAM | | + | | |
| ITGB1 | ++++ | ++++ | ++++ | ++++ |
| MINPP1 | +++ | +++ | +++ | +++ |
| MMP10 | + | ++ | − | + |
| MMP2 | ++++ | ++++ | ++++ | ++++ |
| MMP8 | + | − | + | |
| MMP9 | + | ++++ | + | + |
| MSX1 | ++ | ++ | ++ | ++ |
| NFKB1 | +++ | +++ | +++ | +++ |
| PDGFA | +++ | +++ | +++ | ++ |
| PHEX | + | + | + | + |
| RUNX2 | +++ | ++ | +++ | ++ |
| SCARB1 | ++ | ++ | +++ | ++ |
| SERPINH1 | ++++ | ++++ | ++++ | ++++ |
| SMAD1 | +++ | +++ | +++ | ++ |
| SMAD2 | +++ | +++ | +++ | +++ |
| SMAD3 | +++ | +++ | +++ | +++ |
| SMAD4 | +++ | +++ | +++ | +++ |
| SOX9 | + | + | ++ | + |
| STATH | + | + | + | + |
| TFIP11 | +++ | +++ | +++ | +++ |
| TGFB1 | +++ | ++++ | +++ | +++ |
| TGFB2 | +++ | +++ | +++ | +++ |
| TGFB3 | +++ | ++++ | ++ | +++ |
| TGFBR1 | +++ | +++ | ++ | ++ |
| TGFBR2 | ++ | ++ | ++ | + |
| TNF | + | + | ++ | + |
| TUFT1 | +++ | ++ | +++ | ++ |
| TWIST1 | +++ | +++ | ++++ | +++ |
| VCAM1 | +++ | ++ | ++++ | +++ |
| VDR | ++ | +++ | +++ | ++ |
| VEGFA | +++ | +++ | +++ | +++ |
| VEGFB | +++ | +++ | +++ | +++ |

G: Relative expression vs. control in growth medium.
O: Relative expression v. control in osteogenic medium.

TABLE 3B

| Symbol | OPAC G | OPAC O | MSC G | MSC O |
|---|---|---|---|---|
| AHSG | − | − | | ++ |
| ALPL | + | + | ++ | +++ |
| AMBN | | + | | |
| AMELY | + | + | + | + |
| ANXA5 | ++++ | ++++ | ++++ | ++++ |
| BGLAP | ++ | ++ | +++ | +++ |
| BGN | +++ | ++ | +++ | ++++ |
| BMP1 | +++ | +++ | +++ | +++ |
| BMP2 | ++ | ++ | ++ | ++ |
| BMP3 | + | | + | + |
| BMP4 | +++ | +++ | ++ | +++ |
| BMP5 | + | | + | + |
| BMP6 | ++ | ++ | ++ | ++ |
| CALCR | + | ++ | − | + |
| CD36 | ++ | + | + | ++ |
| CDH11 | ++++ | ++++ | +++ | ++++ |
| COL10A1 | ++ | + | ++ | +++ |
| COL11A1 | ++ | ++ | +++ | ++++ |
| COL12A1 | ++++ | +++ | +++ | ++++ |
| COL14A1 | +++ | ++++ | ++ | +++ |
| COL15A1 | ++++ | ++++ | ++ | ++ |
| COL1A1 | ++++ | ++++ | ++++ | ++++ |
| COL1A2 | ++++ | ++++ | ++++ | ++++ |
| COL2A1 | + | + | | + |
| COL3A1 | ++++ | ++++ | +++ | ++++ |
| COL4A3 | + | + | + | ++ |
| COL5A1 | ++++ | ++++ | +++ | ++++ |
| COMP | + | ++ | + | +++ |
| CSF2 | + | + | + | + |
| CSF3 | + | ++ | + | − |
| CTSK | +++ | ++++ | +++ | ++++ |
| DMP1 | − | | | |
| DSPP | + | + | | |
| EGF | + | + | + | ++ |
| EGFR | +++ | +++ | +++ | +++ |
| ENAM | + | + | + | + |
| FGF1 | ++ | + | ++ | ++ |
| FGF2 | +++ | +++ | +++ | +++ |
| FGF3 | | + | | + |
| FGFR1 | ++ | ++ | ++ | ++ |
| FGFR2 | ++ | + | + | + |
| FLT1 | ++ | ++ | + | ++ |
| FN1 | ++++ | ++++ | ++++ | ++++ |
| GDF10 | | − | | − |
| ICAM1 | +++ | +++ | +++ | +++ |
| IGF1 | + | ++ | + | ++ |
| IGF1R | +++ | +++ | +++ | +++ |
| IGF2 | + | ++ | +++ | +++ |
| ITGA1 | +++ | ++++ | +++ | +++ |
| ITGA2 | ++ | +++ | +++ | ++ |
| ITGA3 | +++ | +++ | +++ | +++ |
| ITGAM | | | + | |
| ITGB1 | ++++ | ++++ | ++++ | ++++ |
| MINPP1 | +++ | +++ | +++ | +++ |
| MMP10 | + | ++ | + | + |
| MMP2 | ++++ | ++++ | ++++ | ++++ |
| MMP8 | + | − | + | + |
| MMP9 | + | ++++ | + | |
| MSX1 | ++ | ++ | + | + |
| NFKB1 | +++ | +++ | +++ | +++ |
| PDGFA | +++ | +++ | ++ | ++ |
| PHEX | + | + | + | ++ |
| RUNX2 | +++ | ++ | +++ | +++ |
| SCARB1 | ++ | ++ | +++ | +++ |
| SERPINH1 | ++++ | ++++ | ++++ | ++++ |
| SMAD1 | +++ | +++ | +++ | +++ |
| SMAD2 | +++ | +++ | +++ | +++ |
| SMAD3 | +++ | +++ | +++ | +++ |
| SMAD4 | +++ | +++ | +++ | +++ |
| SOX9 | + | + | ++ | +++ |
| STATH | + | + | + | + |
| TFIP11 | +++ | +++ | +++ | +++ |
| TGFB1 | +++ | ++++ | +++ | +++ |
| TGFB2 | +++ | +++ | +++ | +++ |
| TGFB3 | +++ | ++++ | ++ | +++ |
| TGFBR1 | +++ | +++ | ++ | ++ |
| TGFBR2 | ++ | ++ | ++ | + |
| TNF | + | + | + | + |
| TUFT1 | +++ | ++ | ++ | ++ |

TABLE 3B-continued

|        | OPAC |      | MSC  |      |
|--------|------|------|------|------|
| Symbol | G    | O    | G    | O    |
| TWIST1 | +++  | +++  | +++  | +++  |
| VCAM1  | +++  | ++   | +++  | +++  |
| VDR    | ++   | +++  | ++   | +++  |
| VEGFA  | +++  | +++  | +++  | +++  |
| VEGFB  | +++  | +++  | +++  | ++++ |

G: Relative expression vs. control in growth medium.
O: Relative expression v. control in osteogenic medium.

TABLE 3C

|         | OPAC |      | Fibroblast |      |
|---------|------|------|------------|------|
| Symbol  | G    | O    | G          | O    |
| AHSG    | –    |      |            | –    |
| ALPL    | +    | +    | ++         | ++   |
| AMBN    |      | +    |            |      |
| AMELY   | +    | +    | +          | +    |
| ANXA5   | ++++ | ++++ | ++++       | ++++ |
| BGLAP   | ++   | ++   | ++         | ++   |
| BGN     | +++  | ++   | +++        | +++  |
| BMP1    | +++  | +++  | +++        | +++  |
| BMP2    | ++   | ++   | +          | +    |
| BMP3    | +    |      | –          |      |
| BMP4    | +++  | +++  | +          | ++   |
| BMP5    | +    |      |            | +    |
| BMP6    | ++   | ++   | +          | ++   |
| CALCR   | +    | ++   | –          | +    |
| CD36    | ++   | +    | ++         | ++   |
| CDH11   | ++++ | ++++ | +++        | ++++ |
| COL10A1 | ++   | +    | ++         | +++  |
| COL11A1 | ++   | ++   | ++         | +++  |
| COL12A1 | ++++ | +++  | +++        | ++++ |
| COL14A1 | +++  | ++++ | +          | ++   |
| COL15A1 | ++++ | ++++ | +          | ++   |
| COL1A1  | ++++ | ++++ | +++        | ++++ |
| COL1A2  | ++++ | ++++ | ++++       | ++++ |
| COL2A1  | +    | +    |            | +    |
| COL3A1  | ++++ | ++++ | +++        | ++++ |
| COL4A3  | +    | +    | +          | ++   |
| COL5A1  | ++++ | ++++ | +++        | +++  |
| COMP    | +    | ++   | +          | +++  |
| CSF2    | +    | +    | +          | +    |
| CSF3    | +    | ++   | ++         | +    |
| CTSK    | +++  | ++++ | ++++       | ++++ |
| DMP1    | –    |      |            |      |
| DSPP    | +    | +    |            |      |
| EGF     | +    | +    | +          | +    |
| EGFR    | +++  | +++  | +++        | +++  |
| ENAM    | +    | +    | +          | +    |
| FGF1    | ++   | +    | +++        | +++  |
| FGF2    | +++  | +++  | +++        | +++  |
| FGF3    |      | +    |            |      |
| FGFR1   | ++   | ++   | ++         | ++   |
| FGFR2   | ++   | +    |            | +    |
| FLT1    | ++   | ++   | ++         | ++   |
| FN1     | ++++ | ++++ | ++++       | ++++ |
| GDF10   |      | –    |            |      |
| ICAM1   | +++  | +++  | +++        | +++  |
| IGF1    | +    | ++   |            | +    |
| IGF1R   | +++  | +++  | ++         | +++  |
| IGF2    | +    | ++   | +          | ++   |
| ITGA1   | +++  | ++++ | +++        | +++  |
| ITGA2   | ++   | +++  | ++         | ++   |
| ITGA3   | +++  | +++  | +++        | +++  |
| ITGAM   |      |      | +          | +    |
| ITGB1   | ++++ | ++++ | ++++       | ++++ |
| MINPP1  | +++  | +++  | ++         | +++  |
| MMP10   | +    | ++   | –          | +    |
| MMP2    | ++++ | ++++ | +++        | ++++ |
| MMP8    | +    | –    | +          | ++   |
| MMP9    | +    | ++++ | +          | +    |
| MSX1    | ++   | ++   | ++         | ++   |

TABLE 3C-continued

|          | OPAC |      | Fibroblast |      |
|----------|------|------|------------|------|
| Symbol   | G    | O    | G          | O    |
| NFKB1    | +++  | +++  | +++        | +++  |
| PDGFA    | +++  | +++  | ++         | ++   |
| PHEX     | +    | +    | +          | ++   |
| RUNX2    | +++  | ++   | ++         | +++  |
| SCARB1   | ++   | ++   | ++         | ++   |
| SERPINH1 | ++++ | ++++ | ++++       | ++++ |
| SMAD1    | +++  | +++  | ++         | ++   |
| SMAD2    | +++  | +++  | +++        | +++  |
| SMAD3    | +++  | +++  | ++         | +++  |
| SMAD4    | +++  | +++  | +++        | +++  |
| SOX9     | +    | +    | +          | +    |
| STATH    | +    | +    | +          | +    |
| TFIP11   | +++  | +++  | +++        | +++  |
| TGFB1    | +++  | ++++ | +++        | +++  |
| TGFB2    | +++  | +++  | ++         | +++  |
| TGFB3    | +++  | ++++ | ++         | +++  |
| TGFBR1   | +++  | +++  | ++         | ++   |
| TGFBR2   | ++   | ++   | +          | ++   |
| TNF      | +    | +    | +          | +    |
| TUFT1    | +++  | ++   | ++         | ++   |
| TWIST1   | +++  | +++  | +++        | ++++ |
| VCAM1    | +++  | ++   | +          | +    |
| VDR      | ++   | +++  | +++        | +++  |
| VEGFA    | +++  | +++  | ++         | +++  |
| VEGFB    | +++  | +++  | +++        | +++  |

G: Relative expression vs. control in growth medium.
O: Relative expression v. control in osteogenic medium.

Tables 3D-3F: Fold-difference in expression of OPACs and PDACs™, MSCs and fibroblasts of selected genes in growth medium compared to osteogenic medium. A fold difference of 10 for a particular gene, for example, indicates that the gene is induced by ten-fold in osteogenic medium compared to growth medium. Only results in which fold-induction in osteogenic medium in OPACs is at least ten-fold higher or lower than fold induction in PDACs™ (Table 3D), MSCs (Table 3E) or fibroblasts (Table 3F) are shown (blank results were assigned a value of 0 for selection).

TABLE 3D

| Symbol  | OPAC Fold difference | PDAC ™ Fold difference |
|---------|----------------------|------------------------|
| BMP2    | 11.65                |                        |
| COL11A1 | 3.64                 | 84.86                  |
| COL1A1  | 0.38                 | 9.31                   |
| COL4A3  | 1.26                 | 12.91                  |
| COL5A1  | 0.99                 | 6.84                   |
| COMP    | 17.90                | 4095.78                |
| CSF3    | 59.08                |                        |
| CTSK    | 6.88                 | 79.18                  |
| FGF1    | 0.12                 | 1.81                   |
| FGFR2   | 0.27                 | 76.81                  |
| MMP10   | 279.30               |                        |
| MMP9    | 7079936.55           | 12.25                  |
| TGFB2   | 15.77                | 0.72                   |

Fold difference: Difference between expression in growth medium and osteogenic medium.
Blank: Fold difference could not be calculated because fluorescence from one cell type was too low.

TABLE 3E

| Symbol | OPAC Fold difference | MSC Fold difference |
|--------|----------------------|---------------------|
| ALPL   | 2.02                 | 29.13               |
| CD36   | 1.08                 | 84.08               |

TABLE 3E-continued

| Symbol | OPAC Fold difference | MSC Fold difference |
|---|---|---|
| COL10A1 | 0.08 | 19.86 |
| COL11A1 | 3.64 | 43.73 |
| COL12A1 | 0.42 | 5.02 |
| COL1A1 | 0.38 | 7.23 |
| COL4A3 | 1.26 | 15.62 |
| COMP | 17.90 | 1629.84 |
| CSF3 | 59.08 | |
| CTSK | 6.88 | 148.38 |
| FGF1 | 0.12 | 1.93 |
| FGFR2 | 0.27 | 88.30 |
| IGF1R | 4.21 | 1.53 |
| IGF2 | 53.38 | 0.60 |
| ITGA2 | 8.10 | 0.16 |
| ITGA3 | 2.70 | 0.24 |
| MMP10 | 279.30 | 1.44 |
| MMP9 | 7079936.55 | |
| TGFB2 | 15.77 | 0.64 |

Fold difference: Difference between expression in growth medium and osteogenic medium.
Blank: Fold difference could not be calculated because fluorescence from one cell type was too low.

TABLE 3F

| Symbol | OPAC Fold difference | Fibroblast Fold difference |
|---|---|---|
| BMP2 | 11.65 | 0.95 |
| BMP4 | 0.23 | 72.12 |
| COL12A1 | 0.42 | 6.55 |
| COMP | 17.90 | 431.41 |
| CSF2 | 2.16 | 0.12 |
| CSF3 | 59.08 | 0.10 |
| FGF1 | 0.12 | 3.26 |
| IGF1 | 31.46 | |
| ITGA2 | 8.10 | 0.54 |
| MMP10 | 279.30 | |
| MMP8 | | 38.76 |
| MMP9 | 7079936.55 | 0.40 |

Fold difference: Difference between expression in growth medium and osteogenic medium.
Blank: Fold difference could not be calculated because fluorescence from one cell type was too low.

When OPACs and PDAC™s cultured in growth conditions were compared using a set of 84 genes in the TGFβ/BMP superfamily, OPACs generally showed higher expression of genes related to bone formation (Table 4). OPACs had greater expression of genes which related to trophic support of bone formation including BMPs (especially BMP-2) and TGF-β's. OPACs also had greater expression of genes which could be related to the trophic support of the inhibition of bone formation or bone resorption including inhibins and TGF-β's (TGF-β is implicated in both bone formation and resorption). The TGFβ/BMP superfamily represents a complex feedback system of regulation of multiple different organ systems. The fact that genes of this superfamily are expressed in OPACs at greater levels then in PDAC™s indicate that OPACs have a greater capacity to regulate bone metabolism than PDAC™s.

TABLE 4

| Symbol | OPAC | PDAC | Up/down regulation (fold) |
|---|---|---|---|
| CHRD | ++ | − | 53.25 |
| GDF7 | + | + | 12.18 |
| IGFBP3 | ++++ | ++ | 1187.56 |
| INHA | ++ | + | 16.38 |
| TGFB2 | +++ | +++ | −11.02 |

Up/down regulation: Fold difference OPAC/PDAC ™

Table 4: TGFβ/BMP superfamily members gene expression (Ct values) of OPACS, PDACs™, MSCs and fibroblasts in growth media (n=3). The expression level of the genes is classified as ++++ (very high, Ct<20). +++ (high, 20<Ct<25), ++ (medium, 25<Ct<30), + (low 30<Ct<35), − (low 35<Ct<40) or blank (no signal detected). Fold difference represents the difference in expression level when OPACs are compared to PDACs™. Only genes for which expression in OPACs exceeded expression in PDACs™, or for which expression in PDACs™ exceeded expression in OPACs, are shown.

In addition to gene expression, analysis of protein secretion (RayBiotech's RayBio® Biotin Label-based Antibody Array) from OPACs, PDAC™s, MSCs, and fibroblasts grown under growth conditions was also performed (FIG. 13). A total of 46 secreted proteins were identified between the 4 cell types. Proteins secreted by OPACs, but not PDACs™, included coagulation factor II/tissue factor, decorin, epiregulin, follistatin-like 1, IGFBP6, IGF-IIR, IL-2Rα (interleukin 2 receptor α), IL-12Rβ2 (interleukin 12 receptor subunit β2), IL-17RC (interleukin receptor C), IL-27 (interleukin 27), Latent TGF-beta binding protein 1, NCAM-1/CD56 (neural cell adhesion molecule 1), sFRP-4 (secreted frizzled-related protein 4), SMAD4, spinesin, TFPI (tissue factor pathway inhibitor), TGF-β RI/ALK5 (transforming growth factor beta receptor 1), TIMP-2 (tissue inhibitor of metalloproteases 2), and TSG-6 (tumor necrosis factor (TNF)-stimulated gene 6). Proteins secreted by OPACs but not MSCs included decorin, epiregulin, FGF-7/KGF, IGFBP-3, IL-2Rα (interleukin-2 receptor alpha), IL-3Rα (interleukin 3 receptor alpha), IL-5Rα (interleukin 5 receptor alpha), IL-17RC, IL-27, NCAM-1/CD56, SMAD4, TFPI, TGF-βR1/ALK-5, TGF-βRIII (transforming growth factor beta receptor 3), and TIMP2. Proteins, the expression of which was unique to OPACs in comparison to PDACs™ and MSCs, were decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 and TIMP-2. Of these decorin, IGFBP-6, and IL-27 are implicated in bone regulation. Of these, follistatin-like-1, sFRP-4, and TSG-6 are implicated in bone regulation.

OPACs, in a separate experiment, were also shown not to express RANKL, as assessed by quantitative RT-PCR; bone marrow-derived MSCs, however, produced significant amounts of RNA for RANKL.

6.2 Example 2

In Vivo Bone Forming Capacity of OPACs

To evaluate the in vivo bone forming capacity of OPACs, an in vivo study using a cranial defect model of bone repair was performed. Experimentally, forty-eight (48) male Hsd:RH-Foxn1rnu athymic rats (Harlan Laboratories, Indianapolis, Ind.), approximately 6 weeks old at the commencement of the study, were used. All rats had a 3 mm×5 mm defect created on each side of the calvaria. The left defect of each was treated with a negative control (HEALOS® bone graft replacement, alone) and the right defect of each was treated with either with a positive control (HEALOS®+BMP-2), a negative control (empty defect; bone is removed and not replaced with anything), or cells (PDAC™s or OPACs) loaded onto the HEALOS® carrier matrix. Eight animals were assigned to the cell treatment groups and four animals were assigned to BMP-2 and empty defect groups. The defects were treated with Healos containing the following dosages: 5 µg BMP-2, or $3 \times 10^5$-$4 \times 10^5$ cells.

Rats were sacrificed at seven (7) weeks following implantation. At necropsy, the skulls were collected and placed in 10% formaldehyde. The calvariae were scanned with a PIXI, radiographed, and then decalcified for paraffin embedding and sectioning. The coronal histological sections of the calvariae were stained with toluidine blue and H&E stain (hematoxylin and eosin). Amount of bone ingrowth to the defect was assessed by a 0 to 4 scoring system, with 4 as the largest amount.

Surgery Details

Total of forty-eight (48) plus four (4) spare male athymic rats Hsd:RH-Foxn1rnu was ordered from Harlan, Indianapolis, Ind. USA. The animals were specific pathogen free and approximately 6 weeks old upon arrival at MDS-PS-Efficacy Pharmacology. The rats were anesthetized using ketamine/xylazine delivered via intraperitoneal injection, as per standard operating procedures (SOP). General anesthesia was accomplished in approximately 3-5 minutes and was noted by a lack of response to a toe pinch. Sedation was maintained throughout surgery with isoflurane, as needed.

The skull area was shaved using an electric clipper and prepared with alcohol and chlorhexadine scrub. The animal was positioned to firmly hold the head in a forward stable position and a local anesthetic injection (approximately 0.2 ml xylocaine) was administered subcutaneously in the central cranial area between the ears. A transverse skin incision was made at the xylocaine injection site and a tissue expander placed into the central region of the rostral margin of the incision (skin flap). The expander opened up the incision and exposed the cranium. The xylocaine, that becomes gel-like, was excised and a transverse incision made in the periosteum at the parietal/interparietal suture using the scalpel blade. The periosteum was removed from the parietal bones after the incision was made. A Dremel drill at a medium speed was used to gently carve out the margin of both defects, approximately 3 mm by 5 mm area in each parietal bone, until the central piece of bone was completely free from attachment. The area was irrigated with a sterile saline drip during the drilling to prevent the bone from becoming overheated. When the piece of bone was completely detached it was removed with the Adson forceps. The edges of the defect were checked and gently smoothed using forceps if necessary. To remove bone dust and chips, the cranium was flushed with approximately 3 mL of sterile saline, which was absorbed with a piece of sterile gauze. Once clean and excess fluid removed, the defect was treated with the assigned test article. The dermis was then pulled back over the cranium and the dermal incision closed using 3.0 or 4.0 Vicryl sutures. The animal facility personnel made post-operative checks to document complete recovery of the animal. On Day 49 post-surgery, the remaining animals were euthanized by $CO_2$ asphyxiation.

Analysis Details

The calvariae were collected and placed in 10% formaldehyde. Following fixation, a Lunar dual energy x-ray absorptiometry (PIXI) was used to determine the bone mineral density (BMD) of both calvaria defects. An ROI smaller than the margins of the defect area was set and the same size ROI was used for both defects in all samples. The PIXI measured bone mineral area (BMA) and bone mineral content (BMC; g). BMC was then divided by the BMA ($mm^2$) to determine the area bone mineral density (BMD; $g/mm^2$). After completion of the PIXI densitometry the calvariae were radiographed and processed for Histology. The calvariae were radiographed, processed through decalcified tissue processing and grossed into two pieces. After grossing, the calvariae were embedded in paraffin. Three coronal sections through the defect areas were cut, each approximately 4-6 µm in thickness, and mounted on slides. One section was stained with toluidine blue and one was stained with H&E for histopathological evaluation of bone ingrowth. Determination of defect closure using x-ray scans was performed by designating a region of interest surrounding the cranial defect, use thresholding to define radio-lucent (dark residual defect) area from radio-opaque areas, quantifying these areas of residual defect using imaging software.

The results demonstrated a 20% increase in bone formation, as seen by increases in BMC and BMD, and by H&E staining, for OPACs compared to PDAC™s in this model. Based on analysis of the in vivo data, OPACS exhibited at least 20% greater bone formation than PDAC™s by histological (FIG. 14) and densitometric (PIXI) analysis (FIG. 15). Furthermore, analysis of residual defect area using x-ray scans obtained at the time of sacrifice indicated that 63% of animals in the OPAC group showed greater than 50% closure of the defect as compared to 38% of animals in the PDAC group (FIG. 16).

6.3 Example 3

Treatment of Multiple Myeloma Using OPACs 6.3.1 Materials & Methods 6.3.1.1 Establishment of OPACs Stably Transduced with Enhanced Green Fluorescentprotein (EGFP)

The pLEGFP retroviral vector containing an Enhanced Green Fluorescent Protein (EGFP) coding sequence (Clontech, Palo Alto, Calif., USA) was used to transiently transfect the packaging cell line Phoenix Eco (ecotropic) using SuperFect (QIAGEN Inc., Valencia, Calif., USA). EGFP is a red-shifted variant of wild-type *Aequorea victoria* green fluorescent protein that has been optimized for brighter fluorescence and higher expression in mammalian cells. Supernatants containing retroviral particles were collected 24-48 hours after transfection. OPACs were infected with the retroviral particles in the presence of 8 µg/ml polybrene for 12 hours at which time the media were replaced with fresh culture medium. In some experiments, cells were exposed to the supernatants containing the viral particles once more before being selected by culturing them in the presence of 200-400 µg/ml of G418 for 2-3 weeks.

6.3.1.2 Engraftment of OPACs in Myelomatous SCID-Rab Mice

As an alternative to using human bone tissue in a SCID-hu model of primary human myeloma, a system in which rabbit bones were implanted into SCID mice (SCID-rab mice), followed by introduction of myeloma cells directly into the implanted bone, was used instead. Myelomatous SCID-rab mice were constructed as previously described. See Yata, K. and Yaccoby, S., et al, Leukemia 2004; 18:1891-1897. CB.17/Icr-SCID mice (6-8-week old) were obtained from Harlan Sprague Dawley (Indianapolis, Ind., USA) and pregnant New Zealand rabbits from Myrtle Rabbitry (Thompson Station, Tenn., USA). The 3-4-week-old rabbits were deeply anesthetized with a high dose of pentobarbital sodium and euthanized by cervical dislocation. The rabbit femora and tibiae were cut into two pieces, with the proximal and distal ends kept closed, while the vertebrae were cut into small fragments ($1 \times 2$ cm$^2$).

For bone implantation, the right or left side of the SCID mouse was rinsed with alcohol and blotted with sterile gauze. The rabbit bone was inserted subcutaneously through a small (5 mm) incision. The incision was then closed with sterile surgical staples, and engraftment of the bones was allowed to take place for 6-8 weeks. In some experimental mice, two bones were simultaneously implanted contralaterally in the same mouse. For each experiment, $10$-$50 \times 10^6$ unseparated human patient-derived myeloma bone marrow cells containing $17+/-8\%$ plasma cells (PCs) or $3.3+/-1.6 \times 10^6$ PCs in 50 µl of phosphate-buffered saline (PBS) were injected directly into the implanted rabbit bone. At least two mice were used for each experiment. Mice were periodically bled from the tail vein to measure changes in levels of circulating human immunoglobulin (Ig) of the M-protein isotype.

Establishment of myeloma growth was demonstrated by increased levels of human monoclonal immunoglobulins (hIg) in mouse sera, as seen by ELISA, and by radiographic evaluation of lytic bone lesions. $5 \times 10^5$ EGFP-expressing OPACs were collected with the use of trypsin-EDTA and resuspended in 50 µl PBS. The OPACs were injected directly into the implanted bones in the SCID-rab mice. Experiments were continued for 8-16 weeks post-injection. Changes in the bone mineral density (BMD) of the implanted bones were determined using a PIXImus DEXA densitometer (GE Medical Systems LUNAR, Madison, Wis.).

6.3.1.3 Immunohistochemistry of Tissue Harvested from SCID/Rab Mice

Decalcified bone sections from primary myeloma-bearing SCID-rab mice were deparaffinized in xylene, rehydrated with ethanol, rinsed in PBS, and antigen retrieved using microwave as previously described (see Yata, K., supra). Cultured OPACs were trypsinized, cytospin slides prepared and fixed with 10% phosphate-buffered formalin for 20 min. After peroxidase quenching with 3% hydrogen peroxide for 10 min, the slides were incubated with monoclonal antibodies against EGFP, and human CD166, osteocalcin and BMP-2 (5-10 µg/ml) for 30-60 min and developed using Dako's immunoperoxidase kit and counterstaining with haematoxylin.

6.3.1.4 Von Kossa and Alizarin Red Staining

For detection of calcium deposition (von Kossa staining), OPACs were fixed in 10% phosphate-buffered formalin for 10 min. Freshly prepared 5% silver nitrate was added and the specimens left in the dark for 10 min, rinsed with distilled water and then exposed to UV light for 15 min while covered with water. The reaction was stopped by rinsing thoroughly with distilled water.

6.3.1.5 Statistical Analysis

Unless indicated otherwise, all values are expressed as mean±standard error of the mean (SEM). Student's paired t-test was used to test the effect of different culture conditions on myeloma cell numbers, viability, apoptosis, and proliferation, and to test the effect of OPACs on tumor growth and human bone mineral density (BMD) in SCID-rab mice.

6.3.1.6 Lentivirus-Mediated Transduction of OPACs

All recombinant lentiviruses were produced by transient transfection of 293T cells according to a standard protocol. Briefly, 293T cells were incubated overnight with transfection precipitate; afterward, culture medium was replaced and incubation for an additional 2 days followed. The media of the transfected cells were harvested, centrifuged at 3,000 rpm at 4° C. for 15 minutes, and filtered through a 0.22-µm-pore-size filter. The filtrate was layered on top of a 20% sucrose cushion and spun at 26,000 rpm at 4° C. for 100 minutes in a Beckman ultracentrifuge using an SW28 rotor. The pelleted virus-like particles were suspended in DMEM and stored at −80° C. Titers of the virus stocks (titer units [TU]/ml) were determined by adding aliquots of virus suspension on monolayers of 293T cells or other appropriate cell types and then assessing the percentage of GFP-positive cells by fluorescence-activated cell sorting (FACScan, Becton Dickinson). Titers greater than $10^9$ TU/ml were routinely obtained.

OPACs were transfected with the retroviral particles in the presence of 8 µg/ml polybrene for 12 hours at which time the media were replaced with fresh culture medium. In some experiment, cells were exposed to the supernatants containing the viral particles once more before being selected by culturing them in the presence of 200-400 µg/ml of G418 for 2-3 weeks.

6.3.2 Results 6.3.2.1 Matrix Mineralization by OPACs

OPACs were cultured in presence or absence of osteogenic media (alpha MEM supplemented with 10% FBS, dexamethasone (100 nM), ascorbate (0.05 mM) and beta GP (10 mM)) for approximately 2 weeks. For detection of calcium deposition cells were fixed in 10% phosphate buffered formalin for 10 minutes. Fixed cells were stained with alizarin red dye. The reaction was stopped by rinsing thoroughly with distilled water. OPACs were cultured in osteogenic media displayed signs of matrix mineralization as indicated by binding alizarin red to calcium which is deposited on the extracellular matrix produced by the cells. Matrix mineralization is one marker of osteogenic differentiation (data not shown).

6.3.2.2 OPAC Inhibition of Osteoclast Maturation

Coculture experiments: Using transwell devices, OPACs or MSCs were first cultured on the backside of the insert membrane with osteoblastic media; osteoclast precursors were then incubated in the upper chamber. To allow differentiation of osteoblasts and osteoclasts simultaneously, the inserts were then incubated with α-MEM supplemented with 10% PBS, RANKL (50 ng/ml), M-CSF (25 ng/ml), dexamethasone (100 nM), ascorbate (0.05 mM) and βGP (10 mM) for approximately 2 weeks. This procedure resulted in simultaneous growth of multinucleated osteoclasts expressing tartrate-resistant acidic phosphatase (TRAP) and osteoblasts expressing alkaline phosphate. Osteoclast precursors cultured in the absence of OPACs or mesenchymal stem cells produced an average of 120 osteoclasts (see FIG. 17). In contrast, osteoclast precursors produced an average of 40 osteoclasts when cultured in the presence of placental stem cells, and an average of 60 osteoclasts when cultured in the presence of MSCs. Thus, OPACs appear to suppress the formation of osteoclasts more effectively than do mesenchymal stem cells.

The effect of OPACs on osteoclast differentiation was significantly reduced, and significantly more osteoclasts formed, when osteoclasts and OPACs were cultured in the presence of an antibody to osteoprotegerin (anti-OPG; $p<0.04$). Additionally, significantly ($p<0.004$) more osteoclasts formed when OPACs, alone, were cultured with osteoclast precursors than when osteoclast precursors were cultured in the presence of anti-OPG. Thus, without wishing to be bound by any particular mechanism or theory, the suppression of osteoclast differentiation by OPACs appears to be mediated by OPAC-secreted osteoprotegerin.

6.3.2.3 Suppression of Multiple Myeloma Cell Growth by OPACs

Multiple myeloma cells were obtained from heparinized bone marrow (BM) aspirates from 27 patients with active myeloma during scheduled clinic visits. The bone marrow samples were separated by density centrifugation using Ficoll-Paque (specific gravity 1.077 g/ml) and the proportion of multiple myeloma plasma cells in the light-density cell fractions determined by CD38/CD45 flow cytometry. Plasma cells (PCs) were isolated using CD138 immunomagnetic bead selection and the autoMACs automated separation system (Miltenyi-Biotec, Auburn, Calif.). PC purity was determined by CD38/CD45 flow cytometry to be routinely ≥94%.

OPACs and MSCs were treated under standard conditions or osteogenic conditions and cocultured with multiple myeloma cells. For co-culture experiments transwell inserts with 1-µm pores were used. In this system, osteoblasts (i.e., MSCs or OPACs grown under osteogenic conditions), MSCs or OPACs were grown on the backside of the inserts' membranes and multiple myeloma (Con MM) cells were cultured in the upper chamber of the inserts. For culturing, 6-well inserts were flipped upside down and placed in a sterile deep dish. MSCs or OPACs were collected with trypsin-EDTA and resuspended in MSC medium (approximately $0.5 \times 10^6$/ml). Approximately 600 µl of cells were placed onto the center of the inverted insert. The dish was then covered with parafilm and placed in the incubator for 1 hour, allowing cells to adhere to the membrane. Following incubation, the inserts were flipped back and placed in 6-plate wells. When MSCs or OPACs were approximately 80% confluent, they were cultured with MSC medium or with osteoblastic medium for 2-3 weeks. The viability of the multiple myeloma cells was assessed using an MTT assay after 72 hours. The MTT assay is a colorimetric assay for measuring the activity of enzymes that reduce MTT to formazan, giving a purple color. This reduction takes place only when mitochondrial reductase enzymes are active, and therefore conversion is often used as a measure of viable cells.

The results show that undifferentiated OPACs inhibited the viability of Con MM cells by about 70% while MSCs only inhibited Con MM viability by about 40% (see FIG. 18). Under osteogenic conditions OPACs inhibited the viability of Con MM cells even more than under non-osteogenic conditions; MSCs also showed more inhibition under osteogenic conditions, although not to the same level as OPACs (see FIG. 18).

OPACs were also tested for their ability to suppress proliferation of multiple myeloma cell lines compared to fetal bone marrow-derived mesenchymal stem cells (FB MSC) in a co-culture environment that allowed for cell-cell contact. OPACs (10,000 cells/well) were cultured with multiple myeloma cell lines BN and JB (see Li et al., *Br. J. Haematology* 138(6): 802-811 (2007)), ARP1 (dexamethasone-sensitive IgA multiple myeloma-derived cell line), U266 (an IgE-producing plasma cell line), Dn and Hale (10,000 cells/well), all of which expressed luciferase, for 7 days in RPMI medium comprising 10% fetal bovine serum and antibiotics. Growth of multiple myeloma cells was assessed by detection of luciferase activity. OPACs suppressed growth of the multiple myeloma cell lines approximately as follows: BN (0.4); JB (0.5); ARP1 (0.15); U266 (0.28); Dn (0.32); and hale (0.75), wherein the number in parentheses indicates the growth of the MM cell lines in fold of growth of the MM cell lines co-cultured with FB-MSC.

In a further experiment, multiple myeloma cells from six different human patients were obtained and co-cultured at 400,000 cells/well with fetal bone marrow-derived mesenchymal stem cells or OPACs for 6-10 days. Viability of the multiple myeloma cells was significantly reduced in the presence of OPACs as compared to fetal MSCs ($p<0.03$).

6.3.2.4 Biodistribution of Labeled, Intralesionally Administered OPACs in Animals This example demonstrates the biodistribution of transfected OPACs in mice. OPACs were transfected with a luciferase reporter. The pLEGFP retroviral vector containing the EGFP (Clontech, Palo Alto, Calif., USA) was used to transiently transfect the packaging cell line Phoenix Eco using SuperFect (QIAGEN Inc., Valencia, Calif., USA). Supernatants containing retroviral particles were collected 24-48 hours after transfection. OPACs were transfected with the retroviral particles in the presence of 8 µg/ml polybrene for 12 hours at which time the medium was replaced with fresh culture medium. In some experiments, cells were exposed to the supernatants containing the viral particles once more before being selected by culturing them in the presence of 200-400 µg/ml of G418 for 2-3 weeks.

SCID-rab animals were implanted with rabbit bone as previously described. Animals having bone that showed progressive lesions were injected with labeled cells ($1 \times 10^6$ cells) directly into the lesions. Biodistribution of the OPACs in the mice was monitored by bioluminescence imaging, a real-time, non-invasive tool, at different time points. OPACs expressing EGFP could be detected in the mice at 2 weeks and 5 weeks after infection in areas where the exogenous bone was implanted into the SCID-rab animals (data not shown).

6.3.2.5 OPACs Increase Bone Mineral Density in Primary Myelomatous SCID-Rab Mice Primary myelomatous SCID-rab mice were constructed as described above. Upon establishment of myeloma growth as assessed by increased level of human monoclonal immunoglobulins (hIg) in the mice sera using ELISA and by radiographic evaluation of lytic bone lesions, $1 \times 10^6$ EGFP-expressing OPACs were collected with the use of trypsin-EDTA and resuspended in 100 µl PBS. The OPACs and PBS were injected directly into the implanted bones, comprising myelomatous lesions. Changes in the bone mineral density (BMD) of the implanted bones were determined using a PIXImus DEXA (GE Medical Systems LUNAR, Madison, Wis.) at 5 week intervals for 8-16 weeks post-injection. Intralesionally-administered OPACs were found to increase the bone mineral density (BMD) of the implanted bone compared to controls in which only medium was injected. ($p=0.0006$.) (See FIG. 19)

6.3.2.6 OPACs Increase Bone Mass in Multiple Myeloma-Affected Bones

Myelomatous SCID-rab mice constructed as described above and were injected with primary myeloma cells from a human patient. Following the development of osteolytic lesions as demonstrated by increased level of human monoclonal immunoglobulins (hIg) in the mice sera, as assessed by ELISA and by radiographic evaluation of lytic bone lesions, $5\text{-}10 \times 10^5$ EGFP-expressing OPACs were administered as described in the previous example. Experiments were continued for 8-16 weeks post-injection. The level of human myeloma cells was determined using human monoclonal immunoglobulins (hIg) in the mice sera by ELISA assay post injection of the OPACS (see FIG. 20). Changes in the bone mineral density (BMD) of the implanted bones were determined using a PIXImus DEXa (BE Medical Systems LUNAR, Madison, Wis.). Over the course of the study, implanted bones in myelomatous mice receiving intralesionally-administered OPACs showed a significant increase (0.10 gm/cm$^2$) in bone mass after 35 days post injection as compared to mice receiving only buffer ($p=0.006$).

6.3.2.7 OPACs Inhibit Bone Destruction in SCID-Rab Animals Administered an Aggressive Multiple Myeloma Cell Line Myelomatous SCID-rab mice were constructed as described above. Upon establishment of myeloma using an aggressive BN myeloma cell line (a non hyperdiploid cell line isolated from a human patient), the effect of buffer or OPACs on the myeloma cells' growth was assessed by increased level of human monoclonal immunoglobulins (hIg) in the mice sera using ELISA and by radiographic evaluation of lytic bone lesions. $0.5 \times 10^6$ EGFP-expressing OPACs ($0.5 \times 10^6$ cells) were collected with the use of trypsin-EDTA and resuspended in 50 μl PBS. The OPACs and PBS were injected directly into the implanted bones in SCID-rab mice. Experiments were continued for 8-16 weeks post-injection. Changes in the bone mineral density (BMD) of the implanted bones were determined using a PIXImus DEXA (GE Medical Systems LUNAR, Madison, Wis.). The data show that OPACs inhibited bone loss that would be attributable to this aggressive multiple myeloma cell line as measured by bone mineral density (BMD) and bone mineral content (BMC). See FIG. 21.

The reduction/elimination of loss of bone mass due to the OPACs was confirmed by X-ray radiography (data not shown). OPAC-treated animals had higher bone mass as compared to control animals as demonstrated by a significant increase in the radio-dense areas of the new bone.

6.4 Example 4

Treatment of Multiple Myeloma Using OPACs in Combination with Melphalan

This example demonstrates the effectiveness of administration of OPACs in combination with melphalan to treat osteolytic lesions associated with multiple myeloma.

Myelomatous SCID-rab mice were implanted with bone as described in Section 6.3.1.2, above. Mice were separated into groups receiving OPACS, at a dose of about 1 million in phosphate buffered saline, and controls receiving no OPACs. Mice were injected at week zero with an EGFP/Luciferase-expressing multiple myeloma cell line (BN), directly into the implanted bone, and treated with 10 mg/kg melphalan subcutaneously twice a week for four weeks, starting at week 3 (weeks 3-7 post-myeloma cell injection). At week 7, melphalan treatment was discontinued, and approximately 1 million cells/mouse unlabeled OPACs were injected intralesionally into the implanted bone. Progress of the disease was followed for an additional eleven weeks. Live animal imaging was performed at weeks 3, 7 and 18. Mice receiving OPACs showed a reduced multiple myeloma tumor cell burden, as evidenced by EGFP and luciferase fluorescence, compared to controls. Moreover, mice receiving OPACs retained bone mass better than control mice, showing an approximately 28% increase in bone mass post-melphalan as compared to a loss of approximately 4% post-melphalan for control mice.

6.5 Example 5

Production of Cryopreserved OPAC Product and Cell Bank

This Example demonstrates production of a frozen OPACs-based product.

Cryopreservation: OPACs are obtained as described in Example 1. Cells to be frozen down are harvested from culture with Trypsin-EDTA, quenched with 2% FBS in PBS, and counted on a hemacytometer. After centrifugation, cells are resuspended with 10% DMSO in FBS to a concentration of about 1 million cells/ml for cells to be used for assembly of a cell bank, and 10 million cells/ml for individual frozen cell doses. The cell solution is transferred to a freezing container, which is placed in an isopropyl alcohol bath in a −80° C. freezer. The following day, cells are transferred to liquid nitrogen.

6.5.1 Design of an OPAC Bank

A "lot" is defined as all cell doses derived from a single donor chorion. Cells maintained normal growth, karyotype, and cell surface maker phenotype for over 8 passages and 30 doublings during expansion culture. Given this limitation, doses comprise cells from 5 passages and about 20 doublings. To generate a supply of equivalent cells, a single lot is expanded in culture and is stored in a two-tiered cell bank and frozen doses. In particular, cells harvested from the primary culture, which are defined as Passage 0 cells having undergone 0 doublings, are used to initiate an expansion culture. After the first passage, approximately 4 doublings occur, and cells are frozen in a Master Cell Bank (MCB). Vials from the MCB are used to seed additional expansion cultures. After two additional passages of cells thawed from the MCB, cells are frozen down in a Working Cell Bank (WCB), approximately 12 cumulative doublings. Vials from the WCB are used to seed an expansion culture for another 2 passages, resulting in Passage 5 cells at approximately 20 doublings that are frozen down into individual doses.

6.5.2 Thawing Cells for Culture

Frozen containers of cells are placed into a sealed plastic bag and immersed in a 37° C. water bath. Containers are gently swirled until all of the contents are melted except for a small piece of ice. Containers are removed from the sealed plastic bag and a 10× volume of culture medium is slowly added to the cells with gentle mixing. A sample is counted on the hemacytometer and seeded into expansion cultures.

6.5.3 Thawing Cells for Injection

Frozen containers of cells are transferred to the administration site in a dry nitrogen shipper. Prior to administration, containers are placed into a sealed plastic bag and immersed in a 37° C. water bath. Containers are gently swirled until all of the contents are melted except for a small piece of ice. Containers are removed from the sealed plastic bag and an equal volume of 2.5% HSA/5% Dextran is added. Cells are injected with no further washing.

6.5.4 Testing and Specifications

A maternal blood sample accompanies all donor placentas. The sample is screened for Hepatitis B core antibody and surface antigen, Hepatitis C Virus antibody and nucleic acid, and HIV I and II antibody and nucleic acid. Placental processing and primary culture begins prior to the receipt of test results, but continues only for placentas associated with maternal blood samples testing negative for all viruses. A lot is rejected if the donor tests positive for any pathogen. In addition, the tests described in Table 3 are performed on the MCB, the WCB, and a sample of the cell dose material derived from a vial of the WCB. A lot is released only when all specifications are met.

TABLE 3

Cell testing and specifications

| Test | Methods | Required Result |
|---|---|---|
| Sterility | BD BACTEC PEDS PLUS/F and BACTEC Myco/F Lytic | Negative |
| Endotoxin | LAL gel clot | ≤5 EU/ml* |
| Viability | Trypan Blue | >70% viable |
| Mycoplasma | Direct culture, DNA-fluorochrome (FDA PTC 1993) | Negative |
| Identity | Flow cytometry | CD105$^+$; CD200$^{dim}$/CD200$^-$ |
| Cell Purity | Microsatellite | No contaminating cell detected |
| Karyotype | G-banding and chromosome count on metaphase cells | Normal |

*For the product designed to be 40 ml of frozen cells/dose and a maximum of 5 EU/ml, the cell product is below the upper limit of 5 EU/kg/dose for recipients over 40 kg in body weight.

6.6 Example 6

Treatment of Multiple Myeloma by Administration of OPACs

6.6.1 Intralesional Administration of OPACs in Solution

An individual presents with multiple myeloma, with symptoms of bone pain and hypercalcemia (in this case, blood calcium levels of between 3 and 4 mmol/L). X-ray imaging confirms the presence of multiple lesions in the tibia, fibula, radius and ulna. About $1\times10^7$ to about $1\times10^8$ OPACs in 1.0-2.0 mL phosphate buffered saline (PBS) per lesion are administered to the individual by injection directly into the lesion. The individual is assessed every two weeks following injection by X-ray to determine the extent of the bone lesions, and blood calcium levels are assessed every week until bone lesions are visibly reduced by X-ray, or blood calcium levels are detectably reduced. OPACs are optionally re-administered within four weeks of initial administration.

6.6.2 Intralesional Administration of OPACs in Collagen Gel

An individual presents with multiple myeloma, with symptoms of bone pain and hypercalcemia (in this case, blood calcium levels of between 3 and 4 mmol/L). X-ray imaging confirms the presence of multiple lesions in the tibia, fibula, radius and ulna. About $1\times10^7$ to about $1\times10^8$ OPACs, in 1.0-2.0 mL phosphate buffered saline (PBS) comprising collagen sufficient to form an injectable gel, per lesion, are administered to the individual by injection directly into the lesion. The individual is assessed every two weeks following injection by X-ray to determine the extent of the bone lesions, and blood calcium levels are assessed every week until bone lesions are visibly reduced by X-ray, or blood calcium levels are reduced to 3 mmol/L or less. OPACs are optionally re-administered within four weeks of initial administration.

6.6.3 Intralesional Administration of OPACs with Bone Graft Replacement

An individual presents with multiple myeloma, with symptoms of bone pain and hypercalcemia (in this case, blood calcium levels of between 3 and 4 mmol/L). X-ray imaging confirms the presence of multiple lesions in the tibia, fibula, radius and ulna. At bedside, an injectable bone graft substitute (e.g., HEALOS®) is premixed with about $1\times10^7$ to about $1\times10^8$ OPACs, in 1.0-2.0 mL phosphate buffered saline (PBS), then injected into the individual at the site of the lesions. The individual is assessed every two weeks following injection by X-ray to determine the extent of the bone lesions, and blood calcium levels are assessed every week until bone lesions are visibly reduced by X-ray, or blood calcium levels are reduced to 3 mmol/L or less. OPACs are optionally re-administered within four weeks of initial administration.

6.6.4 Intravenous Administration of OPACs

An individual presents with multiple myeloma, with symptoms of bone pain and hypercalcemia (in this case, blood calcium levels of between 3 and 4 mmol/L). X-ray imaging confirms the presence of multiple lesions in the tibia, fibula, radius and ulna. About $1\times10^9$ to about $1\times10^{10}$ OPACs, in about 750 mL phosphate buffered saline (PBS) are administered to the individual by intravenous infusion. The individual is assessed every two weeks following injection by X-ray to determine the extent of the bone lesions, and blood calcium levels are assessed every week until bone lesions are visibly reduced by X-ray, or blood calcium levels are reduced to 3 mmol/L or less. OPACs are optionally re-administered within four weeks of initial administration.

EQUIVALENTS

The compositions and methods provided herein are not to be limited in scope by the specific embodiments described herein. Indeed, various modifications of the embodiments in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method of treating an individual having multiple myeloma, comprising administering to said individual an isolated population of cells comprising osteogenic placental adherent cells (OPACs),
    wherein said OPACs are obtained from chorion, are adherent to tissue culture plastic, are negative for CD200 or are CD200$^{dim}$, and positive for CD 105,
    wherein at least 80% of the cells of said population are OPACs, and
    wherein said administering detectably reduces the progression of, halts the progression of, or improves, one or more symptoms of said multiple myeloma.

2. The method of claim 1, wherein said OPACs are SSEA3$^+$ or SSEA4$^+$.

3. The method of claim 1, wherein said OPACs are SSEA3$^+$ and SSEA4$^+$.

4. The method of claim 1, wherein said OPACs:
    express one or more genes at a detectably higher level than an equivalent number of CD200$^+$ adherent placental stem cells, wherein said one or more genes comprise one or more of BMP3 (bone morphogenetic protein 3), CDH11, COL10A1, COL14A1, COL15A1, DMP1 (dentin matrix acidic phosphoprotein 1), DSPP (dentin sialophosphoprotein), ENAM (enamelin), FGFR2 (fibroblast growth factor receptor 2), MMP10 (matrix metalloprotease 10 (stromelysin 2)), TGFB3, and/or TGFBR1, when said OPACs and said CD200$^+$ adherent placental stem cells are cultured in growth medium, as assessed by Ct values from quantitative real-time PCR;
    express one or more genes at a detectably higher level than an equivalent number of CD200$^+$ adherent placental stem cells, wherein said one or more genes comprise one or more of AMBN (ameloblastin (enamel matrix protein)), BMP2 (bone morphogenetic protein 2), CALCR (calcitonin receptor), CDH11, COL11A1, COL14A1, COL15A1, COL2A1, CSF2, CSF3, DMP1, DSPP, ENAM, FGF3, GDF10 (growth differentiation factor 10), IGF1 (insulin-like growth factor 1), ITGA1 (integrin, alpha 1 (CD49)), ITGA2 (integrin, alpha 2 (CD49B)), MMP10, MMP8 (matrix metalloprotease 8 (neutrophil collagenase)), MMP9, PDGFA (platelet-derived growth factor A), SMAD1, TGFB3, TGFBR1 and/or TGFBR2 (transforming growth factor beta, receptor 2) when said OPACs and said CD200+ adherent placental stem cells are cultured in osteogenic medium, as assessed by Ct values from quantitative real-time PCR;

express one or more genes at a detectably higher level than an equivalent number of adherent CD200+ placental stem cells that are not trophoblasts or cytotrophoblasts, wherein said one or more genes comprise one or more, or all, of CDH11, COL14A1, COL15A1, DMP1, DSPP, ENAM, MMP10, TGFB3 and/or TGFBR1 regardless of whether said OPACs and said CD200+ adherent placental stem cells are cultured in growth medium or osteogenic medium, as assessed by Ct values from quantitative real-time PCR;

express one or more genes at a detectably lower level than an equivalent number of adherent CD200+ placental stem cells that are not trophoblasts or cytotrophoblasts, wherein said one or more genes comprise one or more, or all, of AHSG (alpha-2-HS-glycoprotein), ALPL (alkaline phosphatase liver/bone/kidney), EGF (epidermal growth factor), FLT1 (fms-related tyrosine kinase 1 (vascular endothelial growth factor/vascular permeability factor receptor)), IGF2, ITGA2, ITGAM (integrin, alpha M (complement component 3 receptor 3 subunit)), SCARB1 (scavenger receptor class B, member 1), SOX9 (SRY (sex determining region Y)-box 9), TNF, TWIST1 (Twist homolog 1; formerly blepharophimosis, epicanthus inversus and ptosis 3, acrocephalosyndactyly 3), VCAM1 (vascular cell adhesion molecule 1) and/or VDR (vitamin D (1,25-dihydroxyvitamin D3) receptor) when said OPACs and said CD200+ adherent placental stem cells are cultured in growth medium, as assessed by Ct values from quantitative real-time PCR;

express one or more genes at a detectably lower level than an equivalent number of adherent CD200+ placental stem cells that are not trophoblasts or cytotrophoblasts, wherein said one or more genes comprise one or more, or all, of BGN (biglycan), COL11A1, COMP (cartilage oligomeric matrix protein), FGF1 and/or VCAM1 when said OPACs and said CD200+ adherent placental stem cells are cultured in osteogenic medium, as assessed by Ct values from quantitative real-time PCR;

express VCAM1 at a detectably lower level than an equivalent number of adherent CD200+ placental stem cells that are not trophoblasts or cytotrophoblasts, regardless of whether said OPACs and said CD200+ adherent placental stem cells are cultured in growth medium or osteogenic medium, as assessed by Ct values from quantitative real-time PCR;

express one or more genes at a detectably higher level than an equivalent number of bone marrow-derived mesenchymal stem cells, wherein said one or more genes comprise one or more, or all, of BMP4, CALCR, CD36, CDH11, COL12A1, COL14A1, COL15A1, COL3A1, COL5A1, DMP1, DSPP, FLT1, MSX1, PDGFA, TGFB3, TGFBR1 and/or TUFT1 (Tuftelin 1), when the OPACs and said bone marrow-derived mesenchymal stem cells are cultured in growth medium, as assessed by Ct values from quantitative real-time PCR;

express one or more genes at a detectably higher level than an equivalent number of bone marrow-derived mesenchymal stem cells, wherein said one or more genes comprise one or more, or all, of AMBN, CALCR, COL14A1, COL15A1, CSF3, DMP1, DSPP, ITGA1, ITGA2, MMP10, MMP9, MSX1, PDGFA, TGFB1, TGFB3, TGFBR1 and/or TGFBR2, when the OPACs and said bone marrow-derived mesenchymal stem cells are cultured in osteogenic medium, as assessed by Ct values from quantitative real-time PCR;

express one or more genes at a detectably higher level than an equivalent number of bone marrow-derived mesenchymal stem cells, wherein said one or more genes comprise one or more, or all, of CALCR, COL14A1, COL15A1, DMP1, DSPP, MSX1, PDGFA, TGFB3 and/or TGFBR1 regardless of whether said OPACs and said bone marrow-derived mesenchymal stem cells are cultured in growth medium or osteogenic medium, as assessed by Ct values from quantitative real-time PCR;

express one or more genes at a detectably lower level than an equivalent number of bone marrow-derived mesenchymal stem cells, wherein said one or more genes comprise one or more, or all, of ALPL, BGLAP (bone gamma-carboxyglutamate (gla) protein), IGF2, ITGA2, ITGAM, SCARB1 and/or SOX1, when the OPACs and said bone marrow-derived mesenchymal stem cells are cultured in growth medium, as assessed by Ct values from quantitative real-time PCR;

express one or more genes at a detectably lower level than an equivalent number of bone marrow-derived mesenchymal stem cells, wherein said one or more genes comprise one or more, or all, of AHSG, ALPL, BGLAP, BGN, BMP3, BMP5, CD36, COL10A1, COL11A1, COL12A1, COL2A1, COL4A3, COMP, EGF, FGF1, FGFR2, IGF2, MMP8, PHEX (phosphate regulating endopeptidase homolog, X-linked), RUNX2 (runt-related transcription factor 2), SCARB1, SOX1, VCAM1 and/or VEGFB, when the OPACs and said bone marrow-derived mesenchymal stem cells are cultured in osteogenic medium, as assessed by Ct values from quantitative real-time PCR; or express one or more genes at a detectably lower level than an equivalent number of bone marrow-derived mesenchymal stem cells, wherein said one or more genes comprise one or more, or all, of ALPL, BGLAP, IGF2, SCARB1 and/or SOX9, regardless of whether said OPACs and said bone marrow-derived mesenchymal stem cells are cultured in growth medium or osteogenic medium, as assessed by Ct values from quantitative real-time PCR.

5. The method of claim 1, wherein said OPACs:

express one or more genes at a detectably higher level than an equivalent number of bone marrow derived mesenchymal stem cells, wherein said one or more genes comprise one or more of BMP4, BMP6, CD36, CDH11, COL14A1, COL15A1, COL1A1, COL3A1, COL5A1, CSF2, CTSK, FGF2, FGFR1, FLT1, ITGA1, MINPP1, MMP9, MSX1, PDGFA, SERPINH1, TGFB3 and TGFBR1, wherein said OPACs and said bone marrow-derived mesenchymal stem cells have undergone an equivalent number of passages; or express one or more genes at a detectably higher level than an equivalent number of fibroblast cells, wherein said one or more genes comprise one or more of BMP4, BMP6, CDH11, COL14A1, COL15A1, COL1A1, COL3A1, COL5A1, FLT1, IGF1R, ITGA1, MINPP1, PDGFA, SERPINH1, SMAD3, TGFB1, TGFB2, TGFB3, TGFBR1, TNF, TUFT1, VCAM1 and VEGFA, and wherein said OPACs and said fibroblast cells have undergone an equivalent number of passages.

6. The method of claim 1, wherein said OPACs secrete one or more of the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 or TIMP-2.

7. The method of claim 1, wherein said OPACs secrete the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 and TIMP-2.

8. The method of claim 1, wherein said one or more symptoms are bone pain, osteocytic lesions, anemia, or renal failure.

9. The method of claim 1, comprising administering at least $1 \times 10^8$ OPACs/kg to said individual.

10. A pharmaceutical composition comprising an isolated population of cells comprising osteogenic placental adherent cells (OPACs), wherein said OPACs are obtained from chorion, adherent to tissue culture plastic, negative for CD200 or are CD200$^{dim}$, and positive for CD105, and wherein at least 80% of the cells of said population are OPACs.

11. The pharmaceutical composition of claim 10, wherein said OPACs:
express one or more genes at a detectably higher level than an equivalent number of CD200$^+$ adherent placental stem cells, wherein said one or more genes comprise one or more of BMP3 (bone morphogenetic protein 3), CDH11, COL10A1, COL14A1, COL15A1, DMP1 (dentin matrix acidic phosphoprotein 1), DSPP (dentin sialophosphoprotein), ENAM (enamelin), FGFR2 (fibroblast growth factor receptor 2), MMP10 (matrix metalloprotease 10 (stromelysin 2)), TGFB3, and/or TGFBR1, when said OPACs and said CD200$^+$ adherent placental stem cells are cultured in growth medium, as assessed by Ct values from quantitative real-time PCR;
express one or more genes at a detectably higher level than an equivalent number of CD200$^+$ adherent placental stem cells, wherein said one or more genes comprise one or more of AMBN (ameloblastin (enamel matrix protein)), BMP2 (bone morphogenetic protein 2), CALCR (calcitonin receptor), CDH11, COL11A1, COL14A1, COL15A1, COL2A1, CSF2, CSF3, DMP1, DSPP, ENAM, FGF3, GDF10 (growth differentiation factor 10), IGF1 (insulin-like growth factor 1), ITGA1 (integrin, alpha 1 (CD49)), ITGA2 (integrin, alpha 2 (CD49B)), MMP10, MMP8 (matrix metalloprotease 8 (neutrophil collagenase)), MMP9, PDGFA (platelet-derived growth factor A), SMAD1, TGFB3, TGFBR1 and/or TGFBR2 (transforming growth factor beta, receptor 2) when said OPACs and said CD200$^+$ adherent placental stem cells are cultured in osteogenic medium, as assessed by Ct values from quantitative real-time PCR;
express one or more genes at a detectably higher level than an equivalent number of adherent CD200$^+$ placental stem cells that are not trophoblasts or cytotrophoblasts, wherein said one or more genes comprise one or more, or all, of CDH11, COL14A1, COL15A1, DMP1, DSPP, ENAM, MMP10, TGFB3 and/or TGFBR1 regardless of whether said OPACs and said CD200$^+$ adherent placental stem cells are cultured in growth medium or osteogenic medium, as assessed by Ct values from quantitative real-time PCR;
express one or more genes at a detectably lower level than an equivalent number of adherent CD200$^+$ placental stem cells that are not trophoblasts or cytotrophoblasts, wherein said one or more genes comprise one or more, or all, of AHSG (alpha-2-HS-glycoprotein), ALPL (alkaline phosphatase liver/bone/kidney), EGF (epidermal growth factor), FLT1 (fms-related tyrosine kinase 1 (vascular endothelial growth factor/vascular permeability factor receptor)), IGF2, ITGA2, ITGAM (integrin, alpha M (complement component 3 receptor 3 subunit)), SCARB1 (scavenger receptor class B, member 1), SOX9 (SRY (sex determining region Y)-box 9), TNF, TWIST1 (Twist homolog 1; formerly blepharophimosis, epicanthus inversus and ptosis 3, acrocephalosyndactyly 3), VCAM1 (vascular cell adhesion molecule 1) and/or VDR (vitamin D (1,25-dihydroxyvitamin D3) receptor) when said OPACs and said CD200$^+$ adherent placental stem cells are cultured in growth medium, as assessed by Ct values from quantitative real-time PCR;
express one or more genes at a detectably lower level than an equivalent number of adherent CD200$^+$ placental stem cells that are not trophoblasts or cytotrophoblasts, wherein said one or more genes comprise one or more, or all, of BGN (biglycan), COL11A1, COMP (cartilage oligomeric matrix protein), FGF1 and/or VCAM1 when said OPACs and said CD200$^+$ adherent placental stem cells are cultured in osteogenic medium, as assessed by Ct values from quantitative real-time PCR;
express VCAM1 at a detectably lower level than an equivalent number of adherent CD200$^+$ placental stem cells that are not trophoblasts or cytotrophoblasts, regardless of whether said OPACs and said CD200$^+$ adherent placental stem cells are cultured in growth medium or osteogenic medium, as assessed by Ct values from quantitative real-time PCR;
express one or more genes at a detectably higher level than an equivalent number of bone marrow-derived mesenchymal stem cells, wherein said one or more genes comprise one or more, or all, of BMP4, CALCR, CD36, CDH11, COL12A1, COL14A1, COL15A1, COL3A1, COL5A1, DMP1, DSPP, FLT1, MSX1, PDGFA, TGFB3, TGFBR1 and/or TUFT1 (Tuftelin 1), when the OPACs and said bone marrow-derived mesenchymal stem cells are cultured in growth medium, as assessed by Ct values from quantitative real-time PCR;
express one or more genes at a detectably higher level than an equivalent number of bone marrow-derived mesenchymal stem cells, wherein said one or more genes comprise one or more, or all, of AMBN, CALCR, COL14A1, COL15A1, CSF3, DMP1, DSPP, ITGA1, ITGA2, MMP10, MMP9, MSX1, PDGFA, TGFB1, TGFB3, TGFBR1 and/or TGFBR2, when the OPACs and said bone marrow-derived mesenchymal stem cells are cultured in osteogenic medium, as assessed by Ct values from quantitative real-time PCR;
express one or more genes at a detectably higher level than an equivalent number of bone marrow-derived mesenchymal stem cells, wherein said one or more genes comprise one or more, or all, of CALCR, COL14A1, COL15A1, DMP1, DSPP, MSX1, PDGFA, TGFB3 and/or TGFBR1 regardless of whether said OPACs and said bone marrow-derived mesenchymal stem cells are cultured in growth medium or osteogenic medium, as assessed by Ct values from quantitative real-time PCR;
express one or more genes at a detectably lower level than an equivalent number of bone marrow-derived mesenchymal stem cells, wherein said one or more genes comprise one or more, or all, of ALPL, BGLAP (bone gamma-carboxyglutamate (gla) protein), IGF2, ITGA2, ITGAM, SCARB1 and/or SOX1, when the OPACs and said bone marrow-derived mesenchymal stem cells are cultured in growth medium, as assessed by Ct values from quantitative real-time PCR;

express one or more genes at a detectably lower level than an equivalent number of bone marrow-derived mesenchymal stem cells, wherein said one or more genes comprise one or more, or all, of AHSG, ALPL, BGLAP, BGN, BMP3, BMP5, CD36, COL10A1, COL11A1, COL12A1, COL2A1, COL4A3, COMP, EGF, FGF1, FGFR2, IGF2, MMP8, PHEX (phosphate regulating endopeptidase homolog, X-linked), RUNX2 (runt-related transcription factor 2), SCARB1, SOX1, VCAM1 and/or VEGFB, when the OPACs and said bone marrow-derived mesenchymal stem cells are cultured in osteogenic medium, as assessed by Ct values from quantitative real-time PCR; or express one or more genes at a detectably lower level than an equivalent number of bone marrow-derived mesenchymal stem cells, wherein said one or more genes comprise one or more, or all, of ALPL, BGLAP, IGF2, SCARB1 and/or SOX9, regardless of whether said OPACs and said bone marrow-derived mesenchymal stem cells are cultured in growth medium or osteogenic medium, as assessed by Ct values from quantitative real-time PCR.

12. The pharmaceutical composition of claim 10, wherein said OPACs express one or more of the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 or TIMP-2.

13. The pharmaceutical composition of claim 10, wherein said OPACs express the proteins decorin, epiregulin, IGFBP-3, IGFBP-6, IL-2 R alpha, IL-17RC, IL-27, Latent TGF-beta binding protein 1 (LTBP), NCAM-1, Smad4, TFPI, TGF-beta R1/ALK5 and TIMP-2.

14. The pharmaceutical composition of claim 10, wherein at least 95% of the cells of said population are OPACs.

15. The pharmaceutical composition of claim 10, wherein at least 99% of the cells of said population are OPACs.

16. The pharmaceutical composition of claim 10, wherein said OPACs are SSEA3$^+$ or SSEA4$^+$.

17. The pharmaceutical composition of claim 10, wherein said OPACs are SSEA3$^+$ and SSEA4$^+$.

18. The pharmaceutical composition of claim 10, wherein said OPACs produce osteoprotegerin.

19. The pharmaceutical composition of claim 10, wherein said OPACs are additionally negative for expression of α-smooth muscle actin, negative for expression of RANKL, positive for expression of NG2, positive for expression of osteoprotegerin, or exhibit inducible alkaline phosphatase activity.

20. The pharmaceutical composition of claim 10, wherein said OPACs are additionally negative for expression of α-smooth muscle actin, negative for expression of RANKL, positive for expression of NG2, positive for expression of osteoprotegerin, and exhibit inducible alkaline phosphatase activity.

* * * * *